United States Patent [19]

Aihara et al.

[11] Patent Number: 5,990,101
[45] Date of Patent: Nov. 23, 1999

[54] CARBAPENEM DERIVATIVES

[75] Inventors: Kazuhiro Aihara; Yuko Kano; Sohjiro Shiokawa; Toshiro Sasaki; Fumihito Setsu; Yumiko Toyooka; Miyuki Ishii; Kunio Atsumi; Katsuyoshi Iwamatsu; Atsushi Tamura, all of Kanagawa-ken, Japan

[73] Assignee: Meiji Seika Kabushiki Kaisha, Tokyo-to, Japan

[21] Appl. No.: 08/737,232

[22] PCT Filed: Mar. 8, 1996

[86] PCT No.: PCT/JP96/00573

§ 371 Date: Mar. 12, 1997

§ 102(e) Date: Mar. 12, 1997

[87] PCT Pub. No.: WO96/28455

PCT Pub. Date: Sep. 19, 1996

[30] Foreign Application Priority Data

Mar. 10, 1995 [JP] Japan ........................... 7-51616

[51] Int. Cl.$^6$ ..................... C07D 519/06; A61K 31/425; A61K 31/495
[52] U.S. Cl. ............................. 514/210; 540/302
[58] Field of Search .............. 540/302; 514/210

[56] References Cited

U.S. PATENT DOCUMENTS 4,680,292  7/1987  Christensen et al. .................... 514/210

FOREIGN PATENT DOCUMENTS 62-61985   3/1987  Japan .
4-230290   8/1992  Japan .
WO95/07912 3/1995  WIPO .

*Primary Examiner*—Mark L Berch
*Attorney, Agent, or Firm*—Wenderoth, Lind & Ponack, L.L.P.

[57] ABSTRACT

Novel carbapenem derivatives, represented by the following formula (I), having a substituted or unsubstituted imidazo [5,1-b]thiazolium-6-ylmethyl group at the 2-position are disclosed. The compounds represented by the formula (I) have potent antibacterial activity against a wide spectrum of bacteria from Gram-positive bacteria to Gram-negative bacteria including *Pseudomonas aeruginosa* and, in addition, have potent antibacterial activity against various β-lactamase-producing bacteria and MRSA and are very stable against DHP-1.

14 Claims, No Drawings

CARBAPENEM DERIVATIVES

This application is a U.S. National Phase Application under 35 USC 371, of International Application No. PCT/JP96/00573 filed Mar. 8, 1996.

BACKGROUND OF THE INVENTION

1. Field of the Invention

The present invention relates to carbapenem derivatives having potent antibacterial activity against a wide spectrum of bacteria. More particularly, the present invention relates to novel carbapenem derivatives having a substituted or unsubstituted imidazo[5,1-b]thiazolium-6-ylmethyl group at the 2-position of the carbapenem ring.

2. Background Art

Carbapenem derivatives, by virtue of potent antibacterial activity against a wide spectrum of bacteria, have been energetically studied as a highly useful β-lactam agent, and Imipenem, Panipenem, and Meropenem have been clinically used.

Both Imipenem and Panipenem, however, are used as a mixture due to instability against renal dehydropeptidase-1 ("DHP-1") in the case of Imipenem and in order to reduce nephrotoxicity in the case of Panipenem.

In recent years, research and development of carbapenem derivatives having a methyl group at the 1β-position have been made for use of these compounds as a single active ingredient in preparations because they are highly stable against DHP-1. However, many of the compounds including Meropenem, which has been recently put on the market, have a pyrrolidine skeleton at the 2-position in its chemical structure. Further, they are not always satisfactory in antibacterial activity against methicillin-resistant Staphylococcus aureus (MRSA), penicillin-resistant Streptococcus pneumoniae (PRSP), and resistant Pseudomonas aeruginosa which have posed a serious clinical problem these days. Thus, a need still exists for novel carbapenem antibiotics which have improved antibacterial activity against these bacteria.

N-Onium-salt-type carbapenem derivatives having methylene at the 2-position of the carbapenem are disclosed in Japanese Patent Laid-Open No. 151191/1986. This publication, however, neither specifically describes any bicyclic heterocyclic ring in a 5+5 form nor refers to any imidazo[5,1-b]thiazole proposed in the present invention.

The present inventors have previously found that novel cephem derivatives having heterocyclic imidazo[5,1-b]thiazole at the 3-position of the cephem ring have excellent antibacterial activity against a wide spectrum of bacteria (Japanese Patent Application Nos. 230573/1993 and 211908/1994).

SUMMARY OF THE INVENTION

The present inventors have now succeeded in synthesizing novel carbapenem derivatives having a substituted or unsubstituted imidazo[5,1-b]thiazolium-6-ylmethyl group at the 2-position and found that these derivatives have potent antibacterial activity against a wide spectrum of bacteria from Gram-positive bacteria to Gram-negative bacteria including Pseudomonas aeruginosa and, in addition, have potent antibacterial activity against β-lactamase-producing bacteria and MRSA.

Thus, an object of the present invention is to provide novel carbapenem derivatives having potent antibacterial activity against a wide spectrum of bacteria.

Another object of the present invention is to provide pharmaceutical compositions comprising the carbapenem derivative of the present invention.

A further object of the present invention is to provide a method for treating infectious diseases, comprising the step of administering the carbapenem derivative of the present invention.

The compounds according to the present invention are carbapenem derivatives represented by the following formula (I):

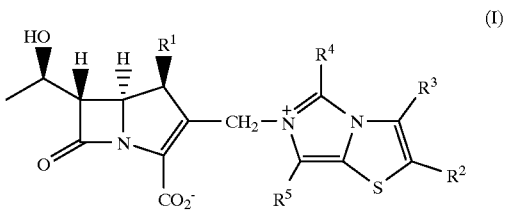

wherein
$R^1$ represents a hydrogen atom or lower alkyl; and
$R^2$, $R^3$, $R^4$ and $R^5$, which may be the same or different, represent
a hydrogen atom;
a halogen atom;
hydroxyl;
nitro;
cyano;
carboxyl;
formyl;
lower alkyl;
lower cycloalkyl;
$C_{2-4}$ alkenyl;
$C_{2-4}$ alkynyl;
lower alkyloxy;
lower alkylthio;
lower alkyloxycarbonyl;
carbamoyl;
N-lower alkylcarbamoyl;
N-(amino lower alkyl)carbamoyl;
N-(hydroxy lower alkyl)carbamoyl;
hydroxyaminocarbonyl;
lower alkylcarbonyl;
lower alkylcarbonyloxy;
amino;
N-lower alkylamino;
N-lower alkyl-N-$C_{2-4}$ alkenylamino;
formylamino;
hydroxy lower alkylcarbonylamino;
lower alkylcarbonylamino;
N-lower alkyl-N-formylamino;
lower alkyloxycarbonylamino;
lower alkyloxyamino;
ureido;
N-lower alkylureido;
oxamoyl;
lower alkylsulfonylamino;
(aminosulfonyl)amino in which hydrogen atom(s) in the two amino groups may be substituted by lower alkyl, hydroxy lower alkyl, lower alkyloxycarbonyl, or aminosulfonyloxy lower alkyl;

(aminosulfonyl)aminoxy;

hydroxyimino; or aryl, provided that one or more hydrogen atoms in the lower alkyl, lower cycloalkyl, $C_{2-4}$ alkenyl, and $C_{2-4}$ alkynyl may be substituted by a group selected from the group consisting of a halogen atom; hydroxyl; nitro; cyano; carboxyl; formyl; lower alkyloxy; lower alkylthio; lower alkyloxycarbonyl; carbamoyl; N-lower alkylcarbamoyl; hydroxyaminocarbonyl; lower alkylcarbonyl; lower alkylcarbonyloxy; amino; N-lower alkylamino; N-lower alkyl-N-$C_{2-4}$ alkenylamino; formylamino; lower alkylcarbonylamino; hydroxy lower alkylcarbonylamino; N-lower alkyl-N-formylamino; lower alkyloxycarbonylamino; lower alkyloxyamino; ureido; N-lower alkylureido; oxamoyl; lower alkylsulfonylamino; (aminosulfonyl)amino in which hydrogen atom (s) in the two amino groups may be substituted by lower alkyl, hydroxy lower alkyl, lower alkyloxycarbonyl, or aminosulfonyloxy lower alkyl; guanidino; N-lower alkylguanidino; imino; imino lower alkylamino; hydroxyimino; lower alkyloxyimino; carbamoyloxy; and a lower alkylcarbamoyloxy, or any two of $R^2$, $R^3$, $R^4$ and $R^5$ may combine together to form a five-membered heterocyclic saturated ring, containing one oxygen atom and one nitrogen atom, in which the ring may be substituted by oxo (=O), or any two of $R^2$, $R^3$, $R^4$ and $R^5$ may combine together to form a $C_{3-6}$ alkylene in which one or more methylene groups in the alkylene group may be substituted by —NH—, —O—, —S—, or —CO—; and pharmaceutically acceptable salts thereof.

The compounds represented by the formula (I) have potent antibacterial activity against a wide spectrum of bacteria from Gram-positive bacteria to Gram-negative bacteria including Pseudomonas aeruginosa and, in addition, have potent antibacterial activity against various β-lactamase-producing bacteria and MRSA and are very stable against DHP-1.

DETAILED DESCRIPTION OF THE INVENTION

Definition

As used herein, the term "lower alkyl" as a group or a part of a group means a straight or branched chain $C_{1-6}$ alkyl, preferably a straight or branched chain $C_{1-4}$ alkyl. Specific examples of this group include methyl, ethyl, propyl, isopropyl, n-butyl, iso-butyl, and t-butyl. The term "lower cycloalkyl" preferably means a $C_{3-7}$ cycloalkyl. The term "halogen atom" means a fluorine, chlorine, bromine, or iodine atom. The term "aryl" preferably means phenyl, naphthyl, tolyl or the like.

Compounds

In the formula (1), the lower alkyl group represented by $R^1$ is preferably a methyl group.

Further, in the formula (1), $R^2$, $R^3$, $R^4$ and $R^5$ may be the same and different and each are as defined above.

According to a preferred embodiment of the present invention, one or more hydrogen atoms in the lower alkyl represented by $R^2$, $R^3$, $R^4$ and $R^5$ may be substituted, and the substituent is a group selected from the group consisting of:

a halogen atom;

a hydroxyl group;

nitro;

cyano;

carboxyl;

formyl;

lower alkyloxy;

lower alkylthio;

lower alkyloxycarbonyl;

carbamoyl;

N-lower alkylcarbamoyl;

hydroxyaminocarbonyl;

lower alkylcarbonyl;

lower alkylcarbonyloxy;

amino;

N-lower alkylamino;

N-lower alkyl-N-$C_{2-4}$ alkenylamino;

formylamino;

lower alkylcarbonylamino;

hydroxy lower alkylcarbonylamino;

N-lower alkyl-N-formylamino;

lower alkyloxycarbonylamino;

lower alkyloxyamino;

ureido;

N-lower alkylureido;

oxamoyl;

lower alkylsulfonylamino;

(aminosulfonyl)amino in which hydrogen atom(s) in the two amino groups may be substituted by lower alkyl, hydroxy lower alkyl, lower alkyloxycarbonyl, or aminosulfonyloxy lower alkyl;

guanidino;

N-lower alkylguanidino;

imino;

imino lower alkylamino;

hydroxyimino;

lower alkyloxyimino;

carbamoyloxy; and a lower alkylcarbamoyloxy.

The compounds wherein $R^2$ and/or $R^3$ represent the above substituted alkyl group are particularly preferred. Examples of particularly preferred substituents for the substituted alkyl group include a halogen atom; hydroxyl; carboxyl; formyl; lower alkyloxy; lower alkyloxycarbonyl; carbamoyl; lower alkylcarbonyloxy; formylamino; lower alkyloxycarbonylamino; hydroxy lower alkylcarbonylamino; oxamoyl; lower alkylsulfonylamino; N-lower alkyl-N-formylamino; (aminosulfonyl)amino in which hydrogen atom(s) in the two amino groups may be substituted by lower alkyl, hydroxy lower alkyl, lower alkyloxycarbonyl, or aminosulfonyloxy lower alkyl; (aminosulfonyl)aminoxy; hydroxyimino; and carbamoyloxy.

According to a preferred embodiment of the present invention, any two of $R^2$, $R^3$, $R^4$ and $R^5$ may combine together to form a five-membered heterocyclic saturated ring, containing one oxygen atom and one nitrogen atom, in which the ring may be substituted by oxo (=O), or any two of $R^2$, $R^3$, $R^4$ and $R^5$ may combine together to form a $C_{3-6}$ alkylene in which one or more methylene groups in the alkylene group may be substituted by —NH—, —O—, —S—, or —CO—. Examples of compounds having such a ring structure include compounds wherein $R^2$ and $R^3$ represent a propano group and compounds wherein $R^3$ and $R^4$ represent a 1-oxo-2-azapropano group.

Specific examples of carbapenem derivatives represented by the formula (I) according to the present invention are as follows:

1. (1S,5R,6S)-6-[(1R)-1-hydroxyethyl]-2-(imidazo[5,1-b]thiazolium-6-yl)methyl-1-methyl-1-carbapen-2-em-3-carboxylate;
2. (1S,5R,6S)-6-[(1R)-1-hydroxyethyl]-2-(3-hydroxymethylimidazo[5,1-b]thiazolium-6-yl)methyl-1-methyl-1-carbapen-2-em-3-carboxylate;
3. (1S,5R,6S)-6-[(1R)-1-hydroxyethyl]-2-(3-carbamoylimidazo[5,1-b]thiazolium-6-yl)methyl-1-methyl-1-carbapen-2-em-3-carboxylate;
4. (1S,5R,6S)-6-[(1R)-1-hydroxyethyl]-2-(3-methylimidazo[5,1-b]thiazolium-6-yl)methyl-1-methyl-1-carbapen-2-em-3-carboxylate;
5. (1S,5R,6S)-6-[(1R)-1-hydroxyethyl]-2-[3-(aminosulfonyl)aminomethylimidazo[5,1-b]thiazolium-6-yl]methyl-1-methyl-1-carbapen-2-em-3-carboxylate;
6. (1S,5R,6S)-6-[(1R)-1-hydroxyethyl]-2-(3-ureidomethylimidazo[5,1-b]thiazolium-6-yl)methyl-1-methyl-1-carbapen-2-em-3-carboxylate;
7. (1S,5R,6S)-6-[(1R)-1-hydroxyethyl]-2-[3-(2-hydroxyethyl)imidazo[5,1-b]thiazolium-6-yl]methyl-1-methyl-1-carbapen-2-em-3-carboxylate;
8. (1S,5R,6S)-6-[(1R)-1-hydroxyethyl]-2-[3-N-(2-hydroxyethyl)carbamoylimidazo[5,1-b]thiazolium-6-yl]methyl-1-methyl-1-carbapen-2-em-3-carboxylate;
9. (1S,5R,6S)-6-[(1R)-1-hydroxyethyl]-2-(3-carbamoyloxymethylimidazo[5,1-b]thiazolium-6-yl)methyl-1-methyl-1-carbapen-2-em-3-carboxylate;
10. (1S,5R,6S)-6-[(1R)-1-hydroxyethyl]-2-(3-ethoxycarbonylimidazo[5,1-b]thiazolium-6-yl)methyl-1-methyl-1-carbapen-2-em-3-carboxylate;
11. (1S,5R,6S)-6-[(1R)-1-hydroxyethyl]-2-(3-formylaminomethylimidazo[5,1-b]thiazolium-6-yl)methyl-1-methyl-1-carbapen-2-em-3-carboxylate;
12. (1S,5R,6S)-6-[(1R)-1-hydroxyethyl]-2-(2-hydroxymethyl-3-methylimidazo[5,1-b]thiazolium-6-yl)methyl-1-methyl-1-carbapen-2-em-3-carboxylate;
13. (1S,5R,6S)-6-[(1R)-1-hydroxyethyl]-2-[2-(aminosulfonyl)aminomethyl-3-methylimidazo[5,1-b]thiazolium-6-yl]methyl-1-methyl-1-carbapen-2-em-3-carboxylate;
14. (1S,5R,6S)-6-[(1R)-1-hydroxyethyl]-2-(2-carbamoylimidazo[5,1-b]thiazolium-6-yl)methyl-1-methyl-1-carbapen-2-em-3-carboxylate;
15. (1S,5R,6S)-6-[(1R)-1-hydroxyethyl]-2-(5-formylaminomethylimidazo[5,1-b]thiazolium-6-yl)methyl-1-methyl-1-carbapen-2-em-3-carboxylate;
16. (1S,5R,6S)-6-[(1R)-1-hydroxyethyl]-2-(5-hydroxymethylimidazo[5,1-b]thiazolium-6-yl)methyl-1-methyl-1-carbapen-2-em-3-carboxylate;
17. (1S,5R,6S)-6-[(1R)-1-hydroxyethyl]-2-[5-((S)-1-formylamino-2-hydroxyethyl)imidazo[5,1-b]thiazolium-6-yl]methyl-1-methyl-1-carbapen-2-em-3-carboxylate;
18. (1S,5R,6S)-6-[(1R)-1-hydroxyethyl]-2-(7-hydroxymethylimidazo[5,1-b]thiazolium-6-yl)methyl-1-methyl-1-carbapen-2-em-3-carboxylate;
19. (5R,6S)-6-[(1R)-1-hydroxyethyl]-2-(imidazo[5,1-b]thiazolium-6-yl)methyl-1-carbapen-2-em-3-carboxylate;
20. (5R,6S)-6-[(1R)-1-hydroxyethyl]-2-(3-hydroxymethylimidazo[5,1-b]thiazolium-6-yl)methyl-1-carbapen-2-em-3-carboxylate; and
21. (5R,6S)-6-[(1R)-1-hydroxyethyl]-2-[3-(aminosulfonyl)aminomethylimidazo[5,1-b]thiazolium-6-yl]methyl-1-carbapen-2-em-3-carboxylate.

The compounds of the formula (I) according to the present invention may be in the form of pharmaceutically acceptable salts thereof. Examples of such salts include medically acceptable nontoxic salts. Preferable examples of salts formed at the amino and/or imidazothiazolium group include salts of hydrohalogenic acids such as hydrofluoric acid, hydrochloric acid, hydrobromic acid and hydroiodic acid; inorganic acid salts such as sulfate, nitrate, phosphate, perchlorate and carbonate; salts of carboxylic acids such as acetic acid, trichloroacetic acid, trifluoroacetic acid, hydroxyacetic acid, lactic acid, citric acid, tartaric acid, oxalic acid, benzoic acid, mandelic acid, butyric acid, maleic acid, propionic acid, formic acid and malic acid; salts of acidic amino acids such as aspartic acid and glutamic acid; and salts of organic acids such as methanesulfonic acid and p-toluenesulfonic acid. Examples of salts formed at the carboxyl group include alkali metal salts such as sodium, potassium, and lithium salts; alkaline earth metal salts such as calcium and magnesium salts; ammonium salts; salts of organic amines such as triethylamine, trimethylamine, diethylamine, pyridine, ethanolamine, triethanolamine, dicyclohexylamine, procaine, benzylamine, N-methylpiperidine, N-methylmorpholine, and diethylaniline; and salts of basic amino acids such as lysine, arginine and histidine.

Preparation of Compounds

The compounds of the general formula (I) according to the present invention can be preferably prepared in accordance with the following scheme:

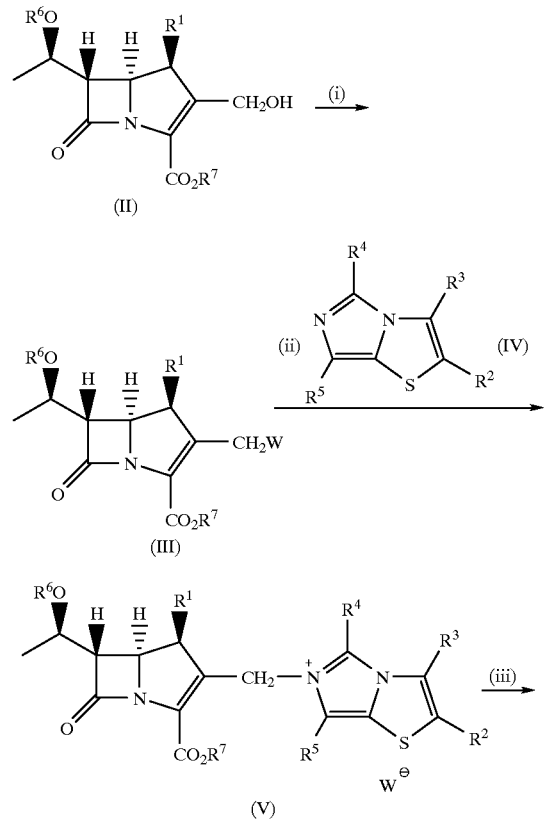

-continued

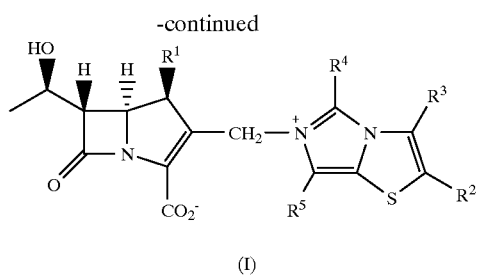

(I)

wherein $R^1$, $R^2$, $R^3$, $R^4$, and $R^5$ are as defined above in connection with the formula (I), $R^6$ represents a hydrogen atom or a protective group for a hydroxyl group (e.g., a t-butyldimethylsilyl, trimethylsilyl, triethylsilyl, allyloxycarbonyl, p-methoxybenzyloxycarbonyl, or p-nitrobenzyloxycarbonyl group), $R^7$ represents a protective group for a carboxyl group (e.g., a diphenylmethyl, benzyl, p-nitrobenzyl, p-methoxybenzyl, t-butyl, 2,2,2-trichloroethyl, or allyl group), W represents a leaving group, preferably, e.g., a halogen atom or a diphenylphosphoryloxy, p-toluenesulfonyloxy, methanesulfonyloxy, or trifluoromethanesulfonyloxy group.

In the step (i), the compound of the formula (II) can be easily converted to the compound of the formula (III) according to a known method by reacting the compound of the formula (II) with an activator for the hydroxyl group in the presence of an acid bonding agent. Specifically, the compound of the formula (II) is reacted with diphenylphosphoryl chloride, p-toluenesulfonyl chloride, methanesulfonyl chloride, or trifluoromethanesulfonic anhydride in the presence of an acid bonding agent, such as triethylamine, pyridine, diisopropylethylamine, or N,N-dimethylaminopyridine, in an inert solvent (such as acetone, acetonitrile, dichloromethane, ethyl acetate, tetrahydrofuran, dioxane, N,N-dimethylformamide, hexamethylphosphoric triamide, toluene, or a mixture of two or more of them) at a temperature of −60 to 50° C. for 30 min to 5 hr. After the completion of the reaction, the reaction solution is post-treated in a conventional manner to give the compound of the formula (III). Regarding a compound wherein W represents a halogen, a compound in a diphenylphosphoryloxy form is treated with an equivalent or excess amount of a sodium halide, a potassium halide or the like in an inert solvent (such as acetone, acetonitrile, dimethylsulfoxide, dioxane, tetrahydrofuran, N,N-dimethylformamide, hexamethylphosphoric triamide, ethyl acetate, or dichloromethane) to give the object compound. Further, a compound in an iodo form can be prepared by reacting the compound of the formula (II) with iodine in the presence of triphenylphosphine.

In the step (ii), the compound of the formula (III) is reacted with the compound of the formula (IV). Specifically, the compound of the formula (III) is reacted with an equivalent or excess amount of the compound of the formula (IV) in a suitable solvent (such as acetone, methyl ethyl ketone, ethyl acetate, dichloromethane, tetrahydrofuran, dioxane, N,N-dimethylformamide, acetonitrile, hexamethylphosphoric triamide, toluene, methanol, ethanol or the like or a mixture of two or more of them) at a temperature of −20 to 50° C. for 30 min to 48 hr. After the completion of the reaction, the reaction solution is post-treated in a conventional manner to give the compound of the formula (V).

In the step (iii), the protective groups $R^6$ and $R^7$ of the compound (V) can be removed to give the compound of the formula (I) according to the present invention. The removal of the protective groups $R^6$ and $R^7$ can be carried out by a deprotection reaction in a conventional manner commonly used in the art. When any one of or all of the protective groups can be removed under acidic conditions, the compound is treated with an mineral acid, such as hydrochloric acid, an organic acid, such as formic acid, acetic acid, or citric acid, or a Lewis acid, such as tetrabutylammonium fluoride or aluminum chloride. On the other hand, when any one of or all of the protective groups can be removed under reducing conditions, the deprotection can be carried out by catalytic reduction in the presence of one of a variety of catalysts or by treatment of the compound with a metallic reducing agent, such as zinc or iron. Further, when $R^6$ represents an allyloxycarbonyl group with $R^7$ representing an allyl group, the protective groups can be easily removed by treating the compound with one of a variety of palladium complexes.

The compound of the formula (I) thus obtained can be isolated and purified by column chromatography using a nonionic macroporous resin, by gel filtration or reversed phase chromatography using Sephadex or the like, by crystallization, or by other methods.

The compound of the formula (II) may be prepared by a known method or a method analogous thereto. Specifically, it may be prepared in accordance with the method described S. M. Schmitt, T. N. Salzmann, D. H. Shih and B. G. Christensen, J. Antibiotics, 41, 780 (1988).

Use of Compounds/Pharmaceutical Compositions

The compounds according to the present invention have potent antibacterial activity against a wide variety of Gram-positive and Gram-negative bacteria including Pseudomonas aeruginosa. In particular, they have potent antibacterial activity against various β-lactamase-producing bacteria and, further, methicillin-resistant Staphylococcus aureus (MRSA) and the like. Moreover, they have low toxicity and are stable against DHP-1. Therefore, the compounds according to the present invention can be used for the treatment of infectious diseases in animals including humans, caused by various pathogenic bacteria.

A pharmaceutical composition comprising as an active ingredient a compound of the present invention or a pharmaceutically acceptable salt thereof can be administered either orally or parenterally (e.g., intravenous injection, intramuscular injection, subcutaneous administration, rectal administration, percutaneous administration) to humans or animals other than humans. The pharmaceutical composition comprising as an active ingredient a compound of the present invention may be made into a preparation suitable for an administration route to be adopted. Specifically, it may be made into any of the following preparations: an injection for intravenous or intramuscular injection; a capsule, a tablet, a granule, a powder, a pill, fine subtilaes, or a troche for oral administration; a preparation for rectal administration; and an oleaginous suppository. The above-described various preparations can be prepared by a conventional method using an excipient, a filler, a binder, a wetting agent, a disintegrating agent, a surface active agent, a lubricant, a dispersing agent, a buffer, a preservative, a solubilizer, an antiseptic, a flavor, a soothing agent, a stabilizer and the like. Examples of the above additives which are nontoxic and employable in the preparations include milk sugar, fruit sugar, grape sugar, starch, gelatin, magnesium carbonate, synthetic magnesium silicate, talc, magnesium stearate, methyl cellulose or a salt thereof, gum arabic, polyethylene glycol, syrup, vaseline, glycerin, ethanol, propylene glycol, citric acid, sodium chloride, sodium sulfite and sodium phosphate.

The dosage of the compound of the present invention is properly determined in consideration of the regimen, the age and sex of a patient, and the conditions of disease. However, for the treatment of infectious disease, approximately 100 mg to 2000 mg, preferably 200 mg to 1000 mg of the compound is generally administered per day for adult human, desirably at one time or several times.

Preparation 1

2-hydroxymethyl-3-methylimidazo[5,1-b]thiazole

A 1.56 g portion of sodium boron hydride was added to 60 ml of an ethanol solution containing 1.684 g of 2-ethoxycarbonyl-3-methylimidazo[5,1-b]thiazole, and the mixture was then stirred at room temperature for 4 days. The solvent was evaporated under reduced pressure, and water was then added thereto. The solution was extracted twice with dichloromethane, and the combined organic layer was dried over anhydrous magnesium sulfate and then filtered. Afterward, the solvent was evaporated under reduced pressure to obtain 1.33 g of the title compound.

NMR (CDCl$_3$) δ: 2.39 (3H, s), 4.70 (2H, s), 7.07 (1H, s), 7.84 (1H, s)

Preparation 2

2-formylaminomethyl-3-methylimidazo[5,1-b]thiazole a) 2-phthalimidomethyl-3-methylimidazo[5,1-b]thiazole Under an argon atmosphere at room temperature, 0.705 ml of diethyl azodicarboxylate was added dropwise to 10 ml of an anhydrous tetrahydrofuran solution containing 505 mg of 2-hydroxymethyl-3-methylimidazo[5,1-b]thiazole, 662 mg of phthalimide and 1180 mg of triphenylphosphine, and the mixture was then stirred at room temperature for 4.5 hours. The solvent was evaporated under reduced pressure to obtain an oil, and this oil was then purified by a silica gel column chromatograph and successively Cephadex LH-20 to obtain 389.3 mg of 2-phthalimidomethyl-3-methylimidazo[5,1-b]thiazole as a lemon crystal.

NMR (CDCl$_3$) δ: 2.60 (3H, s), 4.86 (2H, s), 7.03 (1H, s), 7.73–7.76 (2H, m), 7.86–7.89 (2H, m), 7.87 (1H, s)

MS (E1): 297 (M$^+$)

b) 2-aminomethyl-3-methylimidazo[5,1-b]thiazole

A 0.052 ml portion of anhydrous hydrazine was added to 15 ml of a dry methanol solution containing 380 mg of 2-phthalimidomethyl-3-methylimidazo[5,1-b]thiazole, followed by heating under reflux for 6 hours. The reaction solution was cooled on ice, and the resulting crystal was filtered and then washed with a small amount of cold methanol. The filtrate was concentrated under reduced pressure, and to the resulting residue, 15 ml of dichloromethane was added. Afterward, the solution was extracted with 15 ml of 2N hydrochloric acid, and the hydrochloric acid extract was alkalified with potassium hydroxide. The organic layer extracted from the aqueous layer with dichloromethane (40 ml×3) was dried over anhydrous potassium carbonate, followed by filtration. The solvent was then evaporated under reduced pressure to obtain 185 mg of 2-aminomethyl-3-methylimidazo[5,1-b]thiazole as a milky white powder.

NMR (CDCl$_3$) δ: 2.36 (3H, s), 3.91 (2H, s), 7.07 (1H, s), 7.82 (1H, s)

MS (E1): 167 (M$^+$)

c) 2-(formylamino)ethyl-3-methylimidazo[5,1-b]thiazole

A mixed solution of 0.26 ml of anhydrous acetic acid and 0.52 ml of formic acid which had been beforehand reacted with each other at 55° C. for 20 minutes was added to 5 ml of a dry dichloromethane solution containing 92 mg of 2-aminomethyl-3-methylimidazo[5,1-b]thiazole at room temperature, followed by stirring at room temperature for 1 hour. Further, 2 ml of water was added the reaction solution, and the solution was then alkalified with anhydrous potassium carbonate under stirring. The organic layer extracted with dichloromethane (15 ml×3) was dried over anhydrous potassium carbonate, followed by filtration, and the solvent was then evaporated under reduced pressure. The resulting crude product was purified by a silica gel column chromatograph to obtain 101.5 mg of the title compound as a colorless needle crystal.

NMR (CDCl$_3$) δ: 2.43 (3H, s), 4.49 (2H, d, J=6.0 Hz), 6.33 (1H, br.s), 7.06 (1H, s), 7.84 (1H, s), 8.26 (1H, s)

MS (E1): 195 (M$^+$)

Preparation 3

3-(N-allyloxycarbonyl-N-aminosulfonylamino)methyl imidazo[5,1-b]thiazole

Under an argon atmosphere at −51° C., 0.71 ml of diethyl azodicarboxylate was added dropwise to 5 ml of an anhydrous tetrahydrofuran solution containing 463 mg of 3-hydroxymethylimidazo[5,1-b]thiazole, 811 mg of N-allyloxycarbonyl-N-aminosulfonylamide and 1180 mg of triphenylphosphine, and the mixture was then stirred at −51° C. to −37° C. for 15 minutes and further stirred for 70 minutes, while the solution was heated up to room temperature. The solvent was evaporated under reduced pressure to obtain an oil, and this oil was then dissolved in 50 ml of ethyl acetate. Further, the solution was extracted with 2N hydrochloric acid (30 ml×2), and the combined aqueous layer was then washed with 20 ml of ethyl acetate. After neutralized (pH 7) with sodium hydrogencarbonate, the neutralized solution was extracted with ethyl acetate (100 ml×2). The thus extracted organic layer was dried over anhydrous magnesium sulfate and then filtered, and the solvent was evaporated under reduced pressure. Afterward, the resulting oil was purified by a silica gel column chromatograph and successively Cephadex LH-20 to obtain 145.6 mg of the title compound in a milky white amorphous state.

NMR (CDCl$_3$) δ: 4.85 (2H, dt, J$_1$=5.9 Hz, J$_2$=1.2 Hz), 5.01 (2H, s), 5.36–5.48 (2H, m), 5.93–6.07 (1H, m), 6.70 (1H, s), 6.91 (1H, s), 7.1 (2H, br.s), 8.01 (1H, s)

MS (FD): 317 (M$^+$+1)

Preparation 4

2-(N-allyloxycarbonyl-N-aminosulfonylamino)methyl-3-methylimidazo[5,1-b]thiazole Under an argon atmosphere at −37° C., 0.51 ml of diethyl azodicarboxylate was added dropwise to 6.7 ml of an anhydrous tetrahydrofuran solution containing 365 mg of 2-hydroxymethyl-3-methylimidazo[5,1-b]thiazole, 586 mg of N-allyloxycarbonyl-N-aminosulfonylamine and 854 mg of triphenylphosphine, and the mixture was then stirred at −37° C. to −20° C. for 110 minutes. The solvent was evaporated under reduced pressure to obtain an oil, and this oil was then suspended in 50 ml of dichloromethane. Further, the suspension was extracted with 2N hydrochloric acid (15 ml×2), and the combined aqueous layer was then washed with 20 ml of dichloromethane. After alkalified with anhydrous potassium carbonate, the solution was further extracted with dichloromethane (30 ml×3). The combined organic layer was washed with a semi-saturated saline solution, dried (anhydrous magnesium sulfate:anhydrous potassium carbonate=1:1), and then filtered, and the solvent was evaporated under reduced pressure. Afterward, the resulting oil was purified by a silica gel column chromatograph and successively Cephadex LH-20 to obtain 208.5 mg of the title compound as a milky white powder.

NMR (CD$_3$COCD$_3$) δ: 2.49 (3H, s), 4.81 (2H, dt, J$_1$=5.6 Hz, J$_2$=1.4 Hz), 4.98 (2H, s), 5.27 (1H, dq, J$_1$=10.5 Hz, J$_2$=1.4 Hz), 5.36 (1H, dq, J$_1$=16.7 Hz, J$_2$=1.6 Hz), 5.98–6.11 (1H, m), 6.96 (1H, s), 7.12 (2H, br.s), 7.99 (1H, s)

MS (EI): 330 (M$^+$)

Preparation 5

3-[2-(N-allyloxycarbonyl-N-aminosulfonylamino) ethyl]imidazo[5,1-b]thiazole

Under an argon atmosphere at −38° C., 0.77 ml of diethyl azodicarboxylate was added dropwise to 10 ml of an anhydrous tetrahydrofuran solution containing 550 mg of 3-(2-hydroxyethyl)imidazo[5,1-b]thiazole, 884 mg of N-allyloxycarbonyl-N-aminosulfonylamine and 1286 mg of triphenylphosphine, and the mixture was then stirred at −38° C. to −32° C. for 30 minutes and further stirred for 10 minutes while the solution was heated up to 0° C. The solvent was evaporated under reduced pressure to obtain an oil, and this oil was then dissolved in 50 ml of dichloromethane. Further, extraction was carried out with 2N hydrochloric acid (20 ml×2), and the combined aqueous layer was then washed with 10 ml of dichloromethane. Afterward, the solution was adjusted to pH 9 with anhydrous potassium carbonate, and then subjected to extraction with dichloromethane (30 ml×2). The dichloromethane extract was dried (anhydrous magnesium sulfate:anhydrous potassium carbonate=1:1) and then filtered, and the solvent was evaporated under reduced pressure. Afterward, the resulting oil was purified by a silica gel column chromatograph to obtain 548 mg of the title compound as a milky white amorphous.

NMR (CDCl$_3$) δ: 3.12 (2H, br.t), 3.98–4.03 (2H, m), 4.62–4.64 (2H, m), 5.26–5.37 (2H, m), 5.76–5.89 (1H, m), 6.58 (1H, s), 6.6 (2H, br.s), 7.04 (1H, s), 8.12 (1H, s)

Preparation 6

3-ureidomethylimidazo[5,1-b]thiazole

A 1 ml portion of ice-cooled water and 0.5 ml of 5N hydrochloric acid were added to a mixture of 200 mg of 3-aminomethylimidazo[5,1-b]thiazole and 0.5 g of ice, and the mixture was then stirred at 80° C. for 5 minutes. To this solution, 254 mg of sodium cyanate was added, followed by stirring at the same temperature for 1 hour. After cooled to room temperature, the reaction solution was washed once with diethyl ether. Further, potassium carbonate was added to the separated aqueous layer to alkalify the same, and methanol was further added thereto. The solution was sufficiently stirred, and then filtered to remove impurities therefrom. The resulting filtrate was concentrated under reduced pressure, and then allowed to stand at 0° C. overnight. Afterward, the precipitated crystal was collected by filtration to obtain 38 mg of 3-ureidomethylimidazo[5,1-b] thiazole. Furthermore, the mother liquor from which the crystal was collected by the filtration was purified by a column chromatograph of Diaion HP-20 Resin to obtain 49 mg of the title compound.

NMR (DMSO-d$_6$) δ: 4.37 (2H, d, J=6.0 Hz), 5.69 (2H, br), 6.59 (1H, m), 6.96 (1H, s), 7.04 (1H, s), 7.20 (1H, s)

Preparation 7

3-N-(2-hydroxyethyl)carbamoylimidazo[5,1-b] thiazole

A 62 mg portion of ethanolamine was added to 3 ml of an ethanol solution containing 170 mg of 3-ethoxycarbonylimidazo[5,1-b]thiazole, and the mixture was then heated under reflux for 4 hours. The reaction solution was cooled, concentrated under reduced pressure, and then purified by a column chromatograph of Diaion HP-20 Resin to obtain 190 mg of the title compound.

NMR (DMSO-d$_6$) δ: 2.57 (2H, t, J=5.7 Hz), 3.53 (2H, t, J=6.0 Hz), 7.11 (1H, s), 8.09 (1H, s), 8.53 (1H, s), 8.78 (1H, s)

MS (EI): 211 (M$^+$)

Preparation 8

3-[N-(2-allyloxycarbonylaminoethyl)carbamoyl] imidazo[5,1-b]thiazole

A 7 mg portion of ethylenediamine was added to 319 ml of 3-ethoxycarbonylimidazo[5,1-b]thiazole, and the mixture was then stirred at room temperature for 30 minutes. Then, ethylenediamine was evaporated under reduced pressure, followed by toluene azeotropy. To the resulting residue, 6 ml of dichloromethane and 6 ml of water were added, and 0.95 ml of allyl chloroformate was added under ice-cooling. Afterward, a sodium hydrogencarbonate solution was added thereto, followed by stirring under ice-cooling for 5 hours, while the pH of the aqueous layer was adjusted to 8. The organic layer was separated, and extraction from the aqueous layer was then carried out three times with dichloromethane. The organic layer was dried over anhydrous magnesium sulfate, and after the drying agent was removed therefrom by filtration, the solvent was evaporated under reduced pressure. The resulting residue was purified by a silica gel column chromatograph to obtain 311 mg of the title compound.

NMR (CDCl$_3$) δ: 3.4–3.6 (4H, m), 4.60 (2H, m), 5.15–5.35 (3H, m), 5.8–5.95 (1H, m), 7.13 (1H, s), 7.40 (1H, s), 7.60 (1H, br.s), 8.70 (1H, s)

Preparation 9

3-[(allyloxycarbonylaminomethyl)carbonylamino] methyl imidazo[5,1-b]thiazole

A 5 ml portion of a dichloromethane solution containing 307 mg of N-allyloxycarbonyl glycine was cooled on ice, and 287 mg of 1-hydroxybenzotriazole and 438 mg of 1,3-dicyclohexylcarbodiimide were further added to the cooled mixture, followed by stirring under ice-cooling for 2 hours. Further, 5 ml of dichloromethane containing 3-aminomethylimidazo[5,1-b]thiazole and 10 ml of DMF were added thereto, and dichloromethane was then evaporated under reduced pressure, followed by stirring at room temperature for 1.5 hours. To the reaction solution, a saline solution was added, and extraction was then carried out three times with ethyl acetate. Afterward, the resulting organic layer was dried over anhydrous magnesium sulfate, and after the removal of the drying agent by filtration, the solvent was evaporated under reduced pressure. The resulting residue was purified by a silica gel column chromatograph to obtain 387 mg of the title compound.

NMR (CDCl$_3$) δ: 3.89 (2H, d, J=5.9 Hz), 4.51 (2H, d, J=5.5 Hz), 5.1–5.3 (2H, m), 5.75–5.95 (1H, m), 6.08 (1H, br.s), 6.74 (1H, s), 7.00 (1H, s), 7.78 (1H, br.s), 8.04 (1H, s)

EXAMPLE 1

(1S,5R,6S)-6-[(1R)-1-hydroxyethyl]-2-(3-hydroxymethylimidazo[5,1-b]thiazolium-6-yl)methyl-1-methyl-1-carbapen-2-em-3-carboxylate (internal salt)

(1) Under an argon atmosphere at −30° C., 0.416 ml of diphenylphosphorous chloride and 1 ml of a dichloromethane solution containing of 244 mg of 4-dimethylaminopyridine were added to 4 ml of a dichloromethane solution containing 696 mg of allyl (1S,5R,6S)-6-[(1R)-1-(allyloxycarbonyloxy)ethyl]-2-hydroxymethyl-1-methyl-1-carbapen- 2-em-3-carboxylic acid allyl ester, and the mixture was then stirred at the same temperature for 1 hour. After dilution with 15 ml of dichloromethane, 5 ml of a semi-saturated aqueous sodium hydrogencarbonate solution was added thereto, followed by stirring for 5 minutes. The organic layer was separated, and then washed with 0.1N hydrochloric acid and a semi-saturated saline solution in succession. Further, the solution was dried over anhydrous magnesium sulfate. After the removal of the drying agent by filtration, 4 ml of DMF was added, and dichloromethane was evaporated under reduced pressure to obtain a DMF solution of a phosphate.

(2) To the total amount of the DMF solution of the phosphate obtained in the above-mentioned (1), 426 mg of sodium iodide and 440 mg of 3-hydroxymethylimidazo[5,1-b]thiazole were added in succession, followed by stirring at room temperature for 45 minutes, while light was shut out. Further, the solution was diluted with 200 ml of ethyl acetate, washed with a saturated saline solution three times, and then dried over anhydrous magnesium sulfate, and the solvent was evaporated under reduced pressure.

(3) To 40 ml of a dichloromethane solution of the mixture obtained in the above-mentioned (2), 149 mg of triphenylphosphine, 363 mg of potassium 2-ethylhexanoate, 0.316 ml of 2-ethylhexanoic acid and 438 mg of tetrakis (triphenylphosphine)palladium were added in succession, and the mixture was then stirred at room temperature for 2 hours. Then, 50 ml of water was added to the reaction solution, and after vigorous stirring, the organic layer was separated and then subjected to extraction twice with water. The combined aqueous layer was concentrated under reduced pressure, followed by freeze-drying. The resulting mixture was purified by a Diaion HP-20 column chromatograph and a Cephadex LH-20 column chromatograph to obtain 140 mg of the title compound.

NMR (D$_2$O) δ(HOD=4.80 ppm): 1.09 (3H, d, J=7.2 Hz), 1.25 (3H, d, J=6.3 Hz), 3.04 (1H, m), 3.47 (1H, m), 4.21 (2H, m), 4.87 (2H, s), 5.19 (1H, d, J=15.0 Hz), 5.80 (1H, d, J=15.0 Hz), 7.47 (1H, s), 7.75 (1H, s), 9.43 (1H, s)

EXAMPLE 2

(1S,5R,6S)-6-[(1R)-1-hydroxyethyl]-2-(imidazo[5,1-b]thiazolium-6-yl)methyl-1-methyl-1-carbapen-2-em-3-carboxylate (internal salt)

The same procedure as in Example 1 was repeated except that 91 mg of allyl (1S,5R,6S)-6-[(1R)-1-allyloxycarbonyloxyethyl]-2-hydroxymethyl-1-methyl-1-carbapen-2-em-3-carboxylate and 155 mg of imidazo[5,1-b]thiazole were used, thereby obtaining 21.6 mg of the title compound.

NMR (D$_2$O) δ(HOD=4.80 ppm): 1.14 (3H, d, J=7.2 Hz), 1.31 (3H, d, J=6.4 Hz), 3.10 (1H, m), 3.52 (1H, dd, J$_1$=6.1 Hz, J$_2$=3.1 Hz), 4.20–4.30 (2H, m), 5.24 (1H, d, J=15.0 Hz), 5.82 (1H, d, J=15.0 Hz), 7.59 (1H, d, J=4.2 Hz), 7.72 (1H, s), 7.97 (1H, d, J=4.2 Hz), 9.41 (1H, s)

EXAMPLE 3

(1S,5R,6S)-6-[(1R)-1-hydroxyethyl]-2-(3-carbamoylimidazo[5,1-b]thiazolium-6-yl)methyl-1-methyl-1-carbapen-2-em-3-carboxylate (internal salt)

The same procedure as in Example 1 was repeated except that 113 mg of allyl (1S,5R,6S)-6-[(1R)-1-allyloxycarbonyloxyethyl]-2-hydroxymethyl-1-methyl-1-carbapen-2-em-3-carboxylate and 260 mg of 3-carbamoylimidazo[5,1-b]thiazole were used, thereby obtaining 9.6 mg of the title compound.

NMR (D$_2$O) δ(HOD=4.80 ppm): 1.12 (3H, d), 1.28 (3H, d), 3.05 (1H, m), 3.50 (1H, dd), 4.15–4.30 (2H, m), 5.25 (1H, d), 5.83 (1H, d), 7.82 (1H, s), 8.40 (1H, s), 9.77 (1H, s)

EXAMPLE 4

(1S,5R,6S)-6-[(1R)-1-hydroxyethyl]-2-[5-(formylamino)methylimidazo[5,1-b]thiazolium-6-yl]methyl-1-methyl- 1-carbapen-2-em-3-carboxylate (internal salt)

The same procedure as in Example 1 was repeated except that 142 mg of allyl (1S,5R,6S)-6-[(1R)-1-allyloxycarbonyloxyethyl]-2-hydroxymethyl-1-methyl-1-carbapen-2-em-3-carboxylate and 350 mg of (5-formylamino)methylimidazo[5,1-b]thiazole were used, thereby obtaining 10.9 mg of the title compound.

NMR (D$_2$O) δ(HOD=4.80 ppm): 1.12 (3H, d, J=7.2 Hz), 1.27 (3H, d, J=6.3 Hz), 2.98 (1H, m), 3.48 (1H, dd, J$_1$=6.1 Hz, J$_2$=2.8 Hz), 4.14–4.28 (2H, m), 4.99 (2H, s), 5.20 (1H, d, J=15.7 Hz), 5.97 (1H, d, J=15.7 Hz), 7.60 (1H, d, J=4.3 Hz), 7.75 (1H, s), 8.10 (1H, d, J=4.3 Hz), 8.21 (1H, s)

EXAMPLE 5

(1S,5R,6S)-6-[(1R)-1-hydroxyethyl]-2-[5-(2-hydroxyethyl)imidazo[5,1-b]thiazolium-6-yl]methyl-1-methyl-1-carbapen-2-em-3-carboxylate (internal salt)

The same procedure as in Example 1 was repeated except that 134 mg of allyl (1S,5R,6S)-6-[(1R)-1-allyloxycarbonyloxyethyl]-2-hydroxymethyl-1-methyl-1-carbapen-2-em-3-carboxylate and 185 mg of 5-(2-hydroxyethyl)imidazo[5,1-b]thiazole were used, thereby obtaining 8.6 mg of the title compound.

NMR (D$_2$O) δ(HOD=4.80 ppm): 1.17 (3H, d, J=7.2 Hz), 1.28 (3H, d, J=6.4 Hz), 2.98 (1H, m), 3.50 (3H, m), 3.86–4.04 (2H, m), 4.13–4.29 (2H, m), 5.12 (1H, d, J=15.7 Hz), 5.97 (1H, d, J=15.7 Hz), 7.54 (1H, d, J=4.4 Hz), 7.70 (1H, s), 7.96 (1H, d, J=4.4 Hz)

EXAMPLE 6

(1S,5R,6S)-6-[(1R)-1-hydroxyethyl]-2-(2-hydroxymethyl-3-methylimidazo[5,1-b]thiazolium-6-yl)methyl-1-methyl-1-carbapen-2-em-3-carboxylate (internal salt)

The same procedure as in Example 1 was repeated except that 135 mg of allyl (1S,5R,6S)-6-[(1R)-1- allyloxycarbonyloxyethyl]-2-hydroxymethyl-1-methyl-1-carbapen-2-em-3-carboxylate and 186 mg of 2-hydroxymethyl-3-methylimidazo[5,1-b]thiazole were used, thereby obtaining 9.3 mg of the title compound.

NMR (D$_2$O) δ(HOD=4.80 ppm): 1.12 (3H, d, J=7.4 Hz), 1.28 (3H, d, J=6.4 Hz), 2.49 (3H, m), 3.04 (1H, m), 3.49 (1H, dd, J=6.1 Hz, 3.0 Hz), 4.17–4.30 (2H, m), 4.80 (2H, s), 5.18 (1H, d, J=15.1 Hz), 5.82 (1H, d, J=15.1 Hz), 7.70 (1H, s), 9.36 (1H, s)

EXAMPLE 7

(1S,5R,6S)-6-[(1R)-1-hydroxyethyl]-2-(7-hydroxymethylimidazo[5,1-b]thiazolium-6-yl) methyl-1-methyl-1-carbapen-2-em-3-carboxylate (internal salt)

The same procedure as in Example 1 was repeated except that 149 mg of allyl (1S,5R,6S)-6-[(1R)-1-allyloxycarbonyloxyethyl]-2-hydroxymethyl-1-methyl-1-carbapen-2-em-3-carboxylate and 201 mg of 7-hydroxymethylimidazo[5,1-b]thiazole were used, thereby obtaining 1.4 mg of the title compound.

NMR (D$_2$O) δ(HOD=4.80 ppm): 1.14 (3H, d, J=7.4 Hz), 1.28 (3H, d, J=6.4 Hz), 2.96 (1H, m), 3.50 (1H, dd, J$_1$=6.1 Hz, J$_2$=2.9 Hz), 4.16–4.28 (2H, m), 4.90 (2H, s), 5.18 (1H, d, J=15.9 Hz), 5.88 (1H, d, J=15.9 Hz), 7.57 (1H, d, J=4.3 Hz), 7.93 (1H, d, J=4.3 Hz), 9.41 (1H, s)

EXAMPLE 8

(1S,5R,6S)-6-[(1R)-1-hydroxyethyl]-2-(2-(formylamino)methyl-3-methylimidazo[5,1-b]thiazolium-6-yl)methyl-1-methyl-1-carbapen-2-em-3-carboxylate (internal salt)

The same procedure as in Example 1 was repeated except that 91.3 mg of allyl (1S,5R,6S)-6-[(1R)-1-allyloxycarbonyloxyethyl]-2-hydroxymethyl-1-methyl-1-carbapen-2-em-3-carboxylate and 100 mg of 2-(formylamino)methyl-3-methylimidazo[5,1-b]thiazole were used, thereby obtaining 4 mg of the title compound.

NMR (D$_2$O) δ(HOD=4.80 ppm): 1.11 (3H, d, J=7.4 Hz), 1.27 (3H, d, J=6.3 Hz), 2.51 (3H, s), 2.98–3.08 (1H, m), 3.49 (1H, dd, J$_1$=6.0 Hz, J$_2$=3.0 Hz), 4.18–4.28 (2H, m), 4.58 (2H, s), 5.17 (1H, d, J=15.1 Hz), 5.80 (1H, d, J=15.1 Hz), 7.68 (1H, s), 8.19 (1H, s)

EXAMPLE 9

(1S,5R,6S)-6-[(1R)-1-hydroxyethyl]-2-(7-methylimidazo[5,1-b]thiazolium-6-yl)methyl-1-methyl-1-carbapen-2-em-3-carboxylate (internal salt)

The same procedure as in Example 1 was repeated except that 103 mg of allyl (1S,5R,6S)-6-[(1R)-1-allyloxycarbonyloxyethyl]-2-hydroxymethyl-1-methyl-1-carbapen-2-em-3-carboxylate and 117 mg of 7-methylimidazo[5,1-b]thiazole were used, thereby obtaining 7.8 mg of the title compound.

NMR (D$_2$O) δ(HOD=4.80 ppm): 1.15 (3H, d, J=7.4 Hz), 1.27 (3H, d, J=6.4 Hz), 2.45 (3H, s), 2.92 (1H, m), 3.50 (1H, dd, J$_1$=6.2 Hz, J$_2$=3.0 Hz), 4.14–4.30 (2H, m), 5.15 (1H, d, J=15.7 Hz), 5.84 (1H, d, J=15.7 Hz), 7.53 (1H, d, J=4.3 Hz), 7.87 (1H, d, J=4.3 Hz)

EXAMPLE 10

(1S,5R,6S)-6-[(1R)-1-hydroxyethyl]-2-(3-methylimidazo[5,1-b]thiazolium-6-yl)methyl-1-methyl-1-carbapen-2-em-3-carboxylate (internal salt)

The same procedure as in Example 1 was repeated except that 187 mg of allyl (1S,5R,6S)-6-[(1R)-1-allyloxycarbonyloxyethyl]-2-hydroxymethyl-1-methyl-1-carbapen-2-em-3-carboxylate and 212 mg of 3-methylimidazo[5,1-b]thiazole were used, thereby obtaining 42.4 mg of the title compound.

NMR (D$_2$O) δ(HOD=4.80 ppm): 1.09 (3H, d, J=7.4 Hz), 1.23 (3H, d, J=6.3 Hz), 2.47 (3H, s), 3.01 (1H, m), 3.45 (1H, dd, J$_1$=6.1 Hz, J$_2$=3.0 Hz), 4.14–4.23 (2H, m), 5.15 (1H, d, J=15.1 Hz), 5.81 (1H, d, J=15.1 Hz), 7.11 (1H, s), 7.68 (1H, s), 9.35 (1H, s)

EXAMPLE 11

(1S,5R,6S)-6-[(1R)-1-hydroxyethyl]-2-[3-(2-hydroxyethyl)imidazo[5,1-b]thiazolium-6-yl]methyl-1-methyl-1-carbapen-2-em-3-carboxylate (internal salt)

The same procedure as in Example 1 was repeated except that 87 mg of allyl (1S,5R,6S)-6-[(1R)-1-allyloxycarbonyloxyethyl]-2-hydroxymethyl-1-methyl-1-carbapen-2-em-3-carboxylate and 100 mg of 3-(2-hydroxyethyl)imidazo[5,1-b]thiazole were used, thereby obtaining 25 mg of the title compound.

NMR (D$_2$O) δ(HOD=4.80 ppm): 1.10 (3H, d), 1.26 (3H, d), 3.02 (1H, m), 3.13 (2H, t), 3.47 (1H, dd), 3.98 (2H, t), 4.15–4.30 (2H, m), 5.18 (1H, d), 5.80 (1H, d), 7.26 (1H, s), 7.72 (1H, s), 9.43 (1H, s)

EXAMPLE 12

(1S,5R,6S)-6-[(1R)-1-hydroxyethyl]-2-(3-carbamoylmethylimidazo[5,1-b]thiazolium-6-yl) methyl-1-methyl-1-carbapen-2-em-3-carboxylate (internal salt)

The same procedure as in Example 1 was repeated except that 95 mg of allyl (1S,5R,6S)-6-[(1R)-1-allyloxycarbonyloxyethyl]-2-hydroxymethyl-1-methyl-1-carbapen-2-em-3-carboxylate and 70 mg of 3-carbamoylmethylimidazo[5,1-b]thiazole were used, thereby obtaining 4.1 mg of the title compound.

NMR (D$_2$O) δ(HOD=4.80 ppm): 1.09 (3H, d), 1.27 (3H, d), 3.03 (1H, m), 3.49 (1H, dd), 4.06 (2H, s), 4.15–4.30 (2H, m), 5.23 (1H, d), 5.79 (1H, d), 7.43 (1H, s), 7.77 (1H, s), 9.43 (1H, s)

EXAMPLE 13

(1S,5R,6S)-6-[(1R)-1-hydroxyethyl]-2-[3-(2-carbamoyloxyethyl)imidazo[5,1-b]thiazolium-6-yl] methyl-1-methyl-1-carbapen-2-em-3-carboxylate (internal salt)

The same procedure as in Example 1 was repeated except that 95 mg of allyl (1S,5R,6S)-6-[(1R)-1-allyloxycarbonyloxyethyl]-2-hydroxymethyl-1-methyl-1-carbapen-2-em-3-carboxylate and 110 mg of 3-(2-carbamoyloxyethyl)imidazo[5,1-b]thiazole were used, thereby obtaining 26.9 mg of the title compound.

NMR (D$_2$O) δ(HOD=4.80 ppm): 1.11 (3H, d), 1.27 (3H, d), 3.04 (1H, m), 3.27 (2H, t), 3.48 (1H, dd), 4.15–4.30 (2H, m), 4.42 (2H, t), 5.20 (1H, d), 5.81 (1H, d), 7.32 (1H, s), 7.73 (1H, s), 9.48 (1H, s)

EXAMPLE 14

(1S,5R,6S)-6-[(1R)-1-hydroxyethyl]-2-[3-(aminosulfonyl)aminomethylimidazo[5,1-b]thiazolium-6-yl]methyl-1-methyl-1-carbapen-2-em-3-carboxylate (internal salt)

The same procedure as in Example 1 was repeated except that 91.3 mg of allyl (1S,5R,6S)-6-[(1R)-1- allyloxycarbonyloxyethyl]-2-hydroxymethyl-1-methyl-1-carbapen-2-em-3-carboxylate and 145 mg of 3-[N-allyloxycarbonyl-N-(aminosulfonyl)amino]methyl imidazo[5,1-b]thiazole were used, thereby obtaining 2.8 mg of the title compound.

NMR (D$_2$O) δ(HOD=4.80 ppm): 1.08 (3H, d, J=7.4 Hz), 1.25 (3H, d, J=6.3 Hz), 3.00–3.11 (1H, m), 3.48 (1H, dd, J$_1$=6.0 Hz, J$_2$=3.0 Hz), 4.18–4.27 (2H, m), 4.55 (2H, s), 5.24 (1H, d, J=15.0 Hz), 5.74 (1H, d, J=15.0 Hz), 7.51 (1H, s), 7.76 (1H, s)

EXAMPLE 15

(1S,5R,6S)-6-[(1R)-1-hydroxyethyl]-2-(3-ureidomethylimidazo[5,1-b]thiazolium-6-yl)methyl-1-methyl-1-carbapen-2-em-3-carboxylate (internal salt)

The same procedure as in Example 1 was repeated except that 135 mg of allyl (1S,5R,6S)-6-[(1R)-1-allyloxycarbonyloxyethyl]-2-hydroxymethyl-1-methyl-1-carbapen-2-em-3-carboxylate and 87 mg of 3-ureidomethylimidazo[5,1-b]thiazole were used, thereby obtaining 6 mg of the title compound.

NMR (D$_2$O) δ(HOD=4.80 ppm): 1.90 (3H, d, J=7.0 Hz), 1.26 (3H, d, J=6.4 Hz), 3.05 (1H, m), 3.47 (1H, m), 4.21 (1H, m), 4.21 (1H, m), 4.80 (2H, s), 5.21 (1H, d, J=15.1 Hz), 5.75 (1H, d, J=15.1 Hz), 7.38 (1H, s), 7.75 (1H, s), 9.37 (1H, s)

EXAMPLE 16

(1S,5R,6S)-6-[(1R)-1-hydroxyethyl]-2-[3-methyl-2-(aminosulfonyl)aminomethylimidazo[5,1-b]thiazolium- 6-yl)methyl-1-methyl-1-carbapen-2-em-3-carboxylate (internal salt)

The same procedure as in Example 1 was repeated except that in a deprotective reaction, two catalysts, i.e., 23.4 mg of tris(dibenzylideneacetone)dipalladium and 59.1 mg of tetrakis(triphenylphosphine)palladium were used, 0.14 ml of aniline was used as a trapping agent, and 110.3 mg of allyl (1S,5R,6S)-6-[(1R)-1-allyloxycarbonyloxyethyl]-2-hydroxymethyl-1-methyl-1-carbapen-2-em-3-carboxylate and 196 mg of 2-[N-allyloxycarbonyl-N-(aminosulfonyl)amino]methyl-3-methylimidazo[5,1-b]thiazole were used, thereby obtaining 14.2 mg of the title compound.

NMR (D$_2$O) δ(HOD=4.80 ppm): 1.12 (3H, d, J=7.2 Hz), 1.27 (3H, d, J=6.4 Hz), 2.50 (3H, s), 2.98–3.09 (1H, m), 3.49 (1H, dd, J$_1$=6.1 Hz, J$_2$=3.0 Hz), 4.18–4.29 (2H, m), 4.45 (2H, s), 5.17 (1H, d, J=15.1 Hz), 5.81 (1H, d, J=15.1 Hz), 7.70 (1H, s)

EXAMPLE 17

(1S,5R,6S)-6-[(1R)-1-hydroxyethyl]-2-[3-(formylamino)methylimidazo[5,1-b]thiazolium-6-yl]methyl-1-methyl-1-carbapen-2-em-3-carboxylate (internal salt)

The same procedure as in Example 1 was repeated except that 88 mg of allyl (1S,5R,6S)-6-[(1R)-1-allyloxycarbonyloxyethyl]-2-hydroxymethyl-1-methyl-1-carbapen-2-em-3-carboxylate and 70 mg of 3-(formylamino)methylimidazo[5,1-b]thiazole were used, thereby obtaining 1.2 mg of the title compound.

NMR (D$_2$O) δ(HOD=4.80 ppm): 1.12 (3H, d, J=7.2 Hz), 1.29 (3H, d, J=6.4 Hz), 3.07 (1H, m), 3.51 (1H, dd, J=6.1 Hz, J$_2$=3.0 Hz), 4.20–4.30 (2H, m), 4.72 (2H, s), 5.23 (1H, d, J=15.2 Hz), 5.81 (1H, d, J=15.2 Hz), 7.48 (1H, s), 7.78 (1H, s), 8.25 (1H, s), 9.37 (1H, s)

EXAMPLE 18

(1S,5R,6S)-6-[(1R)-1-hydroxyethyl]-2-[3-[N-(2-aminoethyl)carbamoyl]imidazo[5,1-b]thiazolium-6-yl]methyl-1-methyl-1-carbapen-2-em-3-carboxylate (internal salt)

The same procedure as in Example 1 was repeated except that dimedone was used as a trapping agent in a deprotective reaction, and 145 mg of allyl (1S,5R,6S)-6-[(1R)-1-allyloxycarbonyloxyethyl]-2-hydroxymethyl-1-methyl-1-carbapen-2-em-3-carboxylate and 340 mg of 3-[N-(2-allyloxycarbonylaminoethyl)carbamoyl]imidazo[5,1-b]thiazole were used, thereby obtaining 9.3 mg of the title compound.

NMR (D$_2$O) δ(HOD=4.80 ppm): 1.13 (3H, d, J=7.4 Hz), 1.29 (3H, d, J=6.4 Hz), 3.09 (1H, m), 3.31 (2H, m), 3.51 (1H, dd, J$_1$=6.0 Hz, J$_2$=2.9 Hz), 3.77 (2H, m), 4.20–4.30 (2H, m), 5.27 (1H, d, J=15.1 Hz), 5.82 (1H, d, J=15.1 Hz), 7.86 (1H, s), 8.37 (1H, s), 9.78 (1H, s)

Preparation 10

2-[(N,N-dimethylaminosulfonyl)amino]methyl-3-methylimidazo[5,1-b]thiazole

A 780 mg portion of 4-N,N-dimethylaminopyridine was added to 10 ml of a dichloromethane solution containing 534 mg of 2-aminomethyl-3-methylimidazo[5,1-b]thiazole, and 0.69 ml of dimethylcarbamoyl chloride was further added thereto, followed by stirring at room temperature for 1 hour. Afterward, the solution was heated under reflux for 260 minutes. Moreover, 780 mg of 4-N,N-dimethylaminopyridine and 0.69 ml of dimethylcarbamoyl chloride were added, and the solution was then heated under reflux for 4 hours. After dilution with 500 ml of dichloromethane, the solution was washed twice with distilled water and then dried over anhydrous magnesium sulfate, and the solvent was evaporated under reduced pressure. The resulting residue was purified by Cephadex LH-20 to obtain 413.2 mg of the title compound as a light yellowishgreen solid.

NMR (CDCl$_3$) δ: 2.42 (2H, s), 2.80 (3H, s), 4.27 (2H, d, J=5.8 Hz), 4.64 (1H, br.t), 7.08 (1H, s), 7.86 (1H, s)

MS (EI): 274 (M$^+$)

Preparation 11

3-allyloxycarbonylaminoimidazo[5,1-b]thiazole a) 2-(N-t-butoxycarbonylamino)methylthiazol-4-carboxylic acid A 20 ml portion of a 2N aqueous sodium hydroxide solution was added to 100 ml of an ethanol solution containing 5.727 g of ethyl 2-(N-t-butoxycarbonylamino) methylthiazol-4-carboxylate, and the mixture was then stirred at room temperature for 45 minutes. After adjustment to pH 5 with 2N hydrochloric acid, the solvent was evaporated under reduced pressure. Further, the solution was dissolved in 300 ml of ethanol under heating, and after the removal of a salt by filtration, the solvent was evaporated under reduced pressure to obtain 4.228 g of 2-(N-t-butoxycarbonylamino)methylthiazol-4-carboxylic acid as a milky white solid.

NMR (DMSO-d$_6$) δ: 1.41 (9H, s), 4.39 (2H, d, J=6.0 Hz), 7.86 (1H, br.t, J=6.0 Hz), 8.34 (1H, s), 13.0 (1H, br.s)

MS (EI): 258 (M$^+$)

b) 4-allyloxycarbonylamino-2-(N-t-butoxycarbonylamino)methylthiazole

To a mixed solution obtained by adding 2.74 ml of triethylamine to 210 ml of a dry THF solution containing 4.228 g of 2-(N-t-butoxycarbonylamino)methylthiazol-4-carboxylic acid, 1.94 ml of ethyl chloroformate was added dropwise at −12° C. over 2 minutes under stirring, and the mixture was then stirred at the same temperature for 120 minutes. Further, 50 ml of a cold aqueous solution containing 1.316 g of sodium azide was added thereto, followed by stirring at 2° C. for 140 minutes. Afterward, the reaction solution was concentrated under reduced pressure until the amount of the solution had been halved. The solution was diluted with 300 ml of ethyl acetate, washed with water, and then dried over anhydrous magnesium sulfate. The solvent was evaporated under reduced pressure to obtain a colorless powder, and this powder was then dissolved in 200 ml of dry toluene. Then, 3.34 ml of dry allyl alcohol was further added, and the mixed solution was heated at an oil temperature of 90° C. for 3 hours with stirring. Afterward, the solvent was evaporated under reduced pressure to obtain an oil, and this oil was then dissolved in 400 ml of ethyl acetate. The solution was washed with water and then dried over anhydrous magnesium sulfate, and the solvent was evaporated under reduced pressure to obtain 4.791 g of 4-allyloxycarbonylamino-2-(N-t-butoxycarbonylamino)methylthiazole as an orange oil.

NMR (DMSO-d$_6$) δ: 1.46 (9H, s), 4.54 (2H, d, J=5.8 Hz), 4.70 (2H, d, J=5.5 Hz), 5.25–5.40 (2+1H, m+br.s), 5.90–6.04 (1H, m), 7.20 (1H, br.s), 8.02 (1H, br.s)

MS (EI): 313 (M$^+$)

c) 4-allyloxycarbonylamino-2-(formylamino)methylthiazole

A 24.0 ml portion of trifluoroacetic acid was added to 4.791 g of 4-allyloxycarbonylamino-2-(N-t-butoxycarbonylamino)methylthiazole, and the mixture was then stirred at room temperature for 50 minutes. The reagent was evaporated under reduced pressure to obtain a dark red oil, and this oil was then dissolved in 50 ml of dichloromethane and 50 ml of distilled water, followed by adjustment to pH 5 with sodium bicarbonate. A mixed solution of 7.2 ml of anhydrous acetic acid and 14.4 ml of formic acid was added dropwise to the solution at room temperature over 15 minutes under vigorous stirring. After the pH of the solution was adjusted to 5 again, it was stirred for 2.5 hours. Furthermore, a mixed solution of 2.9 ml of anhydrous acetic acid and 5.8 ml of formic acid was added dropwise to the solution over 25 minutes, and adjustment to pH 5 was carried out with sodium bicarbonate again, followed by stirring for 2.5 hours. After the addition of 250 ml of dichloromethane and sufficient shaking, the resulting precipitate was collected by filtration, and from the filtrate, the organic layer was separated, dried (magnesium sulfate), and then filtered. This filtrate was combined with a liquid eluted from the precipitate with a dichloromethane-methanol mixture solvent, and the solvent was then evaporated under reduced pressure to obtain 3.408 g of 4-allyloxycarbonylamino-2-(formylamino)methylthiazole as a light orange powder.

NMR (CD$_3$COCD$_3$) δ: 4.63–4.68 (4H, m), 5.22 (1H, ddd, J$_1$=10.5 Hz, J$_2$=3.0 Hz, J$_3$=1.4 Hz), 5.38 (1H, dq, J$_1$=17.3 Hz, J$_2$=1.7 Hz), 5.93–6.06 (1H, m), 7.21 (1H, s), 7.94 (1H, br.s), 8.30 (1H, s), 9.35 (1H, br.s).

MS (EI): 241 (M$^+$)

d) 3-allyloxycarbonylaminoimidazo[5,1-b]thiazole

A 6.4 ml portion of phosphorus oxychloride was added to a suspension obtained by adding 17 ml of dry toluene to 3.408 g of 4-allyloxycarbonylamino-2-(formylamino)methylthiazole, and the mixture was then stirred at an oil temperature of 100° C. for 45 minutes. The solvent was evaporated under reduced pressure, and to the resulting residue, 200 ml of dichloromethane and 100 ml of 0.1N sodium hydroxide were added. The solution was adjusted to pH 8.0 with a 2N aqueous sodium hydroxide solution under stirring. After the removal of insolubles by filtration, the organic layer was separated from the filtrate, and it was combined with a liquid extracted from the aqueous layer with 100 ml of dichloromethane, dried (magnesium sulfate), and then filtered. Further, the solvent was evaporated under reduced pressure to obtain an ocherous powder, and this powder was then purified by a silica gel column chromatograph to obtain 2.390 g of the title compound as a light orange powder.

NMR (CD$_3$COCD$_3$) δ: 4.69–4.72 (2H, m), 5.25 (1H, ddd, J$_1$=10.5 Hz, J$_2$=2.8 Hz, J$_3$=1.4 Hz), 5.38 (1H, dq, J$_1$=17.2 Hz, J$_2$=1.6 Hz), 5.95–6.08 (1H, m), 6.89 (1H, s), 7.04 (1H, s), 8.20 (1H, s), 9.43 (1H, br.s).

MS (EI): 223 (M$^+$)

Preparation 12

3-(N-allyloxycarbonyl-N-methyl)aminoimidazo[5,1-b]thiazole

A 0.30 ml portion of a 1.68M n-butyl lithium/n-hexane solution was added dropwise to 2.5 ml of an anhydrous THF solution containing 111.6 mg of 3-allyloxycarbonylaminoimidazo[5,1-b]thiazole at 5° C. under stirring over 3 minutes, and the mixture was then stirred at room temperature for 5 minutes. Further, 0.040 ml of methyl iodide was added thereto, and after stirring for 10 minutes, 0.50 ml of dry DMF was added to dissolve a precipitate, followed by further stirring for 190 minutes. The reaction solution was diluted with 20 ml of ethyl acetate, washed with a 1/15M phosphoric acid buffer (pH 7.0), dried over anhydrous magnesium sulfate and anhydrous potassium carbonate, and then filtered, and the solvent was then evaporated under reduced pressure. The resulting residue was purified by Cephadex LH-20 to obtain 94.0 mg of the title compound as a milky white powder.

NMR (CDCl$_3$) δ: 3.38 (3H, s), 4.64 (2H, br.d, J=5.3 Hz), 5.20 (2H, br.d, J=11.1 Hz), 5.79–5.93 (1H, m), 6.65 (1H, s), 7.10 (1H, s), 7.82 (1H, s)

MS (EI): 237 (M$^+$)

Preparation 13

3-methoxycarbonylaminoimidazo[5,1-b]thiazole a) 2-(N-t-butoxycarbonylamino)methyl-4-methoxycarbonylaminothiazole To 50 ml of a dry DMF solution containing 2.583 g of 2-(N-t-butoxycarbonylamino)methylthiazol-4-carboxylic acid, 1.53 ml of triethylamine and 2.37 ml of azido diphenylphosphate were added. Immediately after the mixed solution was then heated at an oil temperature of 100° C. for 10 minutes under stirring, it was cooled on ice to return its temperature to room temperature. Further, 2.0 ml of dry methanol was added, and after heating at an oil temperature of 80° C. for 30 minutes, the solvent was evaporated under reduced pressure. The residue was diluted with 100 ml of ethyl acetate and then washed with a 15% aqueous potassium carbonate solution, and the separated organic layer was then combined with a liquid extracted from the aqueous layer with 50 ml of ethyl acetate. Furthermore, the solution was washed with distilled water and a saturated saline solution in succession, and then dried over anhydrous magnesium sulfate. Afterward, the solvent was evaporated under reduced pressure to obtain an oil, and this oil was then purified by a silica gel column chromatograph to obtain 817 mg of 2-(N-t-butoxycarbonylamino)methyl-4-methoxycarbonylaminothiazole as a slightly red crystal.

NMR (CDCl$_3$) δ: 1.47 (9H, s), 3.81 (3H, s), 4.53 (2H, br.d, J=5.7 Hz), 5.28 (1H, br.s), 7.20 (1H, br.s), 7.89 (1H, br.s)

MS (EI): 287 (M$^+$)

b) 2-(formylamino)methyl-4-methoxycarbonylaminothiazole

A 3.9 ml portion of trifluoroacetic acid was added to 776 mg of 2-(N-t-butoxycarbonylamino)methyl-4-methoxycarbonylaminothiazole, followed by stirring at room temperature for 50 minutes. The reagent was evaporated under reduced pressure to obtain a light brown solid, and this solid was then dissolved in 13.5 ml of dichloromethane and 10 ml of a 15% aqueous potassium carbonate solution to adjust the pH of the solution to 10.0. Further, a mixed solution of 2.55 ml of anhydrous acetic acid and 1.27 ml of formic acid was added dropwise over 10 minutes under ice-cooling with vigorous stirring. After adjustment to pH 6 with potassium carbonate, the ice bath was removed, and the solution was then stirred for 30 minutes. After the addition of 100 ml of dichloromethane and 20 ml of distilled water as well as sufficient shaking, the organic layer was separated. After the pH of the aqueous layer was adjusted to 11 with potassium carbonate, extraction was carried out twice with 100 ml of dichloromethane, and the extract was then combined with the above organic layer. Further, the solution was dried (anhydrous magnesium sulfate and anhydrous potassium carbonate), and then filtered. The solvent was then evaporated under reduced pressure to obtain 581 mg of 2-(formylamino)methyl-4-methoxycarbonylaminothiazole as a light yellow powder.

NMR (CD$_3$COCD$_3$) δ: 3.73 (3H, s), 4.64 (2H, d, J=6.3 Hz), 7.20 (1H, s), 7.91 (1H, br.s), 8.29 (1H, s), 9.24 (1H, br.s).

MS (methane-CI): 216 (M$^+$+1)

c) 3-methoxycarbonylaminoimidazo[5,1-b]thiazole

A 1.17 ml portion of phosphorus oxychloride was added to a suspension formed by adding 2.8 ml of dry toluene to 560 mg of 2-(formylamino)methyl-4-methoxycarbonylaminothiazole, and the mixture was then stirred at an oil temperature of 100° C. for 45 minutes. Then, the solvent was evaporated under reduced pressure, and 30 ml of dichloromethane and 10 ml of a 15% aqueous potassium carbonate solution were then added to the resulting residue to adjust the solution to pH 9.5. The organic layer was separated, and the aqueous layer was then salted out with sodium chloride. Afterward, extraction was carried out three times with 30 ml of dichloromethane, and the extract was then combined with the above organic layer. The solution was dried (magnesium sulfate), and then filtered. Further, the solvent was evaporated under reduced pressure to obtain a milky white powder, and this powder was then purified by a silica gel column chromatograph to obtain 417.5 mg of the title compound as a colorless powder.

NMR (CD$_3$COCD$_3$) δ: 3.79 (3H, s), 6.88 (1H, s), 7.04 (1H, s), 8.20 (1H, s), 9.37 (1H, br.s)

MS (methane-CI): 198 (M$^+$+1)

Preparation 14

3-[(N-allyloxycarbonyl-N-methylamino)sulfonyl] aminomethylimidazo[5,1-b]thiazole and 3-[N-(N-allyloxycarbonyl-N-methylamino)sulfonyl-N-methylaminomethylimidazo[5,1-b]thiazole a) 3-[(N-allyloxycarbonylamino)sulfonylamino]methyl imidazo[5,1-b]thiazole Under an argon atmosphere, 0.68 ml of allyl alcohol was added dropwise to a dry dichloromethane solution containing 0.87 ml of chlorosulfonyl isocyanate at −43° C. with stirring, and the mixture was then stirred at −43 to −37° C. for 30 minutes. This mixed solution was added dropwise to 50 ml of a dry dichloromethane solution containing 766 mg of 3-aminomethylimidazo[5,1-b]thiazole and 1.40 ml of triethylamine at −60° C. under an argon atmosphere, followed by stirring at the same temperature for 1.5 hours. After the addition of distilled water, the solution was adjusted to pH 6.0 with a 15% aqueous potassium carbonate solution and 2N hydrochloric acid, and after salting-out, extraction was carried out five times with ethyl acetate. After the organic layer was dried over anhydrous magnesium sulfate, the solvent was evaporated under reduced pressure. The resulting residue was separated by a silica gel column chromatograph, and then recrystallized from ethanol-diethyl ether to obtain 1135 mg of 3-[(N-allyloxycarbonylamino) sulfonyl]aminomethylimidazo[5,1-b]thiazole as a milky white powder.

NMR (DMSO-d$_6$) δ: 4.34 (2H, br.d, J=6.1 Hz), 4.49 (2H, br.dt, J=5.5 Hz), 5.21–5.25 (1H, m), 5.28–5.36 (1H, m), 5.82–5.95 (1H, m), 7.06 (1H, d, J=0.6 Hz), 7.07 (1H, s), 8.22 (1H, d, J=0.6 Hz), 8.60 (1H, br.t, J=5.9 Hz), 11.5 (1H, br.s)

MS (SIMS): 317 (M$^+$+1)

b) 3-[(N-allyloxycarbonyl-N-methylamino)sulfonyl amino]methylimidazo[5,1-b]thiazole and 3-[N-(N-allyloxycarbonyl-N-methylamino)sulfonyl-N-methylamino]methylimidazo[5,1-b]thiazole 0.96 ml of a 1M lithium bis(trimethylsilyl)amide/THF solution was added dropwise to 4.6 ml of a dry DMF solution containing 290 mg of 3-(N-allyloxycarbonylamino)sulfonylamino]methylimidazo[5,1-b]thiazole at −7 to −5° C. under stirring over 3 minutes, and the mixture was then stirred at the same temperature for 40 minutes. Further, 0.077 ml of methyl iodide was added, and the solution was then stirred at −4 to +6° C. for 200 minutes. After diluted with 50 ml of ethyl acetate, the solution was washed with 5% sodium bicarbonate and a saturated saline solution in succession, and the organic layer was dried over anhydrous magnesium sulfate and the solvent was then evaporated under reduced pressure. The resulting residue was separated by a silica gel column chromatograph to obtain 48.9 mg of 3-[N-(N-allyloxycarbonyl-N-methylamino)sulfonyl-N-methylamino]methylimidazo[5,-b]thiazole as a light yellow powder.

NMR (CDCl$_3$) δ: 2.82 (3H, s), 3.38 (3H, s), 4.63 (2H, s), 4.72–4.75 (2H, m), 5.32–5.38 (2H, m), 5.91–6.04 (1H, m), 6.75 (1H, s), 7.14 (1H, s), 8.21 (1H, s)

MS (EI): 344 (M$^+$)

In addition, 98.5 mg of 3-[(N-allyloxycarbonyl-N-methylamino)sulfonylamino]methylimidazo[5,1-b]thiazole which was a highly polar component was obtained as a milky white powder.

NMR (CDCl$_3$) δ: 3.24 (3H, s), 4.37 (2H, s), 4.60 (2H, dt, J$_1$=5.8 Hz, J$_2$=1.3 Hz), 5.28–5.39 (2H, m), 5.82–5.95 (1H, m), 6.80 (1H, s), 7.12 (1H, s), 8.09 (1H, s)

MS (SIMS): 331 (M$^+$+1)

Preparation 15

3-(N-methoxycarbonylamino)sulfonylaminomethyl imidazo[5,1-b]thiazole

A 0.081 ml potion of dry methanol was added dropwise to 0.35 ml of a dry dichloromethane solution containing 0.175 ml of chlorosulfonyl isocyanate at a bath temperature of −55° C. under stirring, and the mixture was then stirred for 20 minutes. Then, the precipitate was dissolved in 2.0 ml of dry dichloromethane, and this mixed solution was added dropwise to 10 ml of a dry dichloromethane solution containing 153 mg of 3-aminomethylimidazo[5,1-b]thiazole and 0.28 ml of triethylamine at an internal temperature of −47° C. over 2 minutes, and the mixture was then stirred at −47 to −35° C. for 60 minutes. After the addition of 10 ml of a 1/15M phosphoric acid buffer, the solution was adjusted to pH 7.5 with 5% sodium bicarbonate, and after salting-out, extraction was carried out five times with 30 ml of dichloromethane. Further, the aqueous layer was adjusted to pH 6 with 1N hydrochloric acid, and extraction was then carried out five times with 30 ml of ethyl acetate. The extract was combined with the above dichloromethane extract. Afterward, the solution was dried over anhydrous magnesium sulfate, and the solvent was then evaporated under reduced pressure. The resulting residue was recrystallized from methanol to obtain 87.4 mg of the title compound as a light yellow crystal.

NMR (DMSO-d$_6$) δ: 3.56 (3H, s), 4.33 (2H, br.d, J=4.7 Hz), 7.06 (1H, s), 7.07 (1H, s), 8.22 (1H, s), 8.53 (1H, br.s), 11.4 (1H, br.s)

MS (FD): 290 (M$^+$)

Preparation 16

3-(methanesulfonylamino)methylimidazo[5,1-b]thiazole

A 204 mg potion of 3-aminomethylimidazo[5,-b]thiazole was dissolved in 4 ml of dichloromethane, and 0.255 ml of N,N-diisopropylethylamine and 0.114 ml of methanesulfonyl chloride were further added thereto at −10° C., followed by stirring for 10 minutes. To the reaction solution, 3 ml of dichloromethane and 3 ml of an aqueous semi-saturated sodium hydrogencarbonate solution were added, and the resulting crystal was collected by filtration and then washed with dichloromethane and water to obtain 275 mg of the title compound.

NMR (DMSO-d$_6$) δ: 2.95 (3H, s), 4.39 (2H, d, J=5.9 Hz), 7.07 (1H, s), 7.13 (1H, s), 7.81 (1H, t, J=5.9 Hz), 8.21 (1H, s)

Preparation 17

3-(N,N-dimethylamino)sulfonylaminomethylimidazo[5,1-b]thiazole

A 210 mg potion of 3-aminomethylimidazo[5,1-b]thiazole was dissolved in 4 ml of dichloromethane, and 202 mg of 4-dimethylaminopyridine and 0.179 ml of N,N-dimethylsulfamoyl chloride were further added, followed by stirring for 2.5 hours. Then, to the reaction solution, an aqueous semi-saturated sodium hydrogencarbonate solution were added, and extraction was then carried out three times with dichloromethane. The organic layer was dried over anhydrous magnesium sulfate and then filtered, and the solvent was then evaporated under reduced pressure. Afterward, the resulting residue was purified by a silica gel column chromatograph to obtain 177 mg of the title compound.

NMR (DMSO-d$_6$) δ: 2.63 (6H, s), 4.33 (2H, d, J=6.0 Hz), 7.07 (1H, s), 7.12 (1H, s), 7.92 (1H, t, J=6.0 Hz), 8.22 (1H, s)

Preparation 18

3-(aminosulfonyl)aminomethylimidazo[5,1-b]thiazole

A 770 mg potin of 3-aminomethylimidazo[5,1-b]thiazole was dissolved in 15 ml of DMF, and 4.78 ml of N,N-diisopropylethylamine and 1.04 g of sulfamoyl chloride were further added at −60° C., followed by stirring at −30 to −20° C. for 4 hours. The reaction solution was concentrated under reduced pressure and then dissolved in 30 ml of water, and the solution was adjusted to pH 7.5 with an aqueous sodium hydrogencarbonate solution. After purification by Diaion HP-20 Resin, crystallization was carried out from methanol to obtain 636 mg of the title compound.

NMR (DMSO-d$_6$) δ: 4.25 (2H, d, J=6.3 Hz), 6.85 (2H, s), 7.06 (1H, s), 7.09 (1H, s), 7.31 (1H, t, J=6.3 Hz), 8.23 (1H, s)

Preparation 19

5-(aminosulfonyl)aminomethylimidazo[5,1-b]thiazole

The same procedure as in Preparation 18 was repeated except that 112 mg of 5-aminomethylimidazo[5,1-b]thiazole was used, thereby obtaining 120 mg of the title compound.

NMR (DMSO-d$_6$) δ: 4.32 (2H, d, J=6.4 Hz), 6.77 (2H, s), 6.95 (1H, s), 7.20 (1H, t, J=6.4 Hz), 7.24 (1H, t, J=4.2 Hz), 7.83 (1H, d, J=4.2 Hz)

Preparation 20

7-(aminosulfonyl)aminomethylimidazo[5,1-b]thiazole

The same procedure as in Preparation 18 was repeated except that 396 mg of 7-aminomethylimidazo[5,1-b]thiazole was used, thereby obtaining 136 mg of the title compound.

NMR (DMSO-d$_6$) δ: 4.11 (2H, d, J=6.4 Hz), 6.60 (2H, s), 6.94 (1H, t, J=6.4 Hz), 7.17 (1H, t, J=4.1 Hz), 7.82 (1H, d, J=4.1 Hz), 8.11 (1H, s)

Preparation 21

3-(N-aminosulfonyl-N-methylamino)methylimidazo [5,1-b]thiazole a) 3-(N-methylamino)methylimidazo[5,1-b]thiazole To 0.5 ml of methanol containing 120 mg of methylamine hydrochloride, 46 mg of potassium hydroxide and 90 mg of 3-formylimidazo[5,1-b]thiazole were added, followed by stirring at room temperature for 6.5 hours. Further, 64 mg of sodium boron cyanohydride was added thereto, and the mixture was then stirred at room temperature for 17 hours. Afterward, the solvent was evaporated under reduced pressure. To the resulting residue, 20 ml of water was added, and extraction was then carried out twice with dichloromethane.

The organic layer was dried over anhydrous magnesium sulfate and then filtered, and the solvent was then evaporated under reduced pressure to obtain 47.6 mg of 3-(N-methylamino)methylimidazo[5,1-b]thiazole.

NMR (CDCl$_3$) δ: 2.48 (3H, s), 3.91 (2H, s), 6.62 (1H, s), 7.08 (1H, s), 8.11 (1H, s)

b) 3-(N-aminosulfonyl-N-methylamino)methylimidazo[5,1-b]thiazole

A 47 mg potion of 3-(N-methylamino)methylimidazo[5,1-b]thiazole was dissolved in 1 ml of DMF, and 0.305 ml of N,N-diisopropylethylamine and 100 mg of sulfamoyl chloride were further added at −45° C., followed by stirring for 8 hours, while the solution was heated up to room temperature. Then, the reaction solution was concentrated under reduced pressure, and 10 ml of water and an aqueous sodium hydrogencarbonate solution were then added to adjust the solution to pH 9.0. Afterward, extraction was carried out four times with dichloromethane. The organic layer was dried over anhydrous magnesium sulfate and then filtered, and the solvent was evaporated under reduced pressure. The resulting residue was purified by a silica gel column chromatograph to obtain 37.4 mg of the title compound.

NMR (CDCl$_3$) δ: 2.78 (3H, s), 4.40 (2H, s), 6.77 (1H, s), 7.10 (1H, s), 8.22 (1H, s)

Preparation 22

3-(N-allyloxycarbonyl-N-methylamino)methylimidazo[5,1-b]thiazole

To 207 mg of a mixture of 3-(N-methylamino)methylimidazo[5,1-b]thiazole and 3-hydroxymethylimidazo[5,1-b]thiazole in a ratio of about 1:1, 10 ml of dichloromethane and 3 ml of water were added, and then 0.092 ml of allyl chloroformate was added thereto under ice-cooling. The mixture was stirred for 30 minutes under ice-cooling, while the aqueous layer was adjusted to pH 8.5 by adding a sodium hydrogencarbonate solution. The organic layer was separated, and the aqueous layer was extracted with dichloromethane. The combined organic layer was dried over anhydrous magnesium sulfate and then filtered, and the solvent was evaporated under reduced pressure. The resulting residue was purified by a silica gel column chromatograph to obtain 73.6 mg of the title compound.

NMR (CDCl$_3$) δ: 2.90 (3H, s), 4.65 (4H, m), 5.20–5.40 (2H, m), 5.87–6.05 (1H, m), 6.69 (1H, s), 7.11 (1H, s), 8.14 (1H, s)

Preparation 23

3-(N-formyl-N-methylamino)methylimidazo[5,1-b]thiazole

A mixed solution of 0.25 ml of anhydrous acetic acid and 0.50 ml of formic acid which had been beforehand reacted with each other at 50° C. for 5 minutes was added to 6 ml of a dichloromethane solution containing 294 mg of 3-(N-methylamino)methylimidazo[5,1-b]thiazole under ice-cooling, followed by stirring at the same temperature for 30 minutes. Then, water was added to the reaction solution, and the solution was then alkalified with anhydrous potassium carbonate under stirring, followed by extraction three times with dichloromethane. The organic layer was dried over anhydrous potassium carbonate and then filtered, and the solvent was evaporated under reduced pressure. The resulting residue was purified by a silica gel column chromatograph to obtain 174 mg of the title compound.

NMR (CDCl$_3$) δ: 2.91 (0.6H, s), 2.93 (2.4H, s), 4.58 (0.4H, s), 4.69 (1.6H, s), 6.77 (1H, s), 7.10 (0.8H, s), 7.30 (0.2H, s), 7.88 (0.2H, s), 8.09 (0.8H, s), 8.17 (0.8H, s), 8.37 (0.2H, s)

Preparation 24

3-[N-aminosulfonyl-N-(2-hydroxyethyl)amino]methyl imidazo[5,1-b]thiazole and 3-[N-aminosulfonyl-N-(2-aminosulfonyloxyethyl)amino]methylimidazo[5,1-b]thiazole a) 3-[N-(2-hydroxyethyl)amino]methylimidazo[5,1-b]thiazole A 0.25 ml potion of a 4N hydrochloric acid/dioxane solution and 76 mg of 3-formylimidazo[5,1-b]thiazole were added to 2 ml of a methanol solution containing 0.181 ml of 2-aminoethanol, and the mixture was stirred at room temperature for 30 minutes. Then, 42 mg of sodium boron cyanohydride was added thereto, and the mixture was then stirred at room temperature for 3 hours. Afterward, 0.25 ml of a 4N hydrochloric acid/dioxane solution was added thereto, followed by stirring at room temperature for 15 hours. The solvent was evaporated under reduced pressure, and to the resulting residue, an aqueous anhydrous potassium carbonate solution was then added so as to adjust the solution to pH 10.8. Afterward, the mixture was extracted three times with dichloromethane. The organic layer was dried over anhydrous magnesium sulfate and then filtered, and the solvent was evaporated under reduced pressure. The resulting residue was purified by Cephadex LH-20 to obtain 61 mg of the title compound.

NMR (CDCl$_3$) δ: 2.80–2.88 (2H, m), 3.66–3.75 (2H, m), 3.99 (2H, s), 6.65 (1H, s), 7.09 (1H, s), 8.12 (1H, s)

b) 3-[N-aminosulfonyl-N-(2-hydroxyethyl)amino]methyl imidazo[5,1-b]thiazole and 3-[N-aminosulfonyl-N-(2-sulfamoyloxyethyl)amino]methylimidazo[5,1-b]thiazole A 410 mg potion of 3-[N-(2-hydroxyethyl)amino]methyl imidazo[5,1-b]thiazole was dissolved in 6 ml of DMF, and 1.40 ml of triethylamine and 491 mg of sulfamoyl chloride were added thereto at −30° C., followed by stirring at −30 to −20° C. for 4 hours. The reaction solution was concentrated under reduced pressure, dissolved in water, adjusted to pH 7.5 with an aqueous sodium hydrogencarbonate solution, and then purified by Diaion HP-20 Resin and Cephadex LH-20, whereby 59 mg of 3-[N-aminosulfonyl-N-(2-hydroxyethyl)amino]methylimidazo[5,1-b]thiazole was obtained from the first half of the fraction of Cephadex LH-20.

NMR (DMSO-d$_6$) δ: 3.10–3.18 (2H, m), 3.33–3.40 (2H, m), 4.45 (2H, s), 4.75 (1H, t, J=5.0 Hz), 7.07 (3H, m), 7.23 (1H, s), 8.18 (1H, s)

From the latter half of the fraction of Cephadex LH-20, 85 mg of 3-[N-aminosulfonyl-N-(2-sulfamoyloxyethyl)amino]methylimidazo[5,1-b]thiazole was obtained.

NMR (DMSO-d$_6$) δ: 3.35–3.44 (2H, m), 3.96–4.02 (2H, m), 4.47 (2H, s), 7.08 (1H, s), 7.22 (1H, s), 7.27 (2H, s), 7.48 (2H, s), 8.15 (1H, s)

Preparation 25

3-oxamidomethylimidazo[5,1-b]thiazole

A 586 mg potion of ethyl oxamate was added to 12 ml of an ethanol solution containing 255 mg of 3-aminomethylimidazo[5,1-b]thiazole, and the mixture was then stirred at room temperature for 4 days. The resulting crystals were collected by filtration, and then washed with ethanol to obtain 319 mg of the title compound.

NMR (DMSO-d$_6$) δ: 4.48 (2H, d, J=6.1 Hz), 7.03 (1H, s), 7.05 (1H, s), 7.86 (1H, s), 8.15 (1H, s), 8.25 (1H, s), 9.44 (1H, t, J=6.1 Hz)

Preparation 26

3-hydroxyacetamidomethylimidazo[5,1-b]thiazole

To a mixed solution of 4 ml of methanol and 296 mg of THF containing 296 mg of 3-aminomethylimidazo[5,1-b]thiazole, 162 mg of glycolic acid, 26 mg of 1-hydroxybenzotriazole and 439 mg of 1,3-dicyclohexylcarbodiimide were added, and the mixture was then stirred at room temperature for 1 hour. Further, insolubles were removed therefrom by filtration, and after washing with methanol, the filtrate was concentrated under reduced pressure. To the resulting residue, dichloromethane and an aqueous potassium carbonate solution were added, and the crystal was collected by filtration. The organic layer was separated from the filtrate, and the aqueous layer was extracted five times with dichloromethane. The combined organic layer was dried over anhydrous magnesium sulfate and then filtered, and the solvent was evaporated under reduced pressure. The resulting residue was combined with the above crystal, and crystallization was then made from ethyl acetate. To the obtained crystal, 20 ml of water and 2.7 ml of a 1N aqueous hydrochloric acid solution were added, and insolubles were then removed therefrom by filtration. Afterward, anhydrous potassium carbonate was dissolved in the filtrate, and the resulting crystal was collected by filtration, and then washed with dichloromethane and water to obtain 267 mg of the title compound.

NMR (DMSO-$d_6$) δ: 3.87 (2H, d, J=5.8 Hz), 4.47 (2H, d, J=6.0 Hz), 5.57 (1H, t, J=5.8 Hz), 7.00 (1H, s), 7.05 (1H, s), 8.26 (1H, s), 8.52 (1H, t, J=6.0 Hz)

Preparation 27

2-acetoxymethylimidazo[5,1-b]thiazole a) 2-(N-t-butoxycarbonylamino)methyl-5-formylthiazole To 33 ml of a DMF solution containing 5.5 g (purity 65%) of chloromalondialdehyde, 4.7 g of calcium carbonate, 4.8 g of sodium bromide and 5.8 g of (N-t-butoxycarbonyl)aminoacetothioamide were added, and the mixture was then stirred at 60° C. for 11 hours. Then, the solvent was evaporated under reduced pressure, and the resulting residue was dissolved in 300 ml of ethyl acetate. The solution was washed twice with an aqueous saturated sodium bicarbonate solution and once with a 10% saline solution, dried over anhydrous sodium sulfate and then filtered, and the solvent was evaporated under reduced pressure. The resulting residue was purified by a silica gel column chromatograph to obtain 4.57 mg of 2-(N-t-butoxycarbonylamino)methyl-5-formylthiazole.

NMR (CDCl$_3$) δ: 1.48 (9H, s), 4.66 (2H, d, J=6.2 Hz), 5.33 (1H, br.s), 8.32 (1H, s), 10.00 (1H, s)

b) 2-(N-t-butoxycarbonylamino)methyl-5-hydroxymethylthiazole

A 330 mg potion of sodium boron hydride was added to 25 ml of a methanol solution containing 4.12 g of 2-(N-t-butoxycarbonylamino)methyl-5-formylthiazole under ice-cooling, and the mixture was then stirred at room temperature for 1 hour. Under reduced pressure, the solvent was distilled off, and water was added to the resulting residue, followed by extraction with ethyl acetate (80 ml×3). The organic layer was dried over anhydrous sodium sulfate and then filtered, and the solvent was evaporated under reduced pressure to obtain 2.17 g of 2-(N-t-butoxycarbonylamino)methyl-5-hydroxymethylthiazole.

NMR (CDCl$_3$) δ: 1.47 (9H, s), 2.21 (1H, br.s), 4.57 (2H, d, J=6.0 Hz), 4.83 (2H, d, J=4.1 Hz), 5.30 (1H, br.s), 7.54 (1H, s)

c) 5-acetoxymethyl-2-(N-t-butoxycarbonylamino)methylthiazole

A 6 ml portion of anhydrous acetic acid was added to a mixed solution of 10 ml of dichloromethane and 20 ml of pyridine containing 2.17 g of 2-(N-t-butoxycarbonylamino)methyl-5-hydroxymethylthiazole, and the mixture was then allowed to stand at room temperature for 17 hours. Under reduced pressure, the solvent was distilled off, and the resulting residue was dissolved in 120 ml of chloroform. The solution was washed once with water and twice with a 10% saline solution, dried over anhydrous sodium sulfate and then filtered, and the solvent was evaporated under reduced pressure to obtain 2.47 g of 5-acetoxymethyl-2-(N-t-butoxycarbonylamino)methylthiazole.

NMR (CDCl$_3$) δ: 1.47 (9H, s), 2.08 (3H, s), 4.59 (2H, d), 5.23 (2H, m), 7.64 (1H, s)

d) 5-acetoxymethyl-2-(formylamino)methylthiazole

A 8 ml potion of trifluoroacetic acid was dissolved in 2.46 g of 5-acetoxymethyl-2-(N-t-butoxycarbonylamino)methylthiazole under ice-cooling, and the mixture was then allowed to stand at room temperature for 1 hour. Then, the solvent was evaporated under reduced pressure, and the resulting residue was dissolved in 24.6 ml of dichloromethane under ice-cooling. Furthermore, 40 ml of an aqueous saturated sodium bicarbonate solution was added thereto, followed by stirring. To this solution, a 10% aqueous sodium carbonate solution and a mixed acid anhydride solution comprising a mixed solution of 3.7 ml of formic acid and 2.0 ml of acetic anhydride which had been beforehand reacted with each other at 50° C. for 30 minutes were added dropwise under ice-cooling so that the pH of the reaction solution might be within the range of 3.0 to 6.5. Afterward, the organic layer was separated, and the remaining aqueous layer was concentrated under reduced pressure until its amount became half, followed by extraction with chloroform (15 ml×4). The combined organic layer was dried over anhydrous sodium sulfate and then filtered, and the solvent was evaporated under reduced pressure to obtain 1.74 g of 5-acetoxymethyl-2-(formylamino)methylthiazole.

NMR (CDCl$_3$) δ: 2.08 (3H, s), 4.77 (2H, d, J=6.0 Hz), 5.24 (2H, br.s), 6.51 (1H, br.s), 7.65 (1H, s), 8.30 (1H, s)

e) 2-acetoxymethylimidazo[5,1-b]thiazole

A 3.8 ml potion of phosphorus oxychloride was added to 8.7 ml of a toluene solution containing 1.74 g of 5-acetoxymethyl-2-(N-formylamino)methylthiazole, followed by stirring at 100° C. for 2 hours. Then, the solvent was evaporated under reduced pressure, and to the residue, 70 ml of chloroform and 52 ml of an aqueous saturated sodium bicarbonate solution were then added. After stirring, the organic layer was separated. The aqueous layer was extracted with chloroform (26 ml×2). The combined organic layer was combined, and then washed once with the aqueous saturated sodium bicarbonate solution, dried over anhydrous sodium sulfate, and then filtered, and the solvent was evaporated under reduced pressure. The resulting residue was purified by a silica gel column chromatograph to obtain 974 g of the title compound.

NMR (CDCl$_3$) δ: 2.12 (3H, s), 5.12 (2H, d, J=0.8 Hz), 7.07 (1H, s), 7.47 (1H, s), 7.96 (1H, s)

Preparation 28

2-hydroxymethylimidazo[5,1-b]thiazole

A 846 mg potion of 2-acetoxymethylimidazo[5,1-b]thiazole was dissolved in a mixed solution of 17 ml of methanol and 1 ml of an aqueous saturated potassium carbonate solution, followed by stirring at room temperature for 1.5 hours. Then, the reaction solution was filtered, and the filtrate was then concentrated under reduced pressure. The resulting residue was purified by a silica gel column chromatograph to obtain 550 mg of the title compound.

NMR (CD$_3$OD) δ: 4.64 (2H, d, J=1.1 Hz), 7.00 (1H, s), 7.68 (1H, s), 8.10 (1H, s)

Preparation 29

2-(aminosulfonyl)aminomethylimidazo[5,1-b]thiazole a) 2-(N-t-butoxycarbonylamino)methyl-5-phthalimidomethylthiazole To 20 ml of a THF solution containing 1.06 g of 2-(N-t-butoxycarbonylamino)methyl-5-hydroxymethylthiazole, 959 mg of phthalimide, 1.7 g of triphenylphosphine and 1.03 ml of diethyl azodicarboxylate were added, and the mixture was then stirred at room temperature for 1 hour. Then, the solvent was evaporated under reduced pressure, and the resulting residue was purified by a silica gel column chromatograph and Cephadex LH-20 in succession to obtain 1.02 g of 2-(N-t-butoxycarbonylamino)methyl-5-phthalimidomethylthiazole.

NMR (CDCl$_3$) δ: 1.45 (9H, s), 4.55 (2H, d, J=5.5 Hz), 5.00 (2H, br.s), 7.71–7.75 (3H, m), 7.85–7.88 (2H, m)

MS (SIMS): 374 (M$^+$+1)

b) 2-phthalimidomethylimidazo[5,1-b]thiazole

A 25 ml potion of trifluoroacetic acid was added to 1.64 g of 2-(N-t-butoxycarbonylamino)methyl-5-phthalimidomethylthiazole under ice-cooling, and the mixture was then allowed to stand at room temperature for 1 hour. The solvent was evaporated under reduced pressure, and to the resulting residue, 75 ml of dichloromethane and 25 ml of an aqueous saturated sodium bicarbonate solution were added under ice-cooling, followed by stirring. After the aqueous layer was separated, the organic layer was similarly washed once with the aqueous saturated sodium bicarbonate solution, dried over anhydrous sodium sulfate, and then filtered, and the solvent was evaporated under reduced pressure. Afterward, 997 mg of the resulting residue was dissolved in 9 ml of dichloromethane, and a mixed acid anhydride solution comprising a mixed solution of 0.446 ml of acetic anhydride and 0.446 ml of formic acid which had been beforehand reacted with each other at 50° C. for 30 minutes was then added thereto under ice-cooling. After 2 hours, 9 ml of the aqueous saturated sodium bicarbonate solution was added to the reaction solution. The solution was extracted with dichloromethane (9 ml×2). The combined organic layer was washed with the aqueous saturated sodium bicarbonate solution, dried over anhydrous sodium sulfate, and then filtered, and the solvent was evaporated under reduced pressure. Then, to 1.22 g of the resulting residue, 8.9 ml of phosphorus oxychloride was added, followed by stirring under heating at 100° C. for 1 hour. The reaction solution was concentrated under reduced pressure, and the resulting residue was then diluted with 21 ml of dichloromethane under ice-cooling. To this solution, 9 ml of the aqueous saturated sodium bicarbonate solution and 3.2 ml of an aqueous saturated potassium carbonate solution were added under ice-cooling, and after stirring, the organic layer was separated. Furthermore, the aqueous layer was extracted with dichloromethane (27 ml×2). The combined organic layer was washed with the aqueous saturated sodium bicarbonate solution, and the organic layer was dried over anhydrous sodium sulfate, and then filtered. Afterward, the solvent was evaporated under reduced pressure, and the resulting residue was then purified by a silica gel column chromatograph and Cephadex LH-20 in succession to obtain 412 mg of 2-phthalimidomethylimidazo[5,1-b]thiazole.

NMR (CDCl$_3$–CD$_3$OD) δ: 4.96 (2H, br.s), 7.42 (1H, s), 7.79–7.88 (2H, m), 7.88 (1H, s), 7.90–7.93 (2H, m), 8.52 (1H, s)

MS (FD): 283 (M$^+$)

c) 2-(aminosulfonyl)aminomethylimidazo[5,1-b]thiazole

A 0.067 ml potion of anhydrous hydrazine was added to 16 ml of an ethanol solution containing 406 mg of 2-phthalimidomethylimidazo[5,1-b]thiazole, and the solution was then heated under reflux at 90° C. for 1.5 hours. The reaction solution was cooled on ice, and then filtered. The filtrate was concentrated under reduced pressure, and the resulting residue was then diluted with 8 ml of dichloromethane, and then washed with a 1N sodium hydroxide solution. After the organic layer was dried over anhydrous sodium sulfate, and then filtered, and the solvent was evaporated under reduced pressure. Then, 188 mg of the resulting residue was dissolved in 4 ml of DMF. To this solution, 0.963 ml of diisopropylethylamine and 212 mg of sulfamoyl chloride were added, followed by stirring at –60° C. for 4 hours. The solvent was evaporated under reduced pressure, and the resulting residue was purified by Diaion HP-20 Resin to obtain 180 mg of the title compound.

NMR (CD$_3$OD) δ: 4.28 (2H, br.s), 7.01 (1H, s), 7.72 (1H, s), 8.12 (1H, s)

MS (EI): 232 (M$^+$)

Preparation 30

2-(formylamino)methylimidazo[5,1-b]thiazole a) 2-aminomethylimidazo[5,1-b]thiazole A 0.046 ml potion of anhydrous hydrazine was added to 10 ml of a dry ethanol solution containing 278.6 mg of 2-phthalimidomethylimidazo[5,1-b]thiazole, and the solution was then heated under reflux for 2 hours. The reaction solution was cooled on ice, and the resulting crystal was removed therefrom by filtration, followed by washing with a small amount of dichloromethane. The filtrate was concentrated under reduced pressure, and to the resulting residue, 15 ml of dichloromethane was added, and the solution was then alkalified with 1N sodium hydroxide. The aqueous layer was extracted with dichloromethane (20 ml×10). The combined organic layer was dried over anhydrous magnesium sulfate and then filtered, and the solvent was then evaporated under reduced pressure to obtain 154.6 mg of 2-aminomethylimidazo[5,1-b]thiazole.

NMR (CDCl$_3$) δ: 3.91 (2H, s), 7.04 (1H, s), 7.90 (1H, s), 8.24 (1H, s)

b) 2-(formylamino)methylimidazo[5,1-b]thiazole

A mixed solution of 0.14 ml of acetic acid and 0.28 ml of formic acid which had been beforehand reacted with each other at 50° C. for 15 minutes was added to 3 ml of dry dichloromethane containing 154.6 mg of 2-aminomethylimidazo[5,1-b]thiazole at room temperature, and the mixture was then stirred at room temperature for 1 hour. Then, 2 ml of water was added to the reaction solution, and the solution was alkalified with anhydrous potassium carbonate under stirring. The solution was extracted with dichloromethane (15 ml×3). The combined organic layer was dried over anhydrous magnesium sulfate and then filtered, and the solvent was then evaporated under reduced pressure. The resulting crude product was purified by a silica gel column chromatograph to obtain 118.4 mg of the title compound as a colorless solid.

NMR (CDCl$_3$) δ: 4.52 (2H, d, J=6.3 Hz), 6.05 (1H, br.s), 7.06 (1H, s), 7.40 (1H, s), 7.93 (1H, s), 8.24 (1H, s)

Preparation 31

2,5-dihydroxymethylimidazo[5,1-b]thiazole a) 2-(ethoxalylamino)methyl-5-ethoxycarbonylthiazole A 13 ml potion of trifluoroacetic acid was added to 4.00 g of 2-(N-t-butoxycarbonylamino)methyl-5-ethoxycarbonylthiazole under ice-cooling, and the mixture was then stirred at the same temperature for 1 hour. Then, the solvent was concentrated and evaporated under reduced pressure, and 15 ml of dichloromethane and 5 ml of an aqueous saturated sodium hydrogencarbonate solution were then added. In addition, powdery sodium hydrogencarbonate was added until a neutral state was attained. To the solution, 10 ml of dichloromethane in which 32 ml of ethyl chloroglyoxylate was dissolved was added dropwise over 10 minutes, while the reaction solution was maintained in the neutral state by adding sodium hydrogencarbonate and water. The solution was extracted with dichloromethane (10 ml×5), and the extract was washed with water (20 ml). The organic layer was dried over anhydrous magnesium sulfate, and then filtered, and the solvent was evaporated under reduced pressure. The resulting crude product was purified by a silica gel column chromatograph to obtain 3.65 g of 2-(ethoxalylamino)methyl-5-ethoxycarbonylthiazole.

NMR (CDCl$_3$) δ: 1.41 (6H, m), 4.40 (4H, m), 4.87 (2H, d, J=6.4 Hz), 7.85 (1H, br.s), 8.16 (1H, s)

MS (ESI): 287 (M$^+$+H)

b) 2,5-diethoxycarbonylimidazo[5,1-b]thiazole

A 20 ml potion of phosphorus oxychloride was added to 3.53 g of 2-(ethoxalylamino)methyl-5-ethoxycarbonylthiazole under ice-cooling, and the solution was then heated under reflux for 15 hours. After cooled, the reaction solution was concentrated to dryness under reduced pressure, and 20 ml of water and 20 ml of dichloromethane were then added so as to dissolve it. Under ice-cooling, potassium carbonate was added until the solution was alkalified. The solution was extracted with dichloromethane (10 ml×4). The combined organic layer was dried over anhydrous magnesium sulfate, and then filtered, and the solvent was evaporated under reduced pressure. The resulting crude product was purified by a silica gel column chromatograph to obtain 2.37 g of 2,5-diethoxycarbonylimidazo[5,1-b]thiazole.

NMR (CDCl$_3$) δ: 1.40 (6H, m), 4.42 (4H, q, J=7.1 Hz), 7.33 (1H, s), 7.60 (1H, s)

MS (ESI): 269 (M$^+$+H)

c) 2,5-dihydroxymethylimidazo[5,1-b]thiazole

A 9.4 ml portion of a 1.5N diisobutylaluminum hydride/n-hexane solution was added to 10 ml of an anhydrous tetrahydrofuran solution containing 0.758 g of 2,5-diethoxycarbonylimidazo[5,1-b]thiazole, and the mixture was then stirred at −78° C. for 2 hours. Then, 10 ml of methanol was added to the reaction solution, and after stirring for 30 minutes, the solution was subjected to Celite filtration. The solvent was evaporated under reduced pressure, and the resulting crude product was purified by a silica gel column chromatograph to obtain 383.3 mg of the title compound.

NMR (DMSO-d$_6$) δ: 4.70 (2H, d, J=5.5 Hz), 4.76 (2H, d, J=5.5 Hz), 5.43 (1H, t, J=5.5 Hz), 5.65 (1H, t, J=5.5 Hz), 6.97 (1H, s), 7.07 (1H, s)

Preparation 32

3-(allyloxycarbonyl)methylimidazo[5,1-b]thiazole

A 30 mg potion of a sodium ethoxide powder was added to 6.2 ml of an allyl alcohol solution containing 314.2 mg of 3-ethoxycarbonylmethylimidazo[5,1-b]thiazole, and the mixture was then was then heated under reflux for 7 hours. After cooled, the reaction solution was concentrated under reduced pressure, and the organic layer extracted with dichloromethane (10 ml×4) was dried over anhydrous magnesium sulfate, and then filtered, and the solvent was evaporated under reduced pressure. The resulting crude product was purified by a silica gel column chromatograph to obtain 240.4 mg of the title compound as a colorless solid.

NMR (CDCl$_3$) δ: 3.82 (2H, s), 4.65 (2H, d, J=6.0 Hz), 5.29 (2H, m), 5.90 (1H, m), 6.73 (1H, s), 7.11 (1H, s), 7.96 (1H, s)

MS (EI): 222 (M$^+$)

Preparation 33

3-(hydroxyaminocarbonyl)methylimidazo[5,1-b]thiazole

To 2 ml of an ethanol solution containing 204.3 mg of 3-ethoxycarbonylmethylimidazo[5,1-b]thiazole, 108.2 mg of hydroxylamine hydrochloride and 210.2 mg of a sodium ethoxide powder were added, and the mixture was then stirred at room temperature for 2 hours. Under ice-cooling, 0.4 ml of 1N hydrochloric acid was added to the reaction solution to neutralize the solution. The solvent was evaporated under reduced pressure, and the resulting residue was purified by Diaion HP-20 Resin to obtain 140 mg of the title compound.

NMR (D$_2$O) δ(HOD=4.75 ppm): 3.80 (2H, s), 6.94 (1H, s), 7.06 (1H, s), 8.07 (1H, s)

MS (EI): 197 (M$^+$)

Preparation 34

3-phenylimidazo[5,1-b]thiazole

The same procedure as in Preparation 10 was repeated except that 1.9 g of (N-t-butoxycarbonylamino) acetothioamide and 2.49 g of 2'-bromoacetophenone were used, thereby obtaining 1.32 g of the title compound.

NMR (CDCl$_3$) δ: 6.78 (1H, s), 7.07 (1H, s), 7.17 (1H, s), 7.52 (3H, m), 7.65 (2H, m), 8.18 (1H, s)

Preparation 35

3-acetylimidazo[5,1-b]thiazole

A 651 mg potion of 3-(1-hydroxyethyl)imidazo[5,1-b]thiazole was dissolved in 130 ml of dichloromethane, and 9.77 g of active manganese dioxide was then added, followed by stirring at room temperature for 4 hours. After the completion of the reaction, insolubles were removed therefrom by filtration, followed by washing with dichloromethane. The filtrate was concentrated to dryness under reduced pressure to obtain 550 mg of the title compound.

NMR (CDCl$_3$) δ: 2.58 (3H, s), 7.17 (1H, s), 780 (1H, s), 8.78 (1H, s)

Preparation 36

2-carbamoylimidazo[5,1-b]thiazole

A 294 mg potion of 2-ethoxycarbonylimidazo[5,1-b]thiazole was dissolved in 8 ml of a 2M ammonia/methanol solution, and the mixture was then stirred at room temperature for 4 days. After concentration under reduced pressure, 3 ml of dichloromethane was added to the resulting residue, and the precipitate was collected by filtration, washed with dichloromethane, and then dried under reduced pressure to obtain 226 mg of the title compound.

NMR (DMSO-$d_6$) δ: 7.05 (1H, s), 7.72 (1H, br.s), 8.19 (1H, br.s), 8.33 (1H, s), 8.50 (1H, s)

Preparation 37

3-(1-hydroxyethyl)imidazo[5,1-b]thiazole

Under an argon atmosphere, 1 ml of a 3.0M methylmagnesium bromide-diethyl ether solution was added dropwise to 15 ml of an anhydrous THF solution containing 304 mg of 3- formylimidazo[5,1-b]thiazole at −78° C., and the mixture was then stirred at the same temperature for 3.5 hours. Further, an aqueous ammonium chloride solution was added to the reaction solution, and the solution was then extracted three times with ethyl acetate. The organic layer was dried over anhydrous sodium sulfate and then filtered, and the solvent was evaporated under reduced pressure. The resulting residue was purified by a silica gel column chromatograph to obtain 296 mg of the title compound as a colorless crystal.

NMR (CD$_3$OD) δ: 1.65 (3H, d, J=7.5 Hz), 5.01 (1H, q, J=7.5 Hz), 6.61 (1H, s), 6.97 (1H, s), 8.09 (1H, s)

Preparation 38

2,3-bis(ethoxycarbonyl)imidazo[5,1-b]thiazole a) 4,5-bis(ethoxycarbonyl)-2-(N-t-butoxycarbonylamino)methylthiazole To 100 ml of anhydrous DMF containing 7.39 g of diethyl 2-chloro-3-oxosuccininate, 5.7 g of (N-t-butoxycarbonylamino)acetothioamide, 1.65 g of calcium carbonate and 3.09 g of sodium bromide were added in turn, and the mixture was then stirred at room temperature for 5 hours. The reaction solution was diluted with ethyl acetate, filtered through Celite, and then washed with an aqueous saturated sodium hydrogencarbonate solution and a saturated saline solution. The organic layer was dried over anhydrous sodium sulfate and then filtered, and the solvent was evaporated under reduced pressure. The resulting residue was purified by a silica gel column chromatograph to obtain 8.5 g of 4,5-bis(ethoxycarbonyl)-2-(N-t-butoxycarbonylamino)methylthiazole.

NMR (CDCl$_3$) δ: 1.36 (3H, t, J=7.2 Hz), 1.40 (3H, t, J=7.2 Hz), 1.47 (9H, s), 4.36 (2H, q, J=7.2 Hz), 4.43 (2H, q, J=7.2 Hz), 4.60 (2H, d, J=6.3 Hz), 5.26–5.36 (1H, br.s)

MS (EI): 359 (M$^+$+1)

b) 2,3-bis(ethoxycarbonyl)imidazo[5,1-b]thiazole

A 30 ml potion of trifluoroacetic acid was added to 10.24 g 4,5-bis(ethoxycarbonyl)-2-t-butoxycarbonylaminomethylthiazole, and the mixture was then stirred at room temperature for 1 hour. The reaction solution was concentrated under reduced pressure, and an aqueous saturated sodium hydrogencarbonate solution was then added so as to adjust the pH of the solution to about 8. Further, 150 ml of dichloromethane was added thereto, and a mixture of 27 ml of formic acid and 13.5 ml of acetic anhydride which had been beforehand reacted with each other at 50° C. for 30 minutes was then added at room temperature with vigorous stirring, followed by stirring for additional 1 hour. The organic layer was separated, and the aqueous layer was further extracted with dichloromethane three times. The combined organic layer was dried over anhydrous sodium sulfate and then filtered, and the solvent was evaporated under reduced pressure. To the resulting unpurified 4,5-bis(ethoxycarbonyl)-2-(formylamino)methylthiazole, 30 ml of toluene and 13.3 ml of phosphorus oxychloride were added, followed by stirring at 100° C. for 80 minutes. After cooled to room temperature, the reaction solution was concentrated under reduced pressure, and the resulting residue was then diluted with dichloromethane. Afterward, an aqueous potassium carbonate solution was added so as to adjust the pH of the solution to about 8. The organic layer was separated, and it was further extracted four times from the aqueous layer with dichloromethane. The combined organic layer was dried over anhydrous sodium sulfate and then filtered, and the solvent was evaporated under reduced pressure. The resulting residue was purified by a silica gel column chromatograph to obtain 6.6 g of the title compound.

NMR (CDCl$_3$) δ: 1.40 (3H, t, J=7.2 Hz), 1.44 (3H, t, J=7.1 Hz), 4.41 (2H, q, J=7.2 Hz), 4.49 (2H, q, J=7.1 Hz), 7.16 (1H, s), 8.43 (1H, s)

MS (EI): 269 (M$^+$+1)

Preparation 39

2,3-dihydroxymethylimidazo[5,1-b]thiazole

A 1.33 ml potion of a 1.5M diisobutylaluminum hydride-toluene solution was added dropwise to 5 ml of an anhydrous THF solution containing 268 mg of 2,3-bis(ethoxycarbonyl)imidazo[5,1-b]thiazole in an argon atmosphere at −78° C., and the mixture was then stirred at the same temperature for 1 hour. Then, the reaction solution was diluted with 5 ml of diethyl ether, and 1.5 ml of water was then added thereto. After stirred at room temperature for 2 hours, the solution was filtered through Celite. The filtrate was dried over anhydrous magnesium sulfate and then filtered, and the solvent was evaporated under reduced pressure. The resulting residue was purified by a silica gel column chromatograph to obtain 148 mg of the title compound as a colorless crystal.

NMR (CD$_3$OD) δ: 4.70 (2H, s), 4.78 (2H, s), 7.04 (1H, s), 8.20 (1H, s)

MS (EI): 184 (M$^+$)

Preparation 40

2,3-dicarbamoylimidazo[5,1-b]thiazole

A 30 ml potion of a 2.0M ammonia/methanol solution was added to 268 mg of 2,3-bis(ethoxycarbonyl)imidazo[5,1-b]thiazole at room temperature, followed by stirring at the same temperature for one day. The resulting precipitate was collected by filtration, and then dried under reduced pressure to obtain 188 mg of the title compound.

NMR (DMSO-$d_6$) δ: 7.14 (1H, s), 8.20–8.50 (4H, m), 8.90–9.10 (1H, br.s)

MS (EI): 210 (M$^+$)

Preparation 41

3-hydroxymethyl-2-methylimidazo[5,1-b]thiazole a) 2-(N-t-butoxycarbonylamino)methyl-4-ethoxycarbonyl-5-methylthiazole To 250 ml of an anhydrous DMF solution containing 24.6 g of ethyl 3-bromo-2-oxosuccininate, 21.5 g of (N-t- butoxycarbonylamino)acetothioamide and 6.9 g of calcium carbonate were added, and the mixture was then stirred at 40° C. for 15 hours. After diluted with ethyl acetate, the reaction solution was filtered through Celite, followed by washing with water, an aqueous saturated sodium hydrogencarbonate solution and a saturated saline solution in succession. The organic layer was dried over anhydrous sodium sulfate and then filtered, and the solvent was evaporated under reduced pressure. The resulting residue was purified by a silica gel column chromatograph to obtain 23.5 g of 2-(N-t-butoxycarbonylamino)methyl-4-ethoxycarbonyl-5-methylthiazole as a yellow crystal.

NMR (CDCl$_3$) δ: 1.41 (3H, t, J=7.1 Hz), 2.75 (3H, s), 4.41 (2H, q, J=7.1 Hz), 4.55 (2H, d, J=6.0 Hz),, 5.26–5.36 (1H, br.s)

MS (EI): 300 (M$^+$)

b) 3-ethoxycarbonyl-2-methylimidazo[5,1-b]thiazole

A 30 ml portion of trifluoroacetic acid was added to 9.0 g of 2-(N-t-butoxycarbonylamino)methyl-4-ethoxycarbonyl-5-methylthiazole, and the mixture was then stirred at room temperature for 1 hour. After the reaction solution was concentrated under reduced pressure, an aqueous saturated sodium hydrogencarbonate solution was added so as to adjust the pH of the solution to about 8. Then, 150 ml of dichloromethane was added, and a mixture of 28.4 ml of formic acid and 14.2 ml of acetic anhydride which had been beforehand reacted with each other at 50° C. for 30 minutes was then added at room temperature with vigorous stirring, followed by stirring for additional 1 hour. The organic layer was separated, and the aqueous layer was further extracted four times with dichloromethane. The combined organic layer was dried over anhydrous sodium sulfate and then filtered, and the solvent was evaporated under reduced pressure. To the resulting unpurified 4-ethoxycarbonyl-2-(formylamino)methyl-5-methylthiazole, 30 ml of toluene and 14 ml of phosphorus oxychloride were added, followed by stirring at 100° C. for 1 hour. After cooled to room temperature, the reaction solution was concentrated under reduced pressure, and the resulting residue was then diluted with dichloromethane. Afterward, an aqueous potassium carbonate solution was added so as to adjust the pH of the solution to about 8. The organic layer was separated, and the aqueous layer was further extracted five times with dichloromethane. The combined organic layer was dried over anhydrous magnesium sulfate and then filtered, and the solvent was evaporated under reduced pressure to obtain 5.43 g of 3-ethoxycarbonyl-2-methylimidazo[5,1-b]thiazole.

NMR (CDCl$_3$) δ: 1.46 (3H, t, J=7.1 Hz), 2.71 (3H, s), 4.46 (2H, q, J=7.1 Hz), 7.08 (1H, s), 8.49 (1H, s)

MS (EI): 210 (M$^+$)

c) 3-hydroxymethyl-2-methylimidazo[5,1-b]thiazole

A 1.91 g portion of sodium boron hydride was added to 30 ml of a methanol solution containing 2.10 g of 3-ethoxycarbonyl-2-methylimidazo[5,1-b]thiazole, and the mixture was then stirred at room temperature for 2 hours. The solvent was evaporated under reduced pressure, and water was added to the residue and the solution was then extracted five times with dichloromethane. The organic layer was dried over anhydrous magnesium sulfate and then filtered, and the solvent was evaporated under reduced pressure. The resulting residue was purified by a silica gel column chromatograph to obtain 1.4 g of the title compound as a yellow crystal.

NMR (CDCl$_3$) δ: 2.34 (3H, s), 4.76 (2H, s), 6.96 (1H, s), 8.00 (1H, s)

MS (EI): 168 (M$^+$)

Preparation 42

3-(formylamino)methyl-2-methylimidazo[5,1-b]thiazole a) 3-phthalimidomethyl-2-methylimidazo[5,1-b]thiazole Under an argon atmosphere, 1.8 ml of diethyl azodicarboxylate was added dropwise to 30 ml of an anhydrous THF solution containing 962 mg of 3-hydroxymethyl-2-methylimidazo[5,1-b]thiazole, 1.68 g of phthalimide and 3.0 g of triphenylphosphine at room temperature, and the mixture was then stirred at room temperature for 2 hours as it was. The solvent was evaporated under reduced pressure, and the resulting residue was purified through a silica gel column chromatograph to obtain 1.7 g of 3-phthalimidomethyl-2-methylimidazo[5,1-b]thiazole.

NMR (CDCl$_3$) δ: 2.61 (3H, s), 4.93 (2H, s), 7.01 (1H, s), 7.73–7.76 (2H, m), 7.86–7.89 (2H, m), 8.27 (1H, s)

b) 3-aminomethyl-2-methylimidazo[5,1-b]thiazole

A 0.42 ml portion of hydrazine hydrate was added to 30 ml of a dry ethanol solution containing 1.7 g of 3-phthalimidomethyl-2-methylimidazo[5,1-b]thiazole, and the mixture was then heated under reflux for 2 hours. The reaction solution was cooled on ice, and the resulting crystal was filtered and then washed with a small amount of cold methanol. The filtrate was concentrated under reduced pressure, and to the resulting residue, dichloromethane was added. The solution was extracted with 1N hydrochloric acid, and the extract was then alkalified with a 1N aqueous potassium hydroxide solution. The organic layer extracted from the aqueous layer with dichloromethane was dried over anhydrous magnesium sulfate and then filtered, and the filtrate was evaporated under reduced pressure to obtain 820 mg of 3-aminomethyl-2-methylimidazo[5,1-b]thiazole as a green powder.

NMR (CDCl$_3$) δ: 2.35 (3H, s), 4.00 (2H, s), 7.03 (1H, s), 8.08 (1H, s)

MS (EI): 167 (M$^+$)

c) 3-(formylamino)methyl-2-methylimidazo[5,1-b]thiazole

A mixture of 0.94 ml of formic acid and 0.47 ml of acetic anhydride which had been beforehand reacted with each other at 50° C. for 30 minutes was added at room temperature to 5 ml of a dry dichloromethane solution containing 167 mg of 3-aminomethyl-2-methylimidazo[5,1-b]thiazole, and the mixture was then stirred at the same temperature for 1 hour. Then, an aqueous potassium carbonate solution was added to the reaction solution to alkalify the same. The organic layer was separated, and the aqueous layer was further extracted five times with dichloromethane. The combined organic layer was dried over anhydrous sodium sulfate and then filtered, and the solvent was evaporated under reduced pressure to obtain 117 mg of the title compound.

NMR (DMSO-d$_6$) δ: 2.36 (3H, s), 4.46 (2H, d, J=6.0 Hz), 7.00 (1H, s), 8.09 (1H, s), 8.11 (1H, s), 8.60–8.70 (1H, br.s)

MS (EI): 195 (M$^+$)

Preparation 43

3-(aminosulfonyl)aminomethyl-2-methylimidazo[5,1-b]thiazole

Under an argon atmosphere at −40° C., 0.84 ml of triethylamine was added dropwise to 5 ml of a dry DMF solution containing 334 mg of 3-aminomethyl-2-methylimidazo[5,1-b]thiazole, and 347 mg of sulfamoyl chloride was further added, followed by stirring at −40 to −10° C. for 3 hours. After the reaction solution was diluted with water, sodium hydrogencarbonate was used to adjust the pH of the solution to about 7.5, and the thus adjusted solution was directly subjected to Diaion HP-20 Resin to obtain 110 mg of the title compound as a light green powder.

NMR (DMSO-$d_6$) δ: 2.41 (2H, s), 4.29 (2H, d, J=6.3 Hz), 6.95 (2H, s), 7.09 (1H, s), 7.29 (1H, t, J=6.3 Hz), 8.23 (1H, s)

MS (FD): 246 (M$^+$)

EXAMPLE 19

(1S,5R,6S)-6-[(1R)-1-hydroxyethyl]-2-[3-(aminosulfonyl)aminomethylimidazo[5,1-b] thiazolium-6-yl]methyl-1-methyl-1-carbapen-2-em-3-carboxylate (internal salt)

The same procedure as in Example 14 was repeated except that Cosmosil 40C18-PREP was used for purification, and 3.5 g of allyl (1S,5R,6S)-6-[(1R)-1-allyloxycarbonyloxyethyl]-2-hydroxymethyl-1-methyl-1-carbapen-2-em-3-carboxylate and 2.78 mg of 3-(aminosulfonyl)aminomethylimidazo[5,1-b]thiazole were used, thereby obtaining 683 mg of the title compound.

NMR (D$_2$O) δ(HOD=4.80 ppm): 1.08 (3H, d, J=7.4 Hz), 1.25 (3H, d, J=6.3 Hz), 3.00–3.11 (1H, m), 3.48 (1H, dd, J$_1$=6.0 Hz, J$_2$=3.0 Hz), 4.18–4.27 (2H, m), 4.55 (2H, s), 5.24 (1H, d, J=15.0 Hz), 5.74 (1H, d, J=15.0 Hz), 7.51 (1H, s), 7.76 (1H, s)

EXAMPLE 20

(1S,5R,6S)-6-[(1R)-1-hydroxyethyl]-2-[3-[2-(aminosulfonyl)aminoethyl]imidazo[5,1-b] thiazolium-6-yl]methyl-1-methyl-1-carbapen-2-em-3-carboxylate (internal salt)

The same procedure as in Example 1 was repeated except that aniline was used as a trapping agent for an allyl removal reaction, Diaion CHP-20P was used for purification, and 129 mg of allyl (1S,5R,6S)-6-[(1R)-1-allyloxycarbonyloxyethyl]-2-hydroxymethyl-1-methyl-1-carbapen-2-em-3-carboxylate and 233 mg of 3-[2-(N-allyloxycarbonyl-N-(aminosulfonyl)amino]methyl]imidazo[5,1-b]thiazole were used, thereby obtaining 18.4 mg of the title compound.

NMR (D$_2$O) δ(HOD=4.80 ppm): 1.11 (3H, d, J=7.4 Hz), 1.27 (3H, d, J=6.4 Hz), 2.99–3.10 (1H, m), 3.18 (2H, t, J$_1$=6.3 Hz), 3.47–3.52 (3H, m), 4.18–4.28 (2H, m), 5.20 (1H, d, J=15.1 Hz), 5.80 (1H, d, J=15.1 Hz), 7.32 (1H, s), 7.74 (1H, s)

MS (SIMS): 470 (M$^+$+1)

EXAMPLE 21

(1S,5R,6S)-6-[(1R)-1-hydroxyethyl]-2-(3-ethoxycarbonylimidazo[5,1-b]thiazolium-6-yl) methyl-1-methyl-1-carbapen-2-em-3-carboxylate (internal salt)

The same procedure as in Example 1 was repeated except that Cosmosil 40C18 was used for purification, and 102.7 mg of allyl (1S,5R,6S)-6-[(1R)-1-allyloxycarbonyloxyethyl]-2-hydroxymethyl-1-methyl-1-carbapen-2-em-3-carboxylate and 110 mg of 3-ethoxycarbonylimidazo[5,1-b]thiazole were used, thereby obtaining 3.6 mg of the title compound.

NMR (D$_2$O) δ(HOD=4.80 ppm): 1.13 (3H, d, J=7.4 Hz), 1.29 (3H, d, J=5.0 Hz), 1.45 (3H, t, J=7.1 Hz), 3.08 (1H, m), 3.51 (1H, dd, J$_1$=6.0 Hz, J$_2$=3.0 Hz), 4.20–4.30 (2H, m), 4.53 (2H, q, J=7.1 Hz), 5.29 (1H, d, J=14.8 Hz), 5.84 (1H, d, J=14.8 Hz), 7.89 (1H, s), 8.56 (1H, s), 9.74 (1H, s)

EXAMPLE 22

(1S,5R,6S)-6-[(1R)-1-hydroxyethyl]-2-[3-(methanesulfonylamino)methylimidazo[5,1-b] thiazolium-6-yl]methyl-1-methyl-1-carbapen-2-em-3-carboxylate (internal salt)

The same procedure as in Example 1 was repeated except that aniline was used as a trapping agent for a deprotective reaction, Cosmosil 40C18 was used for purification, and 162 mg of allyl (1S,5R,6S)-6-[(1R)-1-allyloxycarbonyloxyethyl]-2-hydroxymethyl-1-methyl-1-carbapen-2-em-3-carboxylate and 205 mg of 3-(methanesulfonyl)methylimidazo[5,1-b]thiazole were used, thereby obtaining 2.5 mg of the title compound.

NMR (D$_2$O) δ(HOD=4.80 ppm): 1.11 (3H, d, J=7.4 Hz), 1.29 (3H, d, J=5.0 Hz), 3.10 (1H, m), 3.20 (3H, s), 3.52 (1H, dd, J$_1$=6.0 Hz, J$_2$=2.9 Hz), 4.21–4.29 (2H, m), 4.66 (2H, s), 5.30 (1H, d, J=14.9 Hz), 5.76 (1H, d, J=14.9 Hz), 7.58 (1H, s), 7.82 (1H, s), 9.44 (1H, s)

EXAMPLE 23

(1S,5R,6S)-6-[(1R)-1-hydroxyethyl]-2-[3-(N,N-dimethylsulfonyl)amino]methylimidazo[5,1-b] thiazolium-6-yl]methyl-1-methyl-1-carbapen-2-em-3-carboxylate (internal salt)

The same procedure as in Example 1 was repeated except that aniline was used as a trapping agent for a deprotective reaction, Cosmosil 40C18 was used for purification, and 113 mg of allyl (1S,5R,6S)-6-[(1R)-1-allyloxycarbonyloxyethyl]-2-hydroxymethyl-1-methyl-1-carbapen-2-em-3-carboxylate and 165 mg of 3-(N,N-dimethylamminosulfonyl)amino]methylimidazo[5,1-b] thiazole were used, thereby obtaining 4.9 mg of the title compound.

NMR (D$_2$O) δ(HOD=4.80 ppm): 1.08 (3H, d, J=7.1 Hz), 1.25 (3H, d, J=6.3 Hz), 2.75 (6H, m), 3.06 (1H, m), 3.48 (1H, dd, J$_1$=5.8 Hz, J$_2$=2.8 Hz), 4.56 (2H, s), 5.27 (1H, d, J=14.7 Hz), 5.74 (1H, d, J=14.7 Hz), 7.54 (1H, s), 7.80 (1H, s), 9.41 (1H, s)

EXAMPLE 24

(1S,5R,6S)-6-[(1R)-1-hydroxyethyl]-2-[3-(N-2-hydroxyethyl)carbamoylimidazo[5,1-b]thiazolium-6-yl]methyl-1-methyl-1-carbapen-2-em-3-carboxylate (internal salt)

The same procedure as in Example 1 was repeated except that 93 mg of allyl (1S,5R,6S)-6-[(1R)-1-allyloxycarbonyloxyethyl]-2-hydroxymethyl-1-methyl-1-carbapen-2-em-3-carboxylate and 80 mg of 3-(N-2-hydroxyethyl)carbamoylimidazo[5,1-b]thiazole were used, thereby obtaining 15 mg of the title compound.

NMR (D$_2$O) δ(HOD=4.82 ppm): 1.11 (3H, d), 1.29 (3H, d), 3.05 (1H, m), 3.49 (1H, dd), 3.58 (2H, t), 3.77 (2H, t), 4.19–4.27 (2H, m), 5.25 (1H, d), 5.83 (1H, d), 7.82 (1H, s), 8.33 (1H, s), 9.75 (1H, s)

EXAMPLE 25

(1S,5R,6S)-6-[(1R)-1-hydroxyethyl]-2-(3-phenylimidazo[5,1-b]thiazolium-6-yl)methyl-1-methyl-1-carbapen-2-em-3-carboxylate (internal salt)

The same procedure as in Example 1 was repeated except that 104 mg of allyl (1S,5R,6S)-6-[(1R)-1- allyloxycarbonyloxyethyl]-2-hydroxymethyl-1-methyl-1-carbapen-2-em-3-carboxylate and 86 mg of 3-phenylimidazo[5,1-b]thiazole were used, thereby obtaining 16.2 mg of the title compound.

NMR (D$_2$O) δ(HOD=4.82 ppm): 1.11 (3H, d), 1.27 (3H, d), 3.04 (1H, m), 3.48 (1H, dd), 4.17–4.24 (2H, m), 5.17 (1H, d), 5.83 (1H, d), 7.56 (1H, s), 7.62 (3H, m), 7.72 (2H, m), 7.80 (1H, s), 9.54 (1H, s)

EXAMPLE 26

(1S,5R,6S)-6-[(1R)-1-hydroxyethyl]-2-(2-hydroxymethylimidazo[5,1-b]thiazolium-6-yl) methyl-1-methyl-1-carbapen-2-em-3-carboxylate (internal salt)

The same procedure as in Example 1 was repeated except that 103 mg of allyl (1S,5R,6S)-6-[(1R)-1-allyloxycarbonyloxyethyl]-2-hydroxymethyl-1-methyl-1-carbapen-2-em-3-carboxylate and 87 mg of 2-hydroxymethylimidazo[5,1-b]thiazole were used, thereby obtaining 3.3 mg of the title compound.

NMR (D$_2$O) δ(HOD=4.80 ppm): 1.09 (3H, d, J=7.2 Hz), 1.26 (3H, d, J=6.5 Hz), 3.04 (1H, m), 3.48 (1H, m), 4.17–4.25 (1H, m), 4.80 (2H, s), 5.17 (1H, d, J=14.6 Hz), 5.78 (1H, d), 7.69 (1H, s), 7.90 (1H, s), 9.30 (1H, s)

MS (SIMS): 377 (M$^+$+1)

EXAMPLE 27

(1S,5R,6S)-6-[(1R)-1-hydroxyethyl]-2-[2-[(N,N-dimethylaminosulfonyl)aminomethyl-3-methylimidazo[5,1-b]thiazolium-6-yl]methyl-1-methyl-1-carbapen-2-em- 3-carboxylate (internal salt)

The same procedure as in Example 1 was repeated except that 113.7 mg of allyl (1S,5R,6S)-6-[(1R)-1-allyloxycarbonyloxyethyl]-2-hydroxymethyl-1-methyl-1-carbapen-2-em-3-carboxylate and 128 mg of 2-[(N,N-dimethylaminosulfonyl)amino]methyl-3-methylimidazo[5,1-b]thiazole were used, thereby obtaining 11.1 mg of the title compound.

NMR (D$_2$O) δ(HOD=4.80 ppm): 1.10 (3H, d, J=7.1 Hz), 1.25 (3H, d, J=6.3 Hz), 2.48 (3H, s), 2.79 (6H, s), 3.02 (1H, m), 3.47 (1H, dd, J$_1$=5.8 Hz, J$_2$=2.9 Hz), 4.14–4.28 (2H, m), 4.43 (2H, s), 5.16 (1H, d, J=15.4 Hz), 5.80 (1H, d, J=15.4 Hz), 7.70 (1H, s), 9.35 (1H, s)

EXAMPLE 28

(1S,5R,6S)-6-[(1R)-1-hydroxyethyl]-2-(2-(aminosulfonyl)amino]methylimidazo[5,1-b] thiazolium-6-yl)methyl-1-methyl-1-carbapen-2-em-3-carboxylate (internal salt)

The same procedure as in Example 1 was repeated except that Cosmosil 40C18 was used for purification, and 89.0 mg of allyl (1S,5R,6S)-6-[(1R)-1-allyloxycarbonyloxyethyl]-2-hydroxymethyl-1-methyl-1-carbapen-2-em-3-carboxylate and 70 mg of 2-(aminosulfonyl)aminomethylimidazo[5,1-b]thiazole were used, thereby obtaining 7.5 mg of the title compound.

NMR (D$_2$O) δ(HOD=4.80 ppm): 1.09 (3H, d, J=6.5 Hz), 1.26 (3H, d, J=5.8 Hz), 3.00–3.06 (1H, m), 3.46–3.49 (1H, m), 4.16–4.25 (2H, m), 4.47 (2H, s), 5.17 (1H, d, J=14.8 Hz), 5.75 (1H, d, J=15.0 Hz), 7.68 (1H, s), 7.93 (1H, s)

EXAMPLE 29

(1S,5R,6S)-6-[(1R)-1-hydroxyethyl]-2-(2-acetoxymethylimidazo[5,1-b]thiazolium-6-yl) methyl-1-methyl-1-carbapen-2-em-3-carboxylate (internal salt)

The same procedure as in Example 1 was repeated except that 120 mg of allyl (1S,5R,6S)-6-[(1R)-1-allyloxycarbonyloxyethyl]-2-hydroxymethyl-1-methyl-1-carbapen-2-em-3-carboxylate and 97 mg of 2-acetoxymethylimidazo[5,1-b]thiazole were used, thereby obtaining 17.9 mg of the title compound.

NMR (D$_2$O) δ(HOD=4.80 ppm): 1.09 (3H, d, J=7.4 Hz), 1.26 (3H, d, J=6.3 Hz), 2.15 (3H, s), 3.01–3.07 (1H, m), 3.46–3.49 (1H, m), 4.17–4.25 (2H, m), 5.18 (1H, d, J=14.9 Hz), 5.30 (2H, s), 5.72 (1H, d, J=14.9 Hz), 7.70 (1H, s), 8.04 (1H, s)

MS (SIMS): 421 (M$^+$+2)

EXAMPLE 30

(1S,5R,6S)-6-[(1R)-1-hydroxyethyl]-2-(5-(aminosulfonyl)aminomethylimidazo[5,1-b] thiazolium-6-yl)methyl-1-methyl-1-carbapen-2-em-3-carboxylate (internal salt)

The same procedure as in Example 1 was repeated except that a reversed phase HPLC (Cosmosil 5C18-MS) was used for purification, and 92.8 mg of allyl (1S,5R,6S)-6-[(1R)-1-allyloxycarbonyloxyethyl]-2-hydroxymethyl-1-methyl-1-carbapen-2-em-3-carboxylate and 295 mg of 5-(aminosulfonyl)aminomethylimidazo[5,1-b]thiazole were used, thereby obtaining 3.4 mg of the title compound.

NMR (D$_2$O) δ(HOD=4.80 ppm): 1.14 (3H, d, J=7.4 Hz), 1.25 (3H, d, J=6.3 Hz), 2.95 (1H, m), 3.47 (1H, dd, J$_1$=6.0 Hz, J$_2$=3.1 Hz), 4.10–4.27 (2H, m), 4.85 (2H, s), 5.16 (1H, d, J=15.7 Hz), 6.01 (1H, d, J=15.7 Hz), 7.60 (1H, d, J=4.3 Hz), 7.77 (1H, s), 8.06 (1H, d, J=4.3 Hz)

EXAMPLE 31

(1S,5R,6S)-6-[(1R)-1-hydroxyethyl]-2-(5-hydroxymethylimidazo[5,1-b]thiazolium-6-yl) methyl-1-methyl-1-carbapen-2-em-3-carboxylate (internal salt)

The same procedure as in Example 1 was repeated except that Cosmosil 40C18 was used for purification, and 109.8 mg of allyl (1S,5R,6S)-6-[(1R)-1-allyloxycarbonyloxyethyl]-2-hydroxymethyl-1-methyl-1-carbapen-2-em-3-carboxylate and 231.7 mg of 5-hydroxymethylimidazo[5,1-b]thiazole were used, thereby obtaining 3.2 mg of the title compound.

NMR (D$_2$O) δ(HOD=4.75 ppm): 1.08 (3H, d, J=7.3 Hz), 1.21 (3H, d, J=6.5 Hz), 2.90 (1H, m), 3.42 (1H, m), 4.08–4.20 (2H, m), 5.10 (2H, s), 5.11 (1H, d, J=15.5 Hz), 5.89 (1H, d, J=15.5 Hz), 7.53 (1H, d, J=4.1 Hz), 7.69 (1H, s), 8.01 (1H, d, J=4.1 Hz)

EXAMPLE 32

(1S,5R,6S)-6-[(1R)-1-hydroxyethyl]-2-(3-aminoimidazo-[5,1-b]thiazolium-6-yl)methyl-1-methyl-1-carbapen-2-em-3-carboxylate (internal salt)

The same procedure as in Example 1 was repeated except that aniline was used as a trapping agent for a deprotective reaction, Cosmosil 40C18 was used for purification, and 105.5 mg of allyl (1S,5R,6S)-6-[(1R)-1-allyloxycarbonyloxyethyl]-2-hydroxymethyl-1-methyl-1-carbapen-2-em-3-carboxylate and 97 mg of 3-allyloxycarbonylaminoimidazo[5,1-b]thiazole were used, thereby obtaining 1.2 mg of the title compound (an equilibrium mixture with an imine type).

NMR (D$_2$O) δ(HOD=4.80 ppm): 1.04 (1.2H, d, J=7.3 Hz), 1.10 (1.8H, d, J=7.4 Hz), 1.25 (1.2H, d, J=6.2 Hz), 1.26

(1.8H, d, J=6.3 Hz), 2.86–3.08 (1H, m), 3.45–3.50 (1H, m), 3.74 (0.8H, s), 4.12–4.28 (2H, m), 4.93 (0.4H, d, J=15.1 Hz), 5.19 (0.6H, d, J=15.1 Hz), 5.49 (0.4H, d, J=15.1 Hz), 5.78 (0.6H, d, J=15.1 Hz), 6.32 (0.6H, s), 7.66 (0.6H, s), 7.68 (0.4H, s), 8.17 (0.4H, s), 9.27 (0.6H, s)

EXAMPLE 33

(1S,5R,6S)-6-[(1R)-1-hydroxyethyl]-2-[3-[(aminosulfonyl)aminooxy]methylimidazo[5,1-b]thiazolium-6-yl]methyl-1-methyl-1-carbapen-2-em-3-carboxylate (internal salt)

The same procedure as in Example 1 was repeated except that Cosmosil 40C18 was used for purification, and 97.7 mg of allyl (1S,5R,6S)-6-[(1R)-1-allyloxycarbonyloxyethyl]-2-hydroxymethyl-1-methyl-1-carbapen-2-em-3-carboxylate and 101.3 mg of 3-[(aminosulfonyl)aminooxy]methylimidazo[5,1-b]thiazole were used, thereby obtaining 1.3 mg of the title compound.

NMR (D$_2$O) δ(HOD=4.75 ppm): 1.06 (3H, d, J=7.0 Hz), 1.21 (3H, d, J=6.5 Hz), 2.99 (1H, m), 3.44 (1H, m), 4.13–4.21 (2H, m), 5.14 (2H, s), 5.17 (1H, d, J=15.0 Hz), 5.73 (1H, d, J=15.0 Hz), 7.61 (1H, s), 7.72 (1H, s), 9.44 (1H, s)

EXAMPLE 34

(1S,5R,6S)-6-[(1R)-1-hydroxyethyl]-2-[3-(N-aminosulfonyl-N-methylamino)methylimidazo[5,1-b]thiazolium-6-yl]methyl-1-methyl-1-carbapen-2-em-3-carboxylate (internal salt)

The same procedure as in Example 1 was repeated except that Cosmosil 40C18 was used for purification, and 83.1 mg of allyl (1S,5R,6S)-6-[(1R)-1-allyloxycarbonyloxyethyl]-2-hydroxymethyl-1-methyl-1-carbapen-2-em-3-carboxylate and 90.1 mg of 3-(N-aminosulfonyl-N-methylamino)methyl imidazo[5,1-b]thiazole were used, thereby obtaining 6.9 mg of the title compound.

NMR (D$_2$O) δ(HOD=4.80 ppm): 1.08 (3H, d, J=7.2 Hz), 1.26 (3H, d, J=6.3 Hz), 2.78 (3H, s), 3.07 (1H, m), 3.49 (1H, dd, J$_1$=5.4 Hz, J$_2$=2.5 Hz), 4.19–4.29 (2H, m), 4.53 (1H, d, J=15.8 Hz), 4.59 (1H, d, J=15.8 Hz), 5.27 (1H, d, J=15.0 Hz), 5.70 (1H, d, J=15.0 Hz), 7.60 (1H, s), 7.77 (1H, s)

EXAMPLE 35

(1S,5R,6S)-6-[(1R)-1-hydroxyethyl]-2-[2,3-propanoimidazo[5,1-b]thiazolium-6-yl)methyl-1-methyl-1-carbapen-2-em-3-carboxylate (internal salt)

The same procedure as in Example 1 was repeated except that Cosmosil 40C18 was used for purification, and 122.7 mg of allyl (1S,5R,6S)-6-[(1R)-1-allyloxycarbonyloxyethyl]-2-hydroxymethyl-1-methyl-1-carbapen-2-em-3-carboxylate and 82.8 mg of 2,3-propanoimidazo[5,1-b]thiazole were used, thereby obtaining 16.7 mg of the title compound.

NMR (D$_2$O) δ(HOD=4.75 ppm): 1.05 (3H, d, J=7.2 Hz), 1.21 (3H, d, J=6.4 Hz), 2.60-(2H, m), 2.88 (4H, m), 2.98 (1H, m), 3.42 (1H, dd, J$_1$=6.1 Hz, J$_2$=3.0 Hz), 4.11–4.20 (2H, m), 5.09 (1H, d, J=15.1 Hz), 5.71 (1H, d, J=15.1 Hz), 7.60 (1H, s)

EXAMPLE 36

(1S,5R,6S)-6-[(1R)-1-hydroxyethyl]-2-[3-(1-hydroxyethyl)imidazo[5,1-b]thiazolium-6-yl]methyl-1-methyl-1-carbapen-2-em-3-carboxylate (internal salt)

The same procedure as in Example 1 was repeated except that Cosmosil 40C18 was used for purification, and 155 mg of allyl (1S,5R,6S)-6-[(1R)-1-allyloxycarbonyloxyethyl]-2-hydroxymethyl-1-methyl-1-carbapen-2-em-3-carboxylate and 107 mg of 3-(1-hydroxyethyl)imidazo[5,4-b]thiazole were used, thereby obtaining 40.0 mg of the title compound.

NMR (D$_2$O) δ(HOD=4.80 ppm): 1.09 (3H, d, J=7.2 Hz), 1.24 (3H, d, J=6.4 Hz), 1.65-(3H, d, J=6.6 Hz), 3.01–3.06 (1H, m), 3.44–3.47 (1H, m), 4.15–4.23 (2H, m), 5.11–5.22 (2H, m), 5.78 (1H, d, J=14.9 Hz), 7.41 (1H, s), 7.74 (1H, s), 9.46 (1H, s)

EXAMPLE 37

(1S,5R,6S)-6-[(1R)-1-hydroxyethyl]-2-[3-[N-(N-methylaminosulfonyl)-N-methylamino]methylimidazo[5,1-b]thiazolium-6-yl]methyl-1-methyl-1-carbapen-2-em-3-carboxylate (internal salt)

The same procedure as in Example 1 was repeated except that aniline was used as a trapping agent for an allyl removal reaction, Cosmosil 40C18-PREP was used for purification, and 80.0 mg of allyl (1S,5R,6S)-6-[(1R)-1-allyloxycarbonyloxyethyl]-2-hydroxymethyl-1-methyl-1-carbapen-2-em-3-carboxylate and 92.0 mg of 3-[N-[N-allyloxycarbonyl-N-methylamino]sulfonyl-N-methylamino]methylimidazo[5,1-b]thiazole were used, thereby obtaining 10.7 mg of the title compound.

NMR (D$_2$O) δ(HOD=4.80 ppm): 1.08 (3H, d, J=7.1 Hz), 1.27 (3H, d, J=6.3 Hz), 2.70 (3H, s), 2.82 (3H, s), 3.04–3.07 (1H, m), 3.49 (1H, q, J=3.0 Hz), 3.52–3.68 (1H, m), 4.19–4.27 (2H, m), 4.66 (1H, d, J=15.9 Hz), 4.74 (1H, d, J=15.9 Hz), 5.28 (1H, d, J=14.8 Hz), 5.72 (1H, d, J=14.8 Hz), 7.62 (1H, s), 7.79 (1H, s), 9.28 (0.5H, s, partially exchanged with D)

EXAMPLE 38

(1S,5R,6S)-6-[(1R)-1-hydroxyethyl]-2-(3-[(N-methylamino)sulfonylaminomethylimidazo[5,1-b]thiazolium-6-yl]methyl-1-methyl-1-carbapen-2-em-3-carboxylate (internal salt)

The same procedure as in Example 1 was repeated except that N-methylaniline was used as a trapping agent for an allyl removal reaction, Cosmosil 40C18-PREP was used for purification, and 129.9 mg of allyl (1S,5R,6S)-6-[(1R)-1-allyloxycarbonyloxyethyl]-2-hydroxymethyl-1-methyl-1-carbapen-2-em-3-carboxylate and 158 mg of 3-[(N-allyloxycarbonyl-N-methylaminosulfonylamino]methyl imidazo[5,1-b]thiazole were used, thereby obtaining 31.2 mg of the title compound.

NMR (D$_2$O) δ(HOD=4.80 ppm): 1.08 (3H, d, J=7.4 Hz), 1.26 (3H, d, J=6.4 Hz), 2.61 (3H, s), 3.00–3.11 (1H, m), 3.48 (1H, q, J=3.0 Hz), 4.18–4.28 (2H, m), 4.50 (2H, s), 5.26 (1H, d, J=14.8 Hz), 5.75 (1H, d, J=14.8 Hz), 7.53 (1H, s), 7.79 (1H, s), 9.42 (0.5H, s, partially exchanged with D)

EXAMPLE 39

(1S,5R,6S)-6-[(1R)-1-hydroxyethyl]-2-(3-difluoromethylimidazo[5,1-b]thiazolium-6-yl)methyl-1-methyl-1-carbapen-2-em-3-carboxylate (internal salt)

The same procedure as in Example 1 was repeated except that 97 mg of allyl (1S,5R,6S)-6-[(1R)-1-allyloxycarbonyloxyethyl]-2-hydroxymethyl-1-methyl-1-carbapen-2-em-3-carboxylate and 70 mg of 3-difluoromethylimidazo[5,1-b]thiazole were used, thereby obtaining 7.9 mg of the title compound.

NMR (D$_2$O) δ(HOD=4.82 ppm): 1.12 (3H, d), 1.28 (3H, d), 3.05 (1H, m), 3.50 (1H, dd), 4.18–4.29 (2H, m), 5.22 (1H, d), 5.87 (1H, d), 7.19 (1H, t), 7.85 (1H, s), 8.10 (1H, s), 9.67 (1H, s)

EXAMPLE 40

(1S,5R,6S)-6-[(1R)-1-hydroxyethyl]-2-[3-(hydroxyimino)methylimidazo[5,1-b]thiazolium-6-yl]methyl-1-methyl-1-carbapen-2-em-3-carboxylate (internal salt)

The same procedure as in Example 1 was repeated except that 102 mg of allyl (1S,5R,6S)-6-[(1R)-1-allyloxycarbonyloxyethyl]-2-hydroxymethyl-1-methyl-1-carbapen-2-em-3-carboxylate and 70 mg of 3-(hydroxyimino)methylimidazo[5,1-b]thiazole were used, thereby obtaining 2.3 mg of the title compound.

NMR (D$_2$O) δ(HOD=4.80 ppm): 1.12 (3H, d), 1.28 (3H, d), 3.06 (1H, m), 3.50 (1H, dd), 4.18–4.30 (2H, m), 5.25 (1H, d), 5.81 (1H, d), 7.84 (1H, s), 7.88 (1H, s), 8.40 (1H, s), 9.81 (1H, s)

EXAMPLE 41

(1S,5R,6S)-6-[(1R)-1-hydroxyethyl]-2-(3-formylimidazo[5,1-b]thiazolium-6-yl)methyl-1-methyl-1-carbapen-2-em-3-carboxylate (internal salt)

The same procedure as in Example 1 was repeated except that 93 mg of allyl (1S,5R,6S)-6-[(1R)-1-allyloxycarbonyloxyethyl]-2-hydroxymethyl-1-methyl-1-carbapen-2-em-3-carboxylate and 58 mg of 3-formylimidazo[5,1-b]thiazole were used, thereby obtaining 3.2 mg of the title compound.

NMR (D$_2$O) δ(HOD=4.82 ppm): 1.12 (3H, d), 1.29 (3H, d), 3.04 (1H, m), 3.50 (1H, dd), 4.19–4.30 (2H, m), 5.27 (1H, d), 5.88 (1H, d), 7.92 (1H, s), 8.90 (1H, s), 9.88 (1H, s), 9.97 (1H, s)

EXAMPLE 42

(1S,5R,6S)-6-[(1R)-1-hydroxyethyl]-2-(3-N-methylaminoimidazo[5,1-b]thiazolium-6-yl)methyl-1-methyl-1-carbapen-2-em-3-carboxylate (internal salt)

The same procedure as in Example 1 was repeated except that N-methylaniline was used as a trapping agent for an allyl removal reaction, Cosmosil 40C18-PREP and Cephadex LH-20 were used for purification, and 103 mg of allyl (1S,5R,6S)-6-[(1R)-1-allyloxycarbonyloxyethyl]-2-hydroxymethyl-1-methyl-1-carbapen-2-em-3-carboxylate and 94 mg of 3-(N-allyloxycarbonyl-N-methylamino)imidazo[5,1-b]thiazole were used, thereby obtaining 5.1 mg of the title compound.

NMR (D$_2$O) δ(HOD=4.80 ppm): 1.06 (3H, d, J=11.6 Hz), 1.23 (3H, d, J=6.5 Hz), 2.59 (2×⅓H, s), 2.66 (3×⅓H, s), 2.91 (3×1/3H, s), 2.97–3.07 (1H, m), 3.47 (1H, q, J=3.0 Hz), 4.12–4.28 (2H, m), 5.19 (1H, d, J=14.9 Hz), 5.77 (1H, d, J=14.9 Hz), 6.08 (1×⅔H, s), 7.67 (1H, s), 9.26 (0.8H, s, partially exchanged with D)

EXAMPLE 43

(1S,5R,6S)-6-[(1R)-1-hydroxyethyl]-2-[2-(formylamino)methylimidazo[5,1-b]thiazolium-6-yl]methyl-1-methyl-1-carbapen-2-em-3-carboxylate (internal salt)

The same procedure as in Example 1 was repeated except that 97.2 mg of allyl (1S,5R,6S)-6-[(1R)-1-allyloxycarbonyloxyethyl]-2-hydroxymethyl-1-methyl-1-carbapen-2-em-3-carboxylate and 73.0 mg of 2-(formylamino)methylimidazo[5,1-b]thiazole were used, thereby obtaining 5.4 mg of the title compound.

NMR (D$_2$O) δ(HOD=4.75 ppm): 1.04 (3H, d, J=7.4 Hz), 1.21 (2H, d, J=6.4 Hz), 2.99 (1H, m), 3.43 (1H, dd, J$_1$=6.0 Hz, J$_2$=3.0 Hz), 4.12–4.21 (2H, m), 4.56 (2H, s), 5.13 (1H, d, J=15.0 Hz), 5.70 (1H, d, J=15.0 Hz), 7.63 (1H, s), 7.86 (1H, s), 8.16 (1H, s), 9.26 (1H, s)

EXAMPLE 44

(1S,5R,6S)-6-[(1R)-1-hydroxyethyl]-2-[3-(N-allyl-N-methylamino)methylimidazo[5,1-b]thiazolium-6-yl]methyl-1-methyl-1-carbapen-2-em-3-carboxylate (internal salt)

The same procedure as in Example 1 was repeated except that aniline was used as a trapping agent for a deprotective reaction, Cosmosil 40C18 was used for purification, and 80.5 mg of allyl (1S,5R,6S)-6-[(1R)-1-allyloxycarbonyloxyethyl]-2-hydroxymethyl-1-methyl-1-carbapen-2-em-3-carboxylate and 73.6 mg of 3-(-N-allyloxycarbonyl-N-methylamino)methylimidazo[5,1-b]thiazole were used, thereby obtaining 2.9 mg of the title compound.

NMR (D$_2$O) δ(HOD=4.80 ppm): 1.09 (3H, d, J=7.3 Hz), 1.26 (3H, d, J=6.3 Hz), 2.40 (3H, s), 3.04 (1H, m), 3.29 (2H, m), 3.48 (1H, dd, J$_1$=6.0 Hz, J$_2$=3.0 Hz), 4.00 (2H, s), 4.18–4.27 (2H, m), 5.20 (1H, d, J=14.9 Hz), 5.34 (2H, m), 5.78 (1H, d, J=14.9 Hz), 5.90 (1H, m), 7.55 (1H, s), 7.76 (1H, s)

EXAMPLE 45

(1S,5R,6S)-6-[(1R)-1-hydroxyethyl]-2-[7-(aminosulfonyl)aminomethylimidazo[5,1-b]thiazolium-6-yl]methyl-1-methyl-1-carbapen-2-em-3-carboxylate (internal salt)

The same procedure as in Example 1 was repeated except that Cosmosil 40C18 was used for purification, and 79.5 mg of allyl (1S,5R,6S)-6-[(1R)-1-allyloxycarbonyloxyethyl]-2-hydroxymethyl-1-methyl-1-carbapen-2-em-3-carboxylate and 136 mg of 7-(aminosulfonyl)aminomethylimidazo[5,1-b]thiazole were used, thereby obtaining 1.3 mg of the title compound.

NMR (D$_2$O) δ(HOD=4.80 ppm): 1.13 (3H, d, J=7.2 Hz), 1.26 (3H, d, J=6.5 Hz), 2.93 (1H, m), 3.49 (1H, dd, J$_1$=5.9 Hz, J$_2$=2.8 Hz), 4.16–4.28 (2H, m), 4.51 (2H, s), 5.19 (1H, d, J=15.6 Hz), 5.91 (1H, d, J=15.6 Hz), 7.56 (1H, d, J=4.2 Hz), 7.92 (1H, d, J=4.2 Hz)

EXAMPLE 46

(1S,5R,6S)-6-[(1R)-1-hydroxyethyl]-2-[5-[(R)-1-(formylamino)ethyl]imidazo[5,1-b]thiazolium-6-yl]methyl-1-methyl-1-carbapen-2-em-3-carboxylate (internal salt)

The same procedure as in Example 1 was repeated except that Cosmosil 40C18 was used for purification, and 102.2 mg of allyl (1S,5R,6S)-6-[(1R)-1-allyloxycarbonyloxyethyl]-2-hydroxymethyl-1-methyl-1-carbapen-2-em-3-carboxylate and 292.4 mg of 5-[(R)-1-(formylamino)ethyl]imidazo[5,1-b]thiazole were used, thereby obtaining 4.2 mg of the title compound.

NMR (D$_2$O) δ(HOD=4.75 ppm): 1.15 (3H, d, J=7.4 Hz), 1.21 (3H, d, J=6.3 Hz), 1.60 (2H, d, J=7.4 Hz), 2.92 (1H, m), 3.45 (1H, dd, $J_1$=60 Hz, $J_2$=2.9 Hz), 4.07–4.20 (2H, m), 5.08 (1H, d, J=15.5 Hz), 5.47 (1H, q, J=7.4 Hz), 6.15 (1H, d, J=15.5 Hz), 7.56 (1H, d, J=4.3 Hz), 7.93 (1H, d, J=4.3 Hz), 8.08 (1H, s)

EXAMPLE 47

(1S,5R,6S)-6-[(1R)-1-hydroxyethyl]-2-(5-methylthioimidazo[5,1-b]thiazolium-6-yl)methyl-1-methyl-1-carbapen-2-em-3-carboxylate (internal salt)

The same procedure as in Example 1 was repeated except that N-methylaniline was used as a trapping agent for a deprotective reaction, Cosmosil 40C18 was used for purification, and 72.2 mg of allyl (1S,5R,6S)-6-[(1R)-1-allyloxycarbonyloxyethyl]-2-hydroxymethyl-1-methyl-1-carbapen-2-em-3-carboxylate and 82 mg of 5-methylthioimidazo[5,1-b]thiazole were used, thereby obtaining 1.9 mg of the title compound.

NMR ($D_2O$) δ($\underline{H}$OD=4.80 ppm): 1.20 (3H, d, J=7.4 Hz), 1.26 (3H, d, J=6.3 Hz), 2.52 (3H, s), 2.94 (1H, s), 3.50 (1H, dd, $J_1$=6.1 Hz, $J_2$=3.0 Hz), 4.14 (1H, dd, $J_1$=10.2 Hz, $J_2$=3.0 Hz), 4.23 (1H, m), 5.19 (1H, d, J=15.4 Hz), 6.03 (1H, d, J=15.4 Hz), 7.68 (1H, d, J=4.3 Hz), 7.91 (1H, s), 8.10 (1H, d, J=4.3 Hz)

EXAMPLE 48

(1S,5R,6S)-6-[(1R)-1-hydroxyethyl]-2-(2,3-dihydroxymethylimidazo[5,1-b]thiazolium-6-yl) methyl-1-methyl-1-carbapen-2-em-3-carboxylate (internal salt)

The same procedure as in Example 1 was repeated except that N-methylaniline was used as a trapping agent for a deprotective reaction, Cosmosil 40C18 was used for purification, and 117 mg of allyl (1S,5R,6S)-6-[(1R)-1-allyloxycarbonyloxyethyl]-2-hydroxymethyl-1-methyl-1-carbapen-2-em-3-carboxylate and 88 mg of 2,3-dihydroxymethylimidazo[5,1-b]thiazole were used, thereby obtaining 3.0 mg of the title compound.

NMR ($D_2O$) δ($\underline{H}$OD=4.80 ppm): 1.11 (3H, d, J=7.3 Hz), 1.26 (3H, d, J=6.4 Hz), 3.02–3.08 (1H, m), 3.48 (1H, dd, $J_1$=6.0 Hz, $J_2$=3.0 Hz), 4.18–4.22 (2H, m), 4.85 (2H, s), 4.88 (2H, s), 5.18 (1H, d, J=14.8 Hz), 5.79 (1H, d, J=14.8 Hz), 7.74 (1H, s)

EXAMPLE 49

(1S,5R,6S)-6-[(1R)-1-hydroxyethyl]-2-(2,5-dihydroxymethylimidazo[5,1-b]thiazolium-6-yl) methyl-1-methyl-1-carbapen-2-em-3-carboxylate (internal salt)

The same procedure as in Example 1 was repeated except that N-methylaniline was used as a trapping agent for a deprotective reaction, Cosmosil 40C18 was used for purification, and 84.3 mg of allyl (1S,5R,6S)-6-[(1R)-1-allyloxycarbonyloxyethyl]-2-hydroxymethyl-1-methyl-1-carbapen-2-em-3-carboxylate and 209.0 mg of 2,5-dihydroxymethylimidazo[5,1-b]thiazole were used, thereby obtaining 2.7 mg of the title compound.

NMR ($D_2O$) δ($\underline{H}$OD=4.75 ppm): 1.09 (3H, d, J=6.9 Hz), 1.21 (3H, d, J=6.5 Hz), 2.90 (1H, m), 3.42 (1H, m), 4.10–4.20 (2H, m), 4.92 (2H, s), 5.17 (2H, s), 5.19 (1H, d, J=15.7 Hz), 5.97 (1H, d, J=15.7 Hz), 7.54 (1H, s), 7.77 (1H, s)

EXAMPLE 50

(1S,5R,6S)-6-[(1R)-1-hydroxyethyl]-2-(3-carboxymethylimidazo[5,1-b]thiazolium-6-yl) methyl-1-methyl-1-carbapen-2-em-3-carboxylate (internal salt)

The same procedure as in Example 1 was repeated except that N-methylaniline was used as a trapping agent for a deprotective reaction, Cosmosil 40C18 was used for purification, and 98.8 mg of allyl (1S,5R,6S)-6-[(1R)-1-allyloxycarbonyloxyethyl]-2-hydroxymethyl-1-methyl-1-carbapen-2-em-3-carboxylate and 97.9 mg of 3-allyloxycarbonylmethylimidazo[5,1-b]thiazole were used, thereby obtaining 1.8 mg of the title compound.

NMR ($D_2O$) δ($\underline{H}$OD=4.75 ppm): 1.04 (3H, d, J=7.4 Hz), 1.21 (3H, d, J=6.3 Hz), 2.96 (1H, m), 3.44 (1H, m), 3.81 (2H, s), 4.12–4.18 (2H, m), 5.15 (1H, d, J=15.0 Hz), 5.76 (1H, d, J=15.0 Hz), 7.23 (1H, s), 7.67 (1H, s), 9.31 (1H, s)

EXAMPLE 51

(1S,5R,6S)-6-[(1R)-1-hydroxyethyl]-2-[3-(hydroxyaminocarbonyl)methylimidazo[5,1-b] thiazolium-6-yl]methyl-1-methyl-1-carbapen-2-em-3-carboxylate (internal salt)

The same procedure as in Example 1 was repeated except that N-methylaniline was used as a trapping agent for a deprotective reaction, Cosmosil 40C18 was used for purification, and 92.0 mg of allyl (1S,5R,6S)-6-[(1R)-1-allyloxycarbonyloxyethyl]-2-hydroxymethyl-1-methyl-1-carbapen-2-em-3-carboxylate and 76.1 mg of 3-(hydroxyaminocarbonyl)methylimidazo[5,1-b]thiazole were used, thereby obtaining 6.2 mg of the title compound.

NMR ($D_2O$) δ($\underline{H}$OD=4.75 ppm): 1.02 (3H, d, J=7.4 Hz), 1.18 (3H, d, J=7.0 Hz), 2.89 (1H, m), 3.17 (2H, m), 3.41 (2H, m), 4.10–4.18 (2H, m), 4.85 (1H, d, J=14.9 Hz), 5.47 (1H, d, J=14.9 Hz), 6.83 (1H, s), 7.29 (1H, s), 8.00 (1H, s)

EXAMPLE 52

(1S,5R,6S)-6-[(1R)-1-hydroxyethyl]-2-[3-(N-methoxycarbonylamino) sulfonylaminomethylimidazo[5,1-b]thiazolium-6-yl] methyl-1-methyl-1-carbapen-2-em-3-carboxylate (internal salt)

The same procedure as in Example 1 was repeated except that N-methylaniline was used as a trapping agent for a deprotective reaction, Cosmosil 40C18 was used for purification, and 84.1 mg of allyl (1S,5R,6S)-6-[(1R)-1-allyloxycarbonyloxyethyl]-2-hydroxymethyl-1-methyl-1-carbapen-2-em-3-carboxylate and 90.5 mg of 3-(N-methoxycarbonylamino)sulfonylaminomethylimidazo[5,1-b]thiazole were used, thereby obtaining 1.7 mg of the title compound.

NMR ($D_2O$) δ($\underline{H}$OD=4.75 ppm): 1.06 (3H, d, J=7.2 Hz), 1.21 (3H, d, J=6.3 Hz), 3.18 (1H, m), 3.43 (1H, m), 3.53 (3H, s), 4.14–4.22 (2H, m), 4.48 (2H, s), 5.18 (1H, d, J=14.7 Hz), 5.77 (1H, d, J=14.7 Hz), 7.47 (1H, s), 7.73 (1H, s), 9.40 (1H, s)

EXAMPLE 53

(1S,5R,6S)-6-[(1R)-1-hydroxyethyl]-2-[3-(N-formyl-N-methylamino)methylimidazo[5,1-b] thiazolium-6-yl]methyl-1-methyl-1-carbapen-2-em-3-carboxylate (internal salt)

The same procedure as in Example 1 was repeated except that Cosmosil 40C18 was used for purification, and 119 mg of allyl (1S,5R,6S)-6-[(1R)-1-allyloxycarbonyloxyethyl]-2-hydroxymethyl-1-methyl-1-carbapen-2-em-3-carboxylate and 87 mg of 3-(N-formyl-N-methylamino)methylimidazo [5,1-b]thiazole were used, thereby obtaining 5.7 mg of the title compound.

NMR ($D_2O$) δ($\underline{H}$OD=4.80 ppm): 1.10 (3H, m), 1.27 (3H, m), 2.88 (0.9H, s), 3.03 (2.1H, s), 3.06 (0.3H, m), 3.21

(0.7H, m), 3.48 (1H, m), 4.12–4.30 (2H, m), 4.81 (1.4H, s), 4.87 (0.6H, s), 5.21 (1H, m), 5.77 (1H, m), 7.59 (1H, s), 7.76 (0.7H, s), 7.80 (0.3H, s), 8.17 (0.7H, s), 8.37 (0.3H, s), 9.20 (0.7H, s), 9.39 (0.3H, s)

EXAMPLE 54

(5R,6S)-6-[(1R)-1-hydroxyethyl]-2-(3-(aminosulfonyl)aminomethylimidazo[5,1-b]thiazolium-6-yl]methyl-1-methyl-1-carbapen-2-em-3-carboxylate (internal salt)

The same procedure as in Example 1 was repeated except that 88 mg of allyl (5R,6S)-6-[(1R)-1-allyloxycarbonyloxyethyl]-2-hydroxymethyl-1-methyl-1-carbapen-2-em-3-carboxylate and 87 mg of 3-(aminosulfonyl)aminomethylimidazo[5,1-b]thiazole were used, thereby obtaining 14.2 mg of the title compound.

NMR (D$_2$O) δ(HOD=4.82 ppm): 1.26 (3H, d), 2.86 (2H, m), 3.41 (1H, dd), 4.15–4.30 (2H, m), 4.57 (2H, s), 5.43 (1H, d), 5.64 (1H, d), 7.54 (1H, s), 7.77 (1H, s), 9.40 (1H, s)

EXAMPLE 55

(1S,5R,6S)-6-[(1R)-1-hydroxyethyl]-2-[3-[N-aminosulfonyl-N-(2-hydroxyethyl)amino]methylimidazo[5,1-b]thiazolium-6-yl]methyl-1-methyl-1-carbapen-2-em-3-carboxylate (internal salt)

The same procedure as in Example 1 was repeated except that Cosmosil 40C18 was used for purification, and 83.9 mg of allyl (1S,5R,6S)-6-[(1R)-1-allyloxycarbonyloxyethyl]-2-hydroxymethyl-1-methyl-1-carbapen-2-em-3-carboxylate and 75 mg of 3-[N-aminosulfonyl-N-(2-hydroxyethyl)amino]methylimidazo[5,1-b]thiazole were used, thereby obtaining 2.1 mg of the title compound.

NMR (D$_2$O) δ(HOD=4.80 ppm): 1.07 (3H, d, J=7.2 Hz), 1.26 (3H, d, J=6.4 Hz), 3.07 (1H, m), 3.35 (2H, m), 3.49 (1H, dd, J$_1$=5.4 Hz, J$_2$=3.3 Hz), 3.61 (2H, m), 4.20–4.30 (2H, m), 4.69 (2H, m), 5.28 (1H, d, J=14.5 Hz), 5.68 (1H, d, J=14.5 Hz), 7.58 (1H, s), 7.76 (1H, s), 9.36 (1H, s)

EXAMPLE 56

(1S,5R,6S)-6-[(1R)-1-hydroxyethyl]-2-[3-[N-aminosulfonyl-N-[2-(sulfamoyl)oxyethyl]amino]methylimidazo[5,1-b]thiazolium-6-yl]methyl-1-methyl-1-carbapen-2-em-3-carboxylate (internal salt)

The same procedure as in Example 1 was repeated except that Cosmosil 40C18 was used for purification, and 73 mg of allyl (1S,5R,6S)-6-[(1R)-1-allyloxycarbonyloxyethyl]-2-hydroxymethyl-1-methyl-1-carbapen-2-em-3-carboxylate and 83 mg of 3-[N-aminosulfonyl-N-[2-(aminosulfonyl)oxyethyl]amino]methylimidazo[5,1-b]thiazole were used, thereby obtaining 5.4 mg of the title compound.

NMR (D$_2$O) δ(HOD=4.80 ppm): 1.11 (3H, d, J=7.4 Hz), 1.26 (3H, d, J=6.1 Hz), 3.10 (1H, m), 3.45–3.60 (3H, m), 4.10–4.30 (4H, m), 4.62 (1H, d, J=15.3 Hz), 4.71 (1H, d, J=15.3 Hz), 5.23 (1H, d, J=15.0 Hz), 5.75 (1H, d, J=15.0 Hz), 7.62 (1H, s), 7.76 (1H, s), 9.28 (1H, s)

EXAMPLE 57

(1S,5R,6S)-6-[(1R)-1-hydroxyethyl]-2-( 2,3-dicarbamoylimidazo[5,1-b]thiazolium-6-yl)methyl-1-methyl-1-carbapen-2-em-3-carboxylate (internal salt)

The same procedure as in Example 1 was repeated except that 1,3-dimethyl-2-imidazolidinone was used as a solvent in the second step, N-methylaniline was used as a trapping agent for a deprotective reaction, Cosmosil 40C18 was used for purification, and 97 mg of allyl (1S,5R,6S)-6-[(1R)-1-allyloxycarbonyloxyethyl]-2-hydroxymethyl-1-methyl-1-carbapen-2-em-3-carboxylate and 84 mg of 2,3-dicarbamoylimidazo[5,1-b]thiazole were used, thereby obtaining 7.0 mg of the title compound.

NMR (D$_2$O) δ(HOD=4.80 ppm): 1.15 (3H, d, J=7.2 Hz), 1.30 (3H, d, J=6.4 Hz), 3.06–3.13 (1H, m), 3.49–3.52 (1H, m), 4.20–4.30 (2H, m), 5.22 (1H, d, J=14.9 Hz), 5.79 (1H, d, J=14.9 Hz), 7.86 (1H, s), 9.45 (1H, s)

EXAMPLE 58

(5R,6S)-6-[(1R)-1-hydroxyethyl]-2-(imidazo[5,1-b]thiazolium-6-yl)methyl-1-carbapen-2-em-3-carboxylate (internal salt)

The same procedure as in Example 1 was repeated except that 43 mg of allyl (5R,6S)-6-[(1R)-1-allyloxycarbonyloxyethyl]-2-hydroxymethyl-1-carbapen-2-em-3-carboxylate and 31 mg of imidazo[5,1-b]thiazole were used, thereby obtaining 5.1 mg of the title compound.

NMR (D$_2$O) δ(HOD=4.82 ppm): 1.26 (3H, d), 2.85 (2H, m), 3.41 (1H, dd), 4.15–4.28 (2H, m), 5.38 (1H, d), 5.63 (1H, d), 7.55 (1H, d), 7.72 (1H, s), 7.94 (1H, d), 9.35 (1H, s)

EXAMPLE 59

(5R,6S)-6-[(1R)-1-hydroxyethyl]-2-(5-hydroxymethylimidazo[5,1-b]thiazolium-6-yl)methyl-1-carbapen-2-em-3-carboxylate (internal salt)

The same procedure as in Example 1 was repeated except that 43 mg of (5R,6S)-6-[(1R)-1-allyloxycarbonyloxyethyl]-2-hydroxymethyl-1-carbapen-2-em-3-carboxylate and 96 mg of 5-hydroxymethylimidazo[5,1-b]thiazole were used, thereby obtaining 3.3 mg of the title compound.

NMR (D$_2$O) δ(HOD=4.82 ppm): 1.26 (3H, d), 2.80 (2H, m), 3.39 (1H, dd), 4.12–4.25 (2H, m), 5.18 (2H, s), 5.42 (1H, d), 5.74 (1H, d), 7.60 (1H, d), 7.75 (1H, s), 8.07 (1H, d)

EXAMPLE 60

(1S,5R,6S)-6-[(1R)-1-hydroxyethyl]-2-(3-methoxycarbonylaminoimidazo[5,1-b]thiazolium-6-yl)methyl-1-methyl-1-carbapen-2-em-3-carboxylate (internal salt)

The same procedure as in Example 1 was repeated except that N-methylaniline was used as a trapping agent for an allyl removal reaction, Cosmosil 40C18-PREP was used for purification, and 107.1 mg of allyl (1S,5R,6S)-6-[(1R)-1-allyloxycarbonyloxyethyl]-2-hydroxymethyl-1-methyl-1-carbapen-2-em-3-carboxylate and 75.1 mg of 3-methoxycarbonylaminoimidazo[5,1-b]thiazole were used, thereby obtaining 23.4 mg of the title compound.

NMR (D$_2$O) δ(HOD=4.80 ppm): 1.09 (3H, d, J=7.4 Hz), 1.26 (3H, d, J=6.3 Hz), 2.99–3.10 (1H, m), 3.48 (1H, q, J=3.0 Hz), 4.18–4.27 (2H, m), 5.21 (1H, d, J=15.0 Hz), 5.78 (1H, d, J=15.0 Hz), 7.33 (1H, s), 7.77 (1H, s), 9.38 (1H, s)

MS (FAB$^+$): 421 (M$^+$)

EXAMPLE 61

(1S,5R,6S)-6-[(1R)-1-hydroxyethyl]-2-(3-acetylimidazo[5,1-b]thiazolium-6-yl)methyl-1-methyl-1-carbapen-2-em-3-carboxylate (internal salt)

The same procedure as in Example 1 was repeated except that 104 mg of allyl (1S,5R,6S)-6-[(1R)-1- allyloxycarbonyloxyethyl]-2-hydroxymethyl-1-methyl-1-carbapen-2-em-3-carboxylate and 95 mg of 3-acetylimidazo[5,1-b]thiazole were used, thereby obtaining 15.7 mg of the title compound.

NMR (D$_2$O) δ(HOD=4.82 ppm): 1.14 (3H, d), 1.30 (3H, d), 2.72 (3H, s), 3.05 (1H, m), 3.51 (1H, dd), 4.20–4.30 (2H, m), 5.28 (1H, d), 5.87 (1H, d), 7.89 (1H, s), 8.83 (1H, s), 9.95 (1H, s)

EXAMPLE 62

(1S,5R,6S)-6-[(1R)-1-hydroxyethyl]-2-(3-methoxymethylimidazo[5,1-b]thiazolium-6-yl)methyl-1-methyl-1-carbapen-2-em-3-carboxylate (internal salt)

The same procedure as in Example 1 was repeated except that 76 mg of allyl (1S,5R,6S)-6-[(1R)-1-allyloxycarbonyloxyethyl]-2-hydroxymethyl-1-methyl-1-carbapen-2-em-3-carboxylate and 53 mg of 3-methoxymethylimidazo[5,1-b]thiazole were used, thereby obtaining 8.4 mg of the title compound.

NMR (D$_2$O) δ(HOD=4.82 ppm): 1.13 (3H, d), 1.31 (3H, d), 3.08 (1H, m), 3.47 (3H, s), 3.52 (1H, dd), 4.20–4.33 (2H, m), 4.82 (2H, s), 5.26 (1H, d), (5.85 (1H, d), 7.63 (1H, s), 7.81 (1H, s), 9.48 (1H, s)

EXAMPLE 63

(1S,5R,6S)-6-[(1R)-1-hydroxyethyl]-2-(3-hydroxymethyl-2-methylimidazo[5,1-b]thiazolium-6-yl)methyl-1-methyl-1-carbapen-2-em-3-carboxylate (internal salt)

The same procedure as in Example 1 was repeated except that N-methylaniline was used as a trapping agent for a deprotective reaction, Cosmosil 40C18 was used for purification, and 120 mg of allyl (1S,5R,6S)-6-[(1R)-1-allyloxycarbonyloxyethyl]-2-hydroxymethyl-1-methyl-1-carbapen-2-em-3-carboxylate and 83 mg of 3-hydroxymethyl-2-methylimidazo[5,1-b]thiazole were used, thereby obtaining 12.0 mg of the title compound.

NMR (D$_2$O) δ(HOD=4.80 ppm): 1.09 (3H, d, J=7.3 Hz), 1.25 (3H, d, J=6.3 Hz), 2.46 (3H, s), 3.01–3.06 (1H, m), 3.45–3.48 (1H, m), 4.16–4.24 (2H, m), 4.85 (2H, s), 5.16 (1H, d, J=15.0 Hz), 5.76 (1H, d, J=15.0 Hz), 7.66 (1H, s), 9.33 (1H, s)

EXAMPLE 64

(1S,5R,6S)-6-[(1R)-1-hydroxyethyl]-2-(3-oxamidomethylimidazo[5,1-b]thiazolium-6-yl)methyl-1-methyl-1-carbapen-2-em-3-carboxylate (internal salt)

The same procedure as in Example 1 was repeated except that Cosmosil 40C18 was used for purification, and 114.2 mg of allyl (1S,5R,6S)-6-[(1R)-1-allyloxycarbonyloxyethyl]-2-hydroxymethyl-1-methyl-1-carbapen-2-em-3-carboxylate and 105 mg of 3-oxamidomethylimidazo[5,1-b]thiazole were used, thereby obtaining 7.7 mg of the title compound.

NMR (D$_2$O) δ(HOD=4.80 ppm): 1.07 (3H, d, J=7.3 Hz), 1.26 (3H, d, J=6.3 Hz), 3.04 (1H, m), 3.48 (1H, dd, J$_1$=6.0 Hz, J$_2$=3.0 Hz), 4.08–4.28 (2H, m), 4.75 (2H, s), 5.23 (1H, d, J=14.6 Hz), 5.72 (1H, d, J=14.6 Hz), 7.51 (1H, s), 7.76 (1H, s), 9.34 (1H, s)

EXAMPLE 65

(1S,5R,6S)-6-[(1R)-1-hydroxyethyl]-2-[3-(formylamino)methyl-2-methylimidazo[5,1-b]thiazolium-6-yl]methyl-1-methyl-1-carbapen-2-em-3-carboxylate (internal salt)

The same procedure as in Example 1 was repeated except that N-methylaniline was used as a trapping agent for a deprotective reaction, Cosmosil 40C18 was used for purification, and 102 mg of allyl (1S,5R,6S)-6-[(1R)-1-allyloxycarbonyloxyethyl]-2-hydroxymethyl-1-methyl-1-carbapen-2-em-3-carboxylate and 82 mg of 3-(formylamino)methyl-2-methylimidazo[5,1-b]thiazole were used, thereby obtaining 18.0 mg of the title compound.

NMR (D$_2$O) δ(HOD=4.80 ppm): 1.08 (3H, d, J=7.4 Hz), 1.25 (3H, d, J=6.3 Hz), 2.49 (3H, s), 3.00–3.06 (1H, m), 3.46–3.48 (1H, m), 4.16–4.23 (2H, m), 4.65 (2H, s), 5.17 (1H, d, J=15.0 Hz), 5.73 (1H, d, J=15.0 Hz), 7.66 (1H, s), 8.16 (1H, s), 9.22 (1H, s)

EXAMPLE 66

(1S,5R,6S)-6-[(1R)-1-hydroxyethyl]-2-[3-(hydroxyacetamido)methylimidazo[5,1-b]thiazolium-6-yl]methyl-1-methyl-1-carbapen-2-em-3-carboxylate (internal salt)

The same procedure as in Example 1 was repeated except that Cosmosil 40C18 was used for purification, and 93.6 mg of allyl (1S,5R,6S)-6-[(1R)-1-allyloxycarbonyloxyethyl]-2-hydroxymethyl-1-methyl-1-carbapen-2-em-3-carboxylic acid allyl ester and 85 mg of 3-(hydroxyacetamido)methylimidazo[5,1-b]thiazole were used, thereby obtaining 3.1 mg of the title compound.

NMR (D$_2$O) δ(HOD=4.80 ppm): 1.09 (3H, d, J=7.2 Hz), 1.25 (3H, d, J=6.4 Hz), 3.05 (1H, m), 3.48 (1H, dd, J$_1$=5.9 Hz, J$_2$=2.9 Hz), 4.12 (2H, s), 4.16–4.28 (2H, m), 4.70 (2H, s), 5.20 (1H, d, J=14.9 Hz), 5.76 (1H, d, J=14.9 Hz), 7.44 (1H, s), 7.74 (1H, s), 9.34 (1H, s)

EXAMPLE 67

(1S,5R,6S)-6-[(1R)-1-hydroxyethyl]-2-[2-methyl-3-(aminosulfonyl)aminogmethylimidazo[5,1-b]thiazolium-6-yl]methyl-1-methyl-1-carbapen-2-em-3-carboxylate (internal salt)

The same procedure as in Example 1 was repeated except that N-methylaniline was used as a trapping agent for a deprotective reaction, Cosmosil 40C18 was used for purification, and 128 mg of allyl (1S,5R,6S)-6-[(1R)-1-allyloxycarbonyloxyethyl]-2-hydroxymethyl-1-methyl-1-carbapen-2-em-3-carboxylate and 103 mg of 3-(aminosulfonyl)aminomethyl-2-methylimidazo[5,1-b]thiazole were used, thereby obtaining 4.0 mg of the title compound.

NMR (D$_2$O) δ(HOD=4.80 ppm): 1.07 (3H, d, J=8.1 Hz), 1.25 (3H, d, J=6.3 Hz), 2.48 (3H, s), 3.02–3.08 (1H, m), 3.46–3.49 (1H, m), 4.18–4.25 (2H, m), 4.51 (2H, s), 5.22 (1H, d, J=14.9 Hz), 5.70 (1H, d, J=14.9 Hz), 7.68 (1H, s), 9.27 (1H, s)

EXAMPLE 68

(1S,5R,6S)-6-[(1R)-1-hydroxyethyl]-2-(2-carbamoylimidazo[5,1-b]thiazolium-6-yl)methyl-1-methyl-1-carbapen-2-em-3-carboxylate (internal salt)

The same procedure as in Example 1 was repeated except that 107 mg of allyl (1S,5R,6S)-6-[(1R)-1-allyloxycarbonyloxyethyl]-2-hydroxymethyl-1-methyl-1-carbapen-2-em-3-carboxylate and 74 mg of 2-carbamoylimidazo[5,1-b]thiazole were used, thereby obtaining 7.4 mg of the title compound.

NMR (D$_2$O) δ($\underline{H}$OD=4.82 ppm): 1.05 (3H, d), 1.21 (3H, d), 3.02 (1H, m), 3.43 (1H, dd), 4.13–4.22 (2H, m), 5.18 (1H, d), 5.74 (1H, d), 7.72 (1H, s), 8.51 (1H, s)

| Ex. | R$_1$ | R$_2$ | R$_3$ | R$_4$ | R$_5$ |
|---|---|---|---|---|---|
| 1 | CH$_3$ | H | CH$_2$OH | H | H |
| 2 | ↑ | H | H | H | H |
| 3 | ↑ | H | CONH$_2$ | H | H |
| 4 | ↑ | H | H | CH$_2$NHCHO | H |
| 5 | ↑ | H | H | CH$_2$CH$_2$OH | H |
| 6 | ↑ | CH$_2$OH | CH$_3$ | H | H |
| 7 | ↑ | H | H | H | CH$_2$OH |
| 8 | ↑ | CH$_2$NHCHO | CH$_3$ | H | H |
| 9 | ↑ | H | H | H | CH$_3$ |
| 10 | ↑ | H | CH$_3$ | H | H |
| 11 | ↑ | H | CH$_2$CH$_2$OH | H | H |
| 12 | ↑ | H | CH$_2$CONH$_2$ | H | H |
| 13 | ↑ | H | CH$_2$CH$_2$OCONH$_2$ | H | H |
| 14 | ↑ | H | CH$_2$NHSO$_2$NH$_2$ | H | H |
| 15 | ↑ | H | CH$_2$NHCONH$_2$ | H | H |
| 16 | ↑ | CH$_2$NHSO$_2$NH$_2$ | CH$_3$ | H | H |
| 17 | ↑ | H | CH$_2$NHCHO | H | H |
| 18 | ↑ | H | CONHCH$_2$CH$_2$NH$_2$ | H | H |
| 19 | ↑ | H | CH$_2$NHSO$_2$NH$_2$ | H | H |
| 20 | ↑ | H | CH$_2$CH$_2$NHSO$_2$NH$_2$ | H | H |
| 21 | ↑ | H | COOC$_2$H$_5$ | H | H |
| 22 | ↑ | H | CH$_2$NHSO$_2$CH$_3$ | H | H |
| 23 | ↑ | H | CH$_2$NHSO$_2$N(CH$_3$)$_2$ | H | H |
| 24 | ↑ | H | CONHCH$_2$CH$_2$OH | H | H |
| 25 | ↑ | H | Ph | H | H |
| 26 | ↑ | CH$_2$OH | H | H | H |
| 27 | ↑ | CH$_2$NHSO$_2$N(CH$_3$)$_2$ | CH$_3$ | H | H |
| 28 | ↑ | CH$_2$NHSO$_2$NH$_2$ | H | H | H |
| 29 | ↑ | CH$_2$OCOCH$_3$ | H | H | H |
| 30 | ↑ | H | H | CH$_2$NHSO$_2$NH$_2$ | H |
| 31 | ↑ | H | H | CH$_2$OH | H |
| 32 | ↑ | H | NH$_2$ | H | H |
| 33 | ↑ | H | CH$_2$ONHSO$_2$NH$_2$ | H | H |

-continued

| Ex. | R₁ | R₂ | R₃ | R₄ | R₅ |
|---|---|---|---|---|---|
| 34 | ↑ | H | CH₂N(CH₃)—SO₂NH₂ ↑ | H | H |
| 35 | ↑ | (CH₂)₃ bridging R₂–R₃ ↑ | | H | H |
| 36 | ↑ | H | —CH(OH)—CH₃ ↑ | H | H |
| 37 | ↑ | H | CH₂N(CH₃)—SO₂NHCH₃ ↑ | H | H |
| 38 | ↑ | H | CH₂NHSO₂NHCH₃ | H | H |
| 39 | ↑ | H | CHF₂ | H | H |
| 40 | ↑ | H | —CH=N∼OH ↑ | H | H |
| 41 | ↑ | H | CHO | H | H |
| 42 | ↑ | H | NHCH₃ | H | H |
| 43 | ↑ | CH₂NHCHO | H | H | H |
| 44 | ↑ | H | CH₂N(CH₃)—CH₂CH=CH₂ ↑ | H | H |
| 45 | ↑ | H | H | H | CH₂NHSO₂NH₂ |
| 46 | ↑ | H | H | CH₃, NHCHO (on same C) ↑ | H |
| 47 | ↑ | H | H | SCH₃ | H |
| 48 | ↑ | CH₂OH | CH₂OH | H | H |
| 49 | ↑ | CH₂OH | H | CH₂OH | H |
| 50 | ↑ | H | CH₂COOH | H | H |
| 51 | ↑ | H | CH₂CONHOH | H | H |
| 52 | ↑ | H | CH₂NHSO₂NHCOOCH₃ | H | H |
| 53 | ↑ | H | CH₂N(CH₃)—CHO ↑ | H | H |
| 54 | H | H | CH₂NHSO₂NH₂ | H | H |
| 55 | CH₃ | H | CH₂N(CH₂CH₂OH)—SO₂NH₂ | H | H |

-continued

| Ex. | $R_1$ | $R_2$ | $R_3$ | $R_4$ | $R_5$ |
|---|---|---|---|---|---|
| 56 | ↑ | H | CH$_2$NSO$_2$NH$_2$<br>\|<br>CH$_2$CH$_2$OSO$_2$NH$_2$<br>↑ | H | H |
| 57 | ↑ | CONH$_2$ | CONH$_2$ | H | H |
| 58 | H | H | H | H | H |
| 59 | H | H | H | CH$_2$OH | H |
| 60 | CH$_3$ | H | NHCOOCH$_3$ | H | H |
| 61 | ↑ | H | COCH$_3$ | H | H |
| 62 | ↑ | H | CH$_2$OCH$_3$ | H | H |
| 63 | ↑ | CH$_3$ | CH$_2$OH | H | H |
| 64 | ↑ | H | O O<br>\|\| \|\|<br>CH$_2$NHCCNH$_2$<br>↑ | H | H |
| 65 | ↑ | CH$_3$ | CH$_2$NHCHO | H | H |
| 66 | ↑ | H | O<br>\|\|<br>CH$_2$NHCCH$_2$OH<br>↑ | H | H |
| 67 | ↑ | CH$_3$ | CH$_2$NHSO$_2$NH$_2$ | H | H |
| 68 | ↑ | H | CONH$_2$ | H | H |

Preparation Examples

Preparation for Injection

A pharmaceutical composition containing a compound according to the present invention is aseptically charged into vials so that each vial may contain 1000 mg (potency) of the compound of the invention.

Compound of the present Invention 250 parts (potency)

Lactose 60 parts (potency)

Magnesium stearate 5 parts (potency)

Soft Capsulated Preparation for Rectal Administration

Olive oil 160 parts

Polyoxyethylene lauryl ether 10 parts

Sodium hexamethaphosphate 5 parts

To a base which is a homogeneous mixture of the above ingredients is added 25 parts (potency) of a compound according to the present invention, and the mixture was homogeneously mixed. The resulting mixture is charged into soft capsules for rectal administration so that each capsule may contain 250 mg (potency) of the compound of the invention.

Antibacterial Activity Test

The antibacterial activity of the compounds according to the present invention was demonstrated by the minimum inhibitory concentrations (MIC) of the compounds against various bacteria, measured by a conventional two-fold method. The results are as shown in the following table.

| | MIC (μml) Test Compound | | | | | |
|---|---|---|---|---|---|---|
| Test strain | Ex. 1 | Ex. 8 | Ex. 14 | Ex. 68 | A | B |
| S. aureus 209P JC-1 | <0.025 | <0.025 | <0.025 | <0.025 | <0.025 | <0.025 |
| S. aureus M126* | 6.25 | 6.25 | 3.13 | 6.25 | 50 | 25 |
| E. faecalis W-73 | 6.25 | 3.13 | 3.13 | 6.25 | 12.5 | 1.56 |
| E. coli NIHJ JC-2 | 0.20 | 0.20 | 0.10 | 0.20 | 0.39 | 0.10 |
| K. pneumoniae PC1602 | 0.39 | 0.39 | 0.20 | 0.20 | 3.13 | 0.39 |
| E. coli 255 | 0.20 | 0.20 | 0.10 | 0.20 | 0.39 | 0.20 |
| P. vulgaris GN76 | 1.56 | 1.56 | 0.78 | 0.78 | 12.5 | 3.13 |
| C. freudii GN346 | 0.20 | 0.20 | 0.10 | 0.10 | 0.39 | 0.20 |
| E. cloacae GN747 | 0.20 | 0.20 | 0.10 | 0.20 | 0.39 | 0.20 |
| S. marcescens GN10857 | 0.78 | 0.78 | 0.39 | 0.39 | 1.56 | 0.39 |
| Ps. aeruginosa M-0148 | 6.25 | 6.25 | 1.56 | 3.13 | 6.25 | 1.56 |
| Ps. aeruginosa E-2 | 6.25 | 6.25 | 0.78 | 3.13 | 6.25 | 1.56 |

*: Methicillin-resistant *Staphylococcus aureus*
Compound A: (1S,5R,6S)-6-[(1R)-1-hydroxyethyl]-2-(pyridinium-1-yl)methyl-1-methyl-1-carbapen-2-em-3-carboxylate;
Compound B: Imipenem/Cilastatin Acute toxicity To three ICR male mice, the compound of Example 14 was administered at a dose of 1500 mg/kg i.v. All the animal survived.

What is claimed is:

1. A carbapenem derivative represented by the following formula (I):

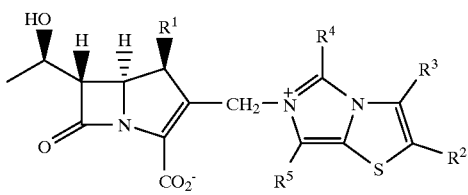

wherein

R$^1$ represents a hydrogen atom or lower alkyl; and

R$^2$, R$^3$, R$^4$ and R$^5$, which may be the same or different, represent a hydrogen atom;
a halogen atom;
hydroxyl;
nitro;
cyano;
carboxyl;
formyl;
lower alkyl;
lower cycloalkyl;
C$_{2-4}$ alkenyl;
C$_{2-4}$ alkynyl;
lower alkyloxy;
lower alkylthio;
lower alkyloxycarbonyl;
carbamoyl;
N-lower alkylcarbamoyl;
N-(amino lower alkyl)carbamoyl;
N-(hydroxy lower alkyl)carbamoyl;
hydroxyaminocarbonyl;
lower alkylcarbonyl;
lower alkylcarbonyloxy;
amino;
N-lower alkylamino;
N-lower alkyl-N-C$_{2-4}$ alkenylamino;
formylamino;
hydroxy lower alkylcarbonylamino;
N-lower alkyl-N-formylamino;
lower alkyloxycarbonylamino;
lower alkyloxyamino;
ureido;
N-lower alkylureido;
oxamoyl;
lower alkylsulfonylamino;
(aminosulfonyl)amino in which hydrogen atom(s) in the two amino groups may be substituted by lower alkyl, hydroxy lower alkyl, lower alkyloxycarbonyl, or aminosulfonyloxy lower alkyl;
(aminosulfonyl)aminoxy;
hydroxyimino; or
aryl,
provided that one or more hydrogen atoms in the lower alkyl, lower cycloalkyl, C$_{2-4}$ alkenyl, and C$_{2-4}$ alkynyl may be substituted by a group selected from the group consisting of a halogen atom; hydroxyl; nitro; cyano; carboxyl; formyl; lower alkyloxy; lower alkylthio; lower alkyloxycarbonyl; carbamoyl; N-lower alkylcarbamoyl; hydroxyaminocarbonyl; lower alkylcarbonyl; lower alkylcarbonyloxy; amino; N-lower alkylamino; N-lower alkyl-N-C$_{2-4}$ alkenylamino; formylamino; lower alkylcarbonylamino; hydroxy lower alkylcarbonylamino; N-lower alkyl-N-formylamino; lower alkyloxycarbonylamino; lower alkyloxyamino; ureido; N-lower alkylureido; oxamoyl; lower alkylsulfonylamino; (aminosulfonyl)amino in which hydrogen atom (s) in the two amino groups may be substituted by lower alkyl, hydroxy lower alkyl, lower alkyloxycarbonyl, or aminosulfonyloxy lower alkyl; guanidino; N-lower alkylguanidino; imino; imino lower alkylamino; hydroxyimino; lower alkyloxyimino; carbamoyloxy; and a lower alkycarbamoyloxy, or R$^3$ and R$^4$ represent 1-oxo-2-azapropylene where the carbon atom at the 1-position of this group is attached to the thiazole ring in formula (I), or any two of R$^2$, R$^3$, R$^4$ and R$^5$ may combine together to form a C$_{3-6}$ alkylene; or a pharmaceutically acceptable salt thereof.

2. A compound or a pharmaceutically acceptable salt thereof according to claim 1, wherein R$^2$, R$^3$, R$^4$ and R$^5$ represent a hydrogen atom.

3. A compound or a pharmaceutically acceptable salt thereof according to claim 1, wherein R$^2$ represents hydroxymethyl.

4. A compound or a pharmaceutically acceptable salt thereof according to claim 1, wherein R$^2$ represents carbamoyl.

5. A compound or a pharmaceutically acceptable salt thereof according to claim 1, wherein R$^2$ represents (formylamino)methyl.

6. A compound or a pharmaceutically acceptable salt thereof according to claim 1, wherein R$^3$ represents carbamoyl.

7. A compound or a pharmaceutically acceptable salt thereof according to claim 6, wherein R$^2$, R$^4$ and R$^5$ represent a hydrogen atom.

8. A compound or a pharmaceutically acceptable salt thereof according to claim 1, wherein R$^3$ represents hydroxymethyl.

9. A compound or a pharmaceutically acceptable salt thereof according to claim 8, wherein R$^2$, R$^4$ and R$^5$ represent a hydrogen atom.

10. A compound or a pharmaceutically acceptable salt thereof according to claim 1, wherein R$^3$ represents (aminosulfonyl)aminomethyl.

11. A compound or a pharmaceutically acceptable salt thereof according to claim 10, wherein R$^2$, R$^4$ and R$^5$ represent a hydrogen atom.

12. A compound or a pharmaceutically acceptable salt thereof according to claim 1, wherein R$^4$ represents hydroxymethyl.

13. A pharmaceutical composition comprising a compound according to any one of claims 1 to 12 together with a pharmaceutically acceptable carrier.

14. A method for treating bacterial infectious diseases, comprising administering a compound according to any one of claims 1 to 12 to a mammal.

* * * * *